(12) United States Patent
Yoon et al.

(10) Patent No.: US 9,943,261 B2
(45) Date of Patent: Apr. 17, 2018

(54) METHOD AND APPARATUS FOR IMPROVING AND MONITORING SLEEP

(71) Applicant: SAMSUNG ELECTRONICS CO., LTD., Suwon-si (KR)

(72) Inventors: Boo-keun Yoon, Suwon-si (KR); Jong-hee Han, Yongin-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 0 days.

(21) Appl. No.: 15/007,375

(22) Filed: Jan. 27, 2016

(65) Prior Publication Data

US 2016/0217672 A1    Jul. 28, 2016

(30) Foreign Application Priority Data

Jan. 28, 2015  (KR) ........................ 10-2015-0013902
Feb. 27, 2015  (KR) ........................ 10-2015-0028588

(51) Int. Cl.
| | |
|---|---|
| G08B 23/00 | (2006.01) |
| A61B 5/00 | (2006.01) |
| A61B 5/024 | (2006.01) |
| A61B 5/08 | (2006.01) |
| A61B 5/0205 | (2006.01) |

(Continued)

(52) U.S. Cl.
CPC ............ A61B 5/4812 (2013.01); A61B 5/024 (2013.01); A61B 5/02055 (2013.01); A61B 5/0816 (2013.01); A61B 5/1123 (2013.01); A61B 5/4818 (2013.01); A61B 5/01 (2013.01); A61B 5/6891 (2013.01)

(58) Field of Classification Search
CPC ....... A61B 5/01; A61B 5/02055; A61B 5/024; A61B 5/0816; A61B 5/1123; A61B 5/4812; A61B 5/4818; A61B 5/6891
USPC ........................................................ 340/575
See application file for complete search history.

(56) References Cited

U.S. PATENT DOCUMENTS 4,228,806 A     10/1980  Lidow
4,420,001 A  *  12/1983  Hearne ................ A61B 5/0816
                                                                600/537
7,956,755 B2    6/2011   Lee et al.
(Continued)

FOREIGN PATENT DOCUMENTS

JP    57-203985 A    12/1982
JP    2005-177158 A   7/2005
(Continued)

OTHER PUBLICATIONS

International Search Report for PCT/KR2016/000354 dated Apr. 21, 2016 [PCT/ISA/210].
(Continued)

Primary Examiner — Naomi J Small
(74) Attorney, Agent, or Firm — Sughrue Mion, PLLC

(57) ABSTRACT

A method performed by an apparatus for inducing a sound sleep to induce a sound sleep of an object who is sleeping includes: determining a first wake-up time of the object based on schedule information of the object; receiving bio-information of the object; determining a sleep state of the object from the bio-information of the object; changing the first wake-up time to a second wake-up time by taking into account the sleep state of the object; and outputting a wake-up alarm signal at the second wake-up time.

6 Claims, 39 Drawing Sheets

(51) Int. Cl.
*A61B 5/11* (2006.01)
*A61B 5/01* (2006.01)

(56) References Cited

U.S. PATENT DOCUMENTS

| | | | |
|---|---|---|---|
| 8,784,322 B2 | 7/2014 | Kim et al. | |
| 2007/0249952 A1 | 10/2007 | Rubin et al. | |
| 2012/0075463 A1* | 3/2012 | Chen | G01S 11/12 |
| | | | 348/135 |
| 2012/0157870 A1* | 6/2012 | Derkx | A61B 7/003 |
| | | | 600/529 |
| 2013/0053718 A1* | 2/2013 | Hung | A61B 5/1128 |
| | | | 600/534 |
| 2014/0210626 A1* | 7/2014 | Kresser | A61B 5/4806 |
| | | | 340/575 |
| 2014/0269224 A1* | 9/2014 | Huh | G04G 13/021 |
| | | | 368/73 |
| 2014/0371635 A1 | 12/2014 | Shinar et al. | |
| 2015/0019215 A1 | 1/2015 | Shin et al. | |
| 2015/0026647 A1* | 1/2015 | Park | G06F 3/0488 |
| | | | 715/863 |
| 2015/0320588 A1* | 11/2015 | Connor | A61F 7/0097 |
| | | | 607/107 |

FOREIGN PATENT DOCUMENTS

| | | |
|---|---|---|
| KR | 10-0647905 B1 | 11/2006 |
| KR | 10-0791371 B1 | 1/2008 |
| KR | 10-0809041 B1 | 3/2008 |
| KR | 10-0927643 B1 | 11/2009 |
| KR | 10-2015-0007422 A | 1/2015 |
| WO | 2008/135985 A1 | 11/2008 |

OTHER PUBLICATIONS

Written Opinion for PCT/KR2016/000354 dated Apr. 21, 2016 [PCT/ISA/237].

* cited by examiner

FIG. 14
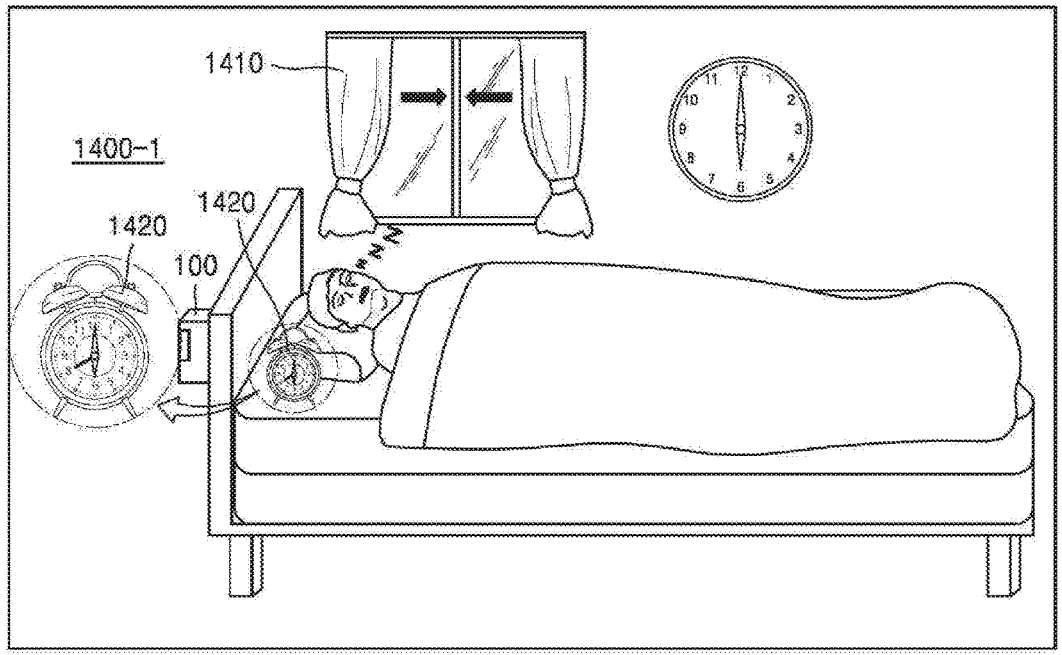
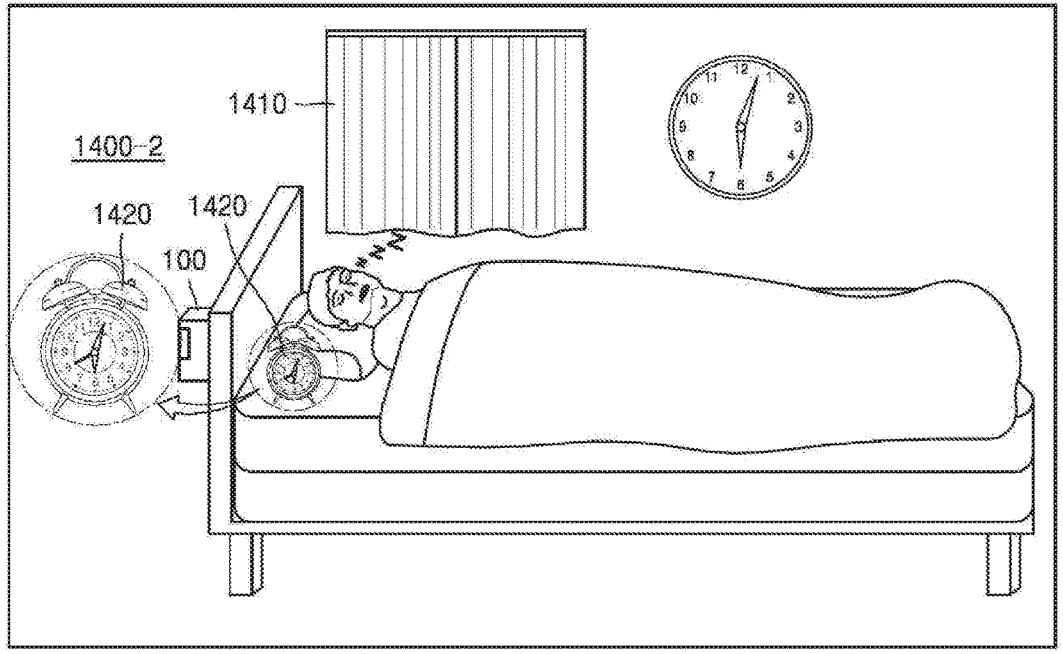

FIG. 16
1. ESTIMATE CYCLE (S1610)
2. REMOVE NOISE (S1620)
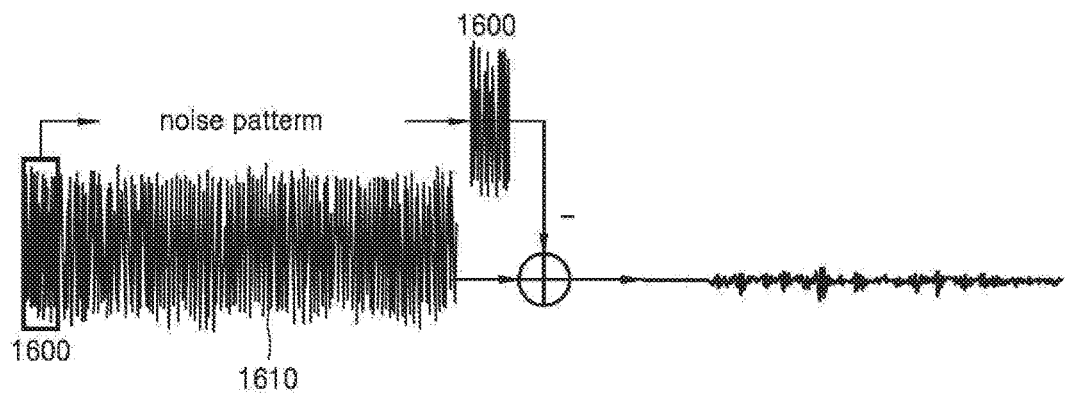

METHOD AND APPARATUS FOR IMPROVING AND MONITORING SLEEP

CROSS-REFERENCE TO RELATED APPLICATION

This application claims the benefit of Korean Patent Application No. 10-2015-0013902, respectively filed on Jan. 28, 2015 in the Korean Intellectual Property Office, and Korean Patent Application No. 10-2015-0028588 filed on Feb. 27, 2015, in the Korean Intellectual Property Office, the disclosures of which are incorporated herein in their entireties by reference.

BACKGROUND

1. Field

Aspects of one or more exemplary embodiments relate to a method and apparatus for improving and monitoring sleep of an object.

2. Description of the Related Art

Materials that are harmful to humans are present in the air and diseases caused by physical and psychological stress are increasingly common. Also, electromagnetic waves released from various electronic devices greatly threaten human health. Accordingly, home appliances designed taking into account users' health, such as washing machines using negative ions, rather than home appliances having improved functions, have been produced.

SUMMARY

Aspects of one or more exemplary embodiments include a method and apparatus for adaptively adjusting a wake-up time based on sleep state information of an object who is sleeping.

Aspects of one or more exemplary embodiments include a method and apparatus for determining an emergency based on bio-information of an object who is sleeping and selectively transmitting alarm information related to the bio-information of the object to at least one of a near-field connection device and a far-field connection device.

Additional aspects will be set forth in part in the description which follows and, in part, will be apparent from the description, or may be learned by practice of the presented exemplary embodiments.

According to an aspect of one or more exemplary embodiments, there is provided a method performed by an apparatus configured to improve a sleep of an object who is sleeping, the method including: determining a first wake-up time of the object based on schedule information corresponding to a schedule of the object; receiving bio-information of the object; determining a sleep state of the object from the bio-information; changing the first wake-up time to a second wake-up time based on the sleep state of the object; and outputting a wake-up alarm signal at the second wake-up time.

The schedule information of the object may include at least one of average wake-up time information, wake-up time information before going to sleep, bedtime information, schedule information before going to sleep, blood alcohol level information before going to sleep, and first schedule information after waking up.

The determining of the sleep state of the object may include determining the sleep state of the object based on at least one of heart rate information, respiration information, movement information, snoring pattern information, eyeball movement information, and body temperature information of the object.

The first wake-up time and the second wake-up time may be earlier than a preset critical time.

The method may further include: measuring an actual wake-up time of the object; determining a remaining time from the actual wake-up time of the object to a preset critical time; selecting at least one activity that is to be performed by the object during the remaining time; and providing information about the selected at least one activity to the object.

The providing of the information about the selected at least one activity may include displaying the information about the selected at least one activity on an external display device.

The determining of the sleep state of the object may include: receiving infrared image information of the object from an external device; and obtaining heart rate information of the object based on the received infrared image information.

The determining of the sleep state of the object may include obtaining at least one of respiration rate information, respiration cycle information, and respiration volume information by using depth value information that is obtained using a depth camera.

The method may further include: detecting that the object wakes up; and providing information about an event that occurs within a preset time after the object wakes up.

The method may further include: detecting that the object is sleeping within a preset time after the second wake-up time; and transmitting information indicating that the object is sleeping to a device of a designated third party.

The outputting of the wake-up alarm signal may include: outputting a first wake-up alarm signal through a first device at the second wake-up time; detecting that the object is sleeping within a preset time after the second wake-up time; and outputting a second wake-up alarm signal through a second device, the second device being different from the first device.

According to an aspect of one or more exemplary embodiments, there is provided an apparatus configured to improve a sleep of an object who is sleeping, the apparatus including: a communicator configured to receive bio-information of the object that is measured by a sensor; a controller configured to determine a sleep state of the object based on the bio-information, determine a first wake-up time of the object based on schedule information corresponding to a schedule of the object, and change the first wake-up time to a second wake-up time based on the sleep state of the object; and an output device configured to output a wake-up alarm signal at the second wake-up time.

The apparatus may further include the sensor configured to obtain the bio-information of the object.

The communicator may be further configured to receive infrared image information of the object from an external display device, and the controller may be further configured to obtain heart rate information of the object based on the received infrared image information, and determine the sleep state of the object based on the heart rate information.

The controller may be further configured to obtain at least one of respiration rate information, respiration cycle information and respiration volume information of the object by using depth value information that is obtained using a depth camera.

The controller may be further configured to detect that the object is sleeping within a preset time after the second wake-up time, and the communicator may be further configured to transmit information indicating that the object is sleeping to a device of a designated third party.

The output device may include a first device and a second device, the second device being different from the first device, and the controller may be further configured to output a first wake-up alarm signal through the first device at the second wake-up time, and, in response to it being detected that the object is sleeping within a preset time after the second wake-up time, output a second wake-up alarm signal through the second device.

According to an aspect of one or more exemplary embodiments, there is provided an alarm method of an apparatus configured to improve sleep of an object who is sleeping, the alarm method including: detecting an alarm event; measuring a sleep depth of the object; determining an alarm condition corresponding to the sleep depth; and outputting an alarm signal related to the alarm event based on the determined alarm condition.

The detecting the alarm event may include receiving an alarm message from an external device using near-field communication.

The determining the alarm condition corresponding to the sleep depth may include adjusting an output cycle of the alarm signal according to the sleep depth.

The determining the alarm condition corresponding to the sleep depth may include: determining an output time of the alarm signal based on the sleep depth; and outputting the alarm signal at the determined output time.

The determining the alarm condition corresponding to the sleep depth may include adjusting an output intensity of the alarm signal based on the sleep depth.

The determining the alarm condition may include determining the alarm condition corresponding to the sleep depth based on an urgency of the alarm event.

The outputting the alarm signal may include outputting the alarm signal as at least one of a vibration signal, an audio signal, and a video signal.

According to an aspect of one or more exemplary embodiments, there is provided an apparatus configured to improve sleep of an object, the apparatus including: a communicator configured to receive information about an alarm event and bio-information of the object that is measured by a sensor; a controller configured to determine a sleep depth of the object based on the bio-information, and determine an alarm condition corresponding to the sleep depth; and an output device configured to output an alarm signal related to the alarm event based on the determined alarm condition.

The apparatus may further include the sensor configured to obtain the bio-information of the object.

The controller may be further configured to adjust an output cycle of the alarm signal according to the sleep depth.

The controller may be further configured to determine an output time of the alarm signal based on the sleep depth, and control the output device to output the alarm signal at the determined output time.

The controller may be further configured to adjust an output intensity of the alarm signal based on the sleep depth.

According to an aspect of one or more exemplary embodiments, there is provided a method performed by an apparatus configured to control ambient noise, the method including: recognizing that an object is sleeping; detecting a noise signal within a predetermined distance from the object through an audio input device; determining a noise pattern having periodic characteristics by analyzing the noise signal; and outputting an anti-phase noise pattern having a phase that is opposite to a phase of the noise pattern through an audio output device.

The outputting of the anti-phase noise pattern may include: measuring a sleep depth of the object; and determining whether to output the anti-phase noise pattern based on the sleep depth of the object.

The determining whether to output the anti-phase noise pattern may include: determining to not output the anti-phase noise pattern and inactivating the audio output device in response to the sleep depth of the object being determined to be greater than a critical value; and determining to output the anti-phase noise pattern and activating the audio output device in response to the sleep depth of the object being determined to be less than or equal to the critical value.

The determining whether to output the anti-phase noise pattern may include adjusting an output intensity of the anti-phase noise pattern based on the sleep depth of the object.

The outputting of the anti-phase noise pattern may include synchronizing a first cycle in which the noise pattern repeats in the noise signal with a second cycle in which the anti-phase noise pattern is output.

The outputting of the anti-phase noise pattern may include outputting the anti-phase noise pattern through a plurality of the audio output devices.

Each of the audio input device and the audio output device may be located within a preset distance from the object.

The determining of the noise pattern having the periodic characteristics may include: receiving, from an external device, cycle information of the noise signal that is generated in the external device; and determining the noise pattern by using the received cycle information.

The determining of the noise pattern by analyzing the noise signal may include selecting a first noise pattern that is generated in a designated external device from among a plurality of noise patterns.

According to an aspect of one or more exemplary embodiments, there is provided an apparatus configured to control ambient noise, the apparatus including: a communicator configured to receive bio-information of an object that is measured from a sensor; an audio input device configured to detect a noise signal; a controller configured to determine a sleep state of the object based on the bio-information, and determine a noise pattern having periodic characteristics by analyzing the noise signal; and an audio output device configured to output an anti-phase noise pattern having a phase that is opposite to a phase of the noise pattern.

The apparatus may further include the sensor configured to obtain the bio-information of the object.

The audio input device may be further configured to detect the noise signal within a predetermined distance from the object.

The apparatus may further include a plurality of audio output devices that each output the anti-phase noise pattern.

According to an aspect of one or more exemplary embodiments, there is provided a non-transitory computer-readable recording medium having embodied thereon a program for executing one or more of the above methods.

According to an aspect of one or more exemplary embodiments, there is provided a method performed by an apparatus configured to monitor a patient, the method including: receiving bio-information of the patient; transmitting the bio-information to an external device; and controlling an environmental device based on the bio-information to adjust an environment around the patient.

The bio-information may include at least one from among an electroencephalogram (EEG), an electrocardiogram (ECG), a heart rate, an oxygen saturation, a blood pressure, a movement, and a blood sugar level, a respiration movement, a body temperature, a sleep depth, and a sleep pattern of the patient.

The environmental device may include at least one from among an air conditioner, an air cleaner, a heater, a lighting device, a humidifier, a ventilator, a window controller, and a curtain controller.

According to an aspect of one or more exemplary embodiments, there is provided a power-saving method of an apparatus, the power-saving method including: determining that an object is in a sleep state; and transmitting, in response to determining that the object is in the sleep state, a power saving mode request to a first external device of one or more external devices, wherein, in response to the power saving mode request, at least one of a power supply is cut off from a second external device of the one or more external devices and the second external device enters a standby mode.

The power-saving method may further include: determining that the object wakes up from the sleep state; and transmitting, in response to determining that the object wakes up from the sleep state, a power saving mode cancellation request to the first external device, wherein, in response to the power saving mode cancellation request, at least one of the power is resupplied to the second external device and the second external device enters an active mode.

BRIEF DESCRIPTION OF THE DRAWINGS

These and/or other aspects will become apparent and more readily appreciated from the following description of one or more exemplary embodiments, taken in conjunction with the accompanying drawings in which:

FIG. 14 illustrates a method performed by the apparatus to control a curtain according to a brightness of light in a bedroom, according to an exemplary embodiment;

FIG. 16 is a graph illustrating a triggered spectral subtraction method using periodic characteristics of a noise pattern, according to an exemplary embodiment;

DETAILED DESCRIPTION

Reference will now be made in detail to one or more exemplary embodiments, examples of which are illustrated in the accompanying drawings.

Most of the terms used herein are general terms that have been widely used in the technical art to which one or more exemplary embodiments pertain. However, some of the terms used herein may be created reflecting intentions of technicians in this art, precedents, or new technologies. Also, some of the terms used herein may be arbitrarily chosen by the present applicant. In this case, these terms are defined in detail below. Accordingly, the specific terms used herein should be understood based on the unique meanings thereof and the whole context of the inventive concept.

As used herein, the singular forms "a", "an" and "the" are intended to include the plural forms as well, unless the context clearly indicates otherwise. It will be further understood that the terms "includes," "including," "comprises," and "comprising" used herein specify the presence of stated features, integers, steps, operations, members, components, and/or groups thereof, but do not preclude the presence or addition of one or more other features, integers, steps, operations, members, components, and/or groups thereof.

Throughout the specification, it will be understood that when an element is referred to as being "connected" to another element, it may be "directly connected" to the other element or "electrically connected" to the other element with intervening elements therebetween. Also, when an element is referred to as being "connected" to another element, it may communicate with the other element by transmitting/receiving a signal. It will be further understood that when a part "includes" or "comprises" an element, unless otherwise defined, the part may further include other elements.

As used herein, the term "and/or" includes any and all combinations of one or more of the associated listed items. Expressions such as "at least one of" when preceding a list of elements, modify the entire list of elements and do not modify the individual elements of the list.

Figure 1:
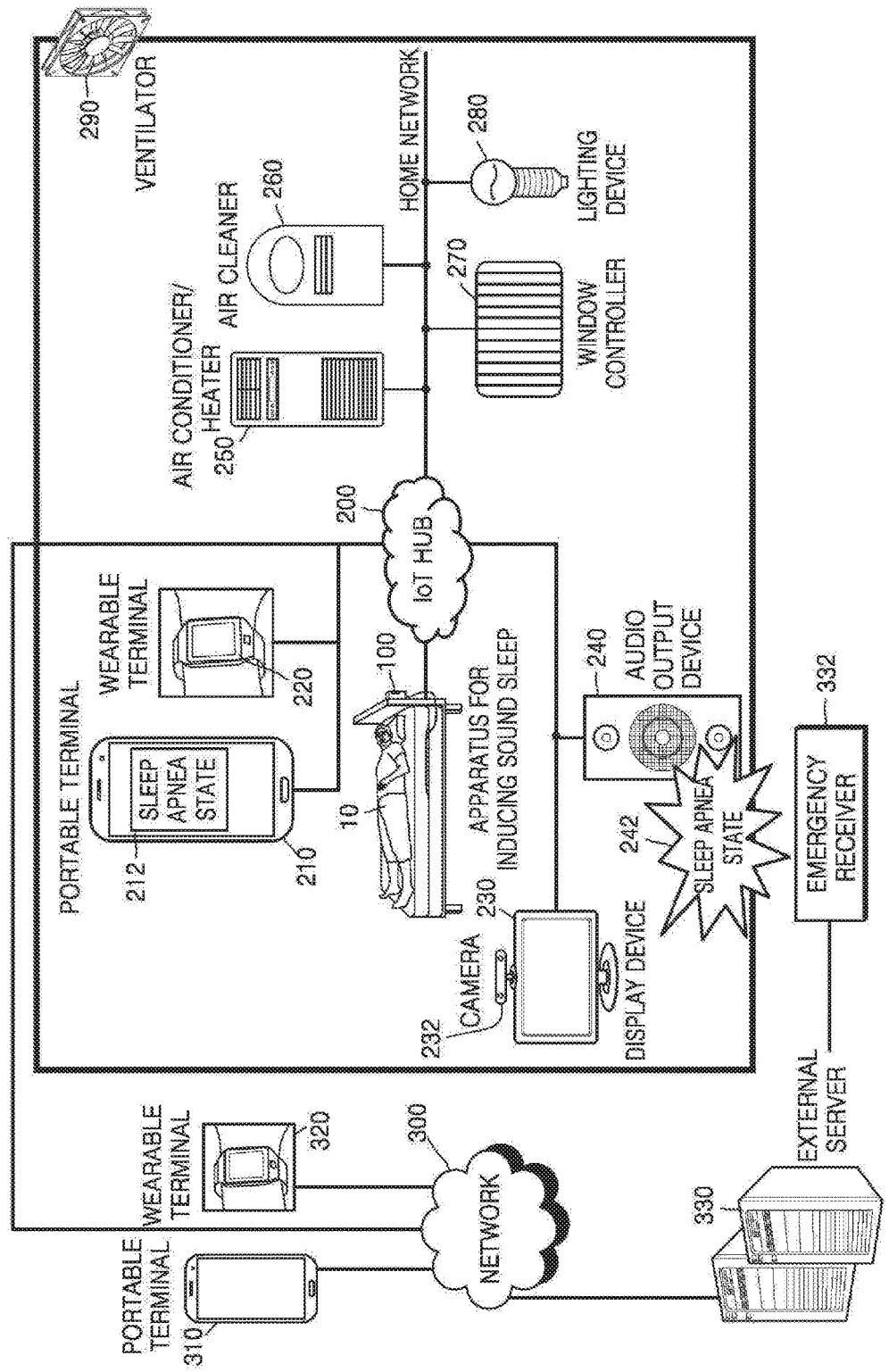
FIG. 1 is a view illustrating a system for monitoring an apnea state of an object, according to an exemplary embodiment.

FIG. 1 is a view illustrating a system for monitoring an apnea state of an object 10, according to an exemplary embodiment.

An apparatus 100 for inducing a sound sleep may obtain bio-information related to a state of the object 10, that is, a user. The object 10 may be, as non-limiting examples, a person, a patient, or an animal who is sleeping. The bio-information may include information of the object 10 that may be obtained by using a sensor that is included in the apparatus 100. As non-limiting examples, the bio-information may include, as non-limiting examples, at least one of an electroencephalogram (EEG), an electrocardiogram (ECG), a heart rate, an oxygen saturation level, a blood pressure, a movement, and a blood sugar level of the object 10. The apparatus 100 may obtain the bio-information not only from the sensor that is included in the apparatus 100 but also from other devices. For example, the apparatus 100 may receive infrared image information of the object 10 that is obtained through a camera 232 that is provided in a display device 230 separate from the apparatus 100. The display device 230 may be a device that displays content, such as a TV or a monitor. The camera 232 may be an infrared camera. The apparatus 100 may obtain heart rate information or respiration information (e.g., respiration rate information, respiration cycle information, or respiration volume information) of the object 10 based on the received infrared image information, as non-limiting examples. The display device 230 may determine the heart rate information or the respiration information based on the infrared image information from the display device 230 and transfer the heart rate information or the respiration information to the apparatus 100.

Alternatively, the camera 232 may be a depth camera. The apparatus 100 may obtain, as non-limiting examples, at least one of respiration rate information, respiration cycle information, respiration volume information, and heart rate information of the object 10 based on depth value information that is obtained through the depth camera. An image of the object 10 that is captured by the camera 232 may be an image of a specific region of the object 10. For example, the camera 232 may obtain information about an image of the chest of the object 10.

The apparatus 100 may transmit information to another device according to the obtained bio-information. The information that is transmitted to the other device may include an alarm signal related to the obtained bio-information. The apparatus 100 may compare the obtained bio-information with reference bio-information and may transmit information to the other device according to a result of the comparison.

According to an exemplary embodiment, the alarm signal may include a control signal for controlling a function of the other device. When it is determined according to the obtained bio-information that the object 10, who is sleeping, is in an apnea state, the apparatus 100 may select a specific device for improving the apnea state of the object 10. The apparatus 100 may transmit a control signal to the selected specific device. For example, the apparatus 100 may transmit an air cleaning request signal to an air cleaner 260.

According to an exemplary embodiment, the apparatus 100 may be connected to an Internet of things (IoT) hub 200 in order to transmit information to the other device. The apparatus 100 may transmit the alarm signal to the specific device through the IoT hub 200. The IoT hub 200 may be a gateway or a server for connecting IoT devices.

Also, the term 'IoT device' used herein may refer to a device that collects data through a sensor and shares the collected data with other IoT devices through a network interface. Examples of the IoT device may include, but are not limited to, a smartphone, a wearable terminal (e.g., a wearable glass, a ring, a necklace, a wristband, a wristwatch, a shoe, an earring, a hair band, a garment, a glove, or a thimble), a door locking device, a sensor system, a smart bulb, a refrigerator, a washing machine, an air conditioner, an audio system, a TV, a robot cleaner, a humidifier, a smart fork, a ventilator, a window controller, an air cleaner, a kitchen gadget, a bicycle, an exercise machine, and a toilet kit.

According to an exemplary embodiment, the apparatus 100 may determine a device to which the alarm signal (e.g., a signal indicating that the object 10 is in an apnea state) is to be transmitted according to a period of time for which the apnea state lasts. For example, when the period of time for which the apnea state lasts is greater than a first critical value, the apparatus 100 may transmit a first alarm signal to a near-field connection device using near-field wireless communication in order to correct the apnea state. For example, the apparatus 100 may transmit the alarm signal to a portable terminal 210 or a wearable terminal 220 that is located in a near-field communication zone. Examples of the portable terminal 210 may include, but are not limited to, a smartphone, a personal digital assistant (PDA), a cellular phone, a navigation system, and a digital multimedia broadcasting (DMB) terminal. Also, the wearable terminal 220 refers to a body-borne terminal such as a smart watch, a head-mounted display (HMD), or a wearable computer, but is not limited thereto. The portable terminal 210 or the wearable terminal 220 that receives the alarm signal may display a message 212 indicating that the object 10 is in the apnea state or may output a vibration signal or an alarm sound. In this case, a user who uses the portable terminal 210 or the wearable terminal 220 may recognize a state of the object 10 based on the message 212 indicating that the object 10 is in the apnea state.

According to another exemplary embodiment, the apparatus 100 may transmit the alarm signal to an audio output device 240 and may cause the audio output device 240 to output a sound signal 242 indicating that the object 10 is in the apnea state. According to another exemplary embodiment, the apparatus 100 may transmit the alarm signal to a device that is connected to a home network. For example, the apparatus 100 may adjust a temperature in a room by using an air conditioner/heater 250, may change the air in the room by using the air cleaner 260, may open or close a window by using a window controller 270, or may adjust an illuminance in the room by using a lighting device 280. Alternatively, the apparatus 100 may ventilate the room by using a ventilator 290.

When the period of time for which the apnea state of the object 10 lasts is greater than a second critical value, the apparatus 100 may transmit a second alarm signal (e.g., a signal indicating that the apnea state of the object 10 lasts for a second critical time or more) about the obtained bio-information to a far-field connection device using far-field communication. The second critical value may be greater than the first critical value. That is, when the period of time for which the apnea state lasts exceeds the second critical value, the apparatus 100 may determine that the object 10 is in a very bad state, and may not only transmit the first alarm signal to the near-field connection device but also additionally transmit the second alarm signal to the far-field connection device. For example, the apparatus 100 may transmit the alarm signal to a portable terminal 310 (e.g., a cellular phone of a designated doctor) or a wearable terminal 320 that is located in a far-field communication zone through a network 300, and thus may enable a user (e.g., the designated doctor) of the portable terminal 310 or the wearable terminal 320 to recognize the state of the object 10. Examples of the portable terminal 310 may include, but are not limited to, a smartphone, a PDA, a cellular phone, a navigation system, and a DMB terminal. Also, the wearable terminal 320 refers to a body-borne terminal such as a smart watch, an HMD, or a wearable computer, but is not limited thereto. The portable terminal 310 or the wearable terminal 320 may be a terminal (referred to as a designated terminal of a doctor) of a designated doctor who is designated for the object 10.

According to another exemplary embodiment, the apparatus 100 may transmit the alarm signal to an external server 330 of a medical institute or an emergency care center through the network 300. The external server 330 that receives the alarm signal may transmit information indicating that the object 10 is in an emergency through an emergency receiver 332 to the medical institute or the emergency care center. For example, the external server 330 that receives the alarm signal may transmit information about a device for diagnosing the object 10 or a drug for emergency treatment to the portable terminal 310 of a rescue squad, e.g., an emergency medical technician. In this case, the rescue squad may rapidly gather up the device for diagnosing the object 10 or the drug before departure.

Also, the apparatus 100 may receive information related to the state of the object 10 in response to the alarm signal that is transmitted to the outside. For example, the apparatus 100 may receive from the outside information about an action to be taken by the object 10 who is in the apnea state and may output the received information on the display device 230. Also, at least one of the apparatus 100, the display device 230, the portable terminal 210, and the wearable terminal 220 may receive information about the device for diagnosing the object 10 or the drug for emergency treatment from the external server 330. Accordingly, when the rescue squad has arrived, the rescue squad may receive the information about the device for diagnosing the object 10 or the drug for emergency treatment.

The apparatus 100 may be a device that is included in a bed, as shown in FIG. 1, or is located under a mattress and may measure a respiration movement, a pulse, a body temperature, and blood pressure of the object 10, or may be a device that is separate from the bed. The apparatus 100 may be included in the IoT hub 200. Alternatively, the apparatus 100 may be included in the display device 230. However, one or more exemplary embodiments are not limited thereto, and the apparatus 100 may be any appropriate apparatus that may obtain information about the object 10. For convenience of description, the following will be explained on the assumption that the apparatus 100 is attached to the bed.

Also, according to another exemplary embodiment, the apparatus 100 may set a wake-up time of the object 10 when the object 10 is sleeping. The apparatus 100 may determine a first wake-up time of the object 10 based on object information. The object information may include at least one of average wake-up time information, wake-up time information before going to sleep, bedtime information, schedule information before going to sleep, blood alcohol level information before going to sleep, body temperature information before going to sleep, heart rate information before going to sleep, and environment information (e.g., an atmospheric temperature or humidity) around the object 10. Next, the apparatus 100 may obtain sleep state information of the object 10 who is sleeping based on the obtained bio-information. Also, the apparatus 100 may change the first wake-up time into a second wake-up time by taking into account the sleep state information of the object 10. That is, the apparatus 100 may periodically or continuously update a set wake-up time according to the sleep state information of the object 10 until a current time is the set wake-up time. For example, when the object 10 is in the apnea state for a short period of time, the apparatus 100 may delay the wake-up time of the object 10. When a current time is the set wake-up time, the apparatus 100 may output a wake-up alarm signal.

Figure 2:
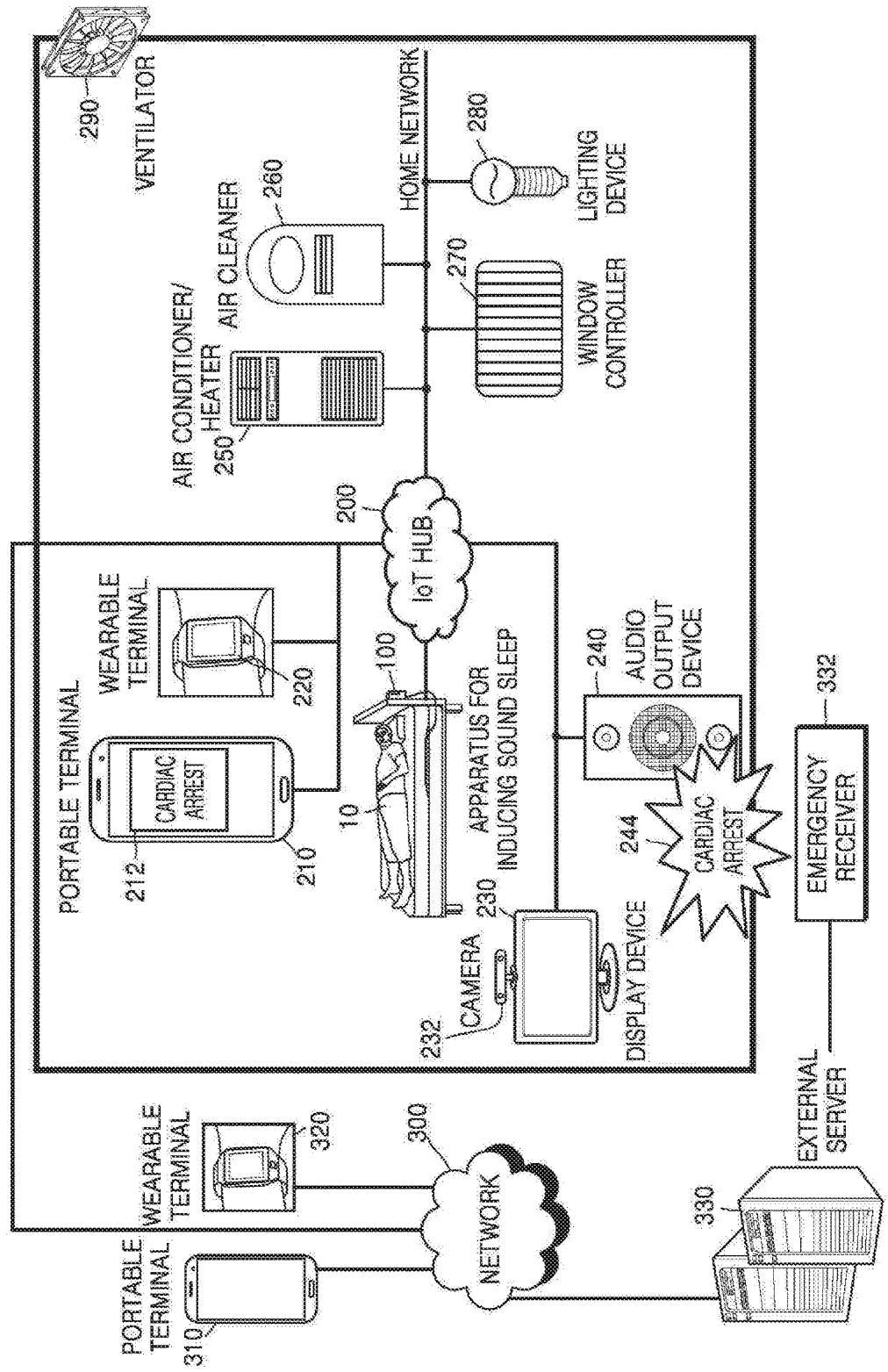
FIG. 2 is a view illustrating a system for monitoring for cardiac arrest of the object, according to an exemplary embodiment.

FIG. 2 is a view illustrating a system for monitoring for cardiac arrest of the object 10, according to an exemplary embodiment.

The apparatus 100 may obtain bio-information related to a state of the object 10, that is, a user. For example, the bio-information may include, as non-limiting examples, at least one of an EEG, an ECG, a heart rate, an oxygen saturation level, a blood pressure, a movement, and a blood sugar level of the object 10. The apparatus 100 may obtain the bio-information not only from a sensor that is included in the apparatus 100 but also from another device. For example, the apparatus 100 may receive infrared image information of the object 10 that is obtained through the camera 232 that is provided in the display device 230 that is disposed separate from the apparatus 100. The display device 230 may be a device that displays content, such as a TV or a monitor, and the camera 232 may be, as a non-limiting example, an infrared camera. The apparatus 100 may obtain, as non-limiting examples, heart rate information or respiration information (e.g., respiration rate information, respiration cycle information, or respiration volume information) of the object 10 based on the received infrared image information. For example, the apparatus 100 may receive from the display device 230 the heart rate information or the respiration information of the object 10 that is obtained by the display device 230 based on the infrared image information.

Alternatively, the camera 232 may be a depth camera. The apparatus 100 may obtain, as non-limiting examples, at least one of respiration rate information, respiration cycle information, respiration volume information, and heart rate information of the object 10 based on depth value information that is obtained through the depth camera. An image of the object 10 that is captured by the camera 232 may be an image of a specific region of the object 10. For example, the camera 232 may obtain information about an image of the chest of the object 10.

The apparatus 100 may obtain information about a state related to a heartbeat of the object 10 based on the bio-information. The apparatus 100 may transmit information to another device according to the state related to the heartbeat that is determined according to the bio-information. The information that is transmitted to the other device may include an alarm signal related to the obtained bio-information.

The alarm signal may include a control signal for controlling a function of the other device. When it is determined based on the obtained bio-information that the object 10 shows a presymptom related to cardiac arrest, the apparatus 100 may select a specific device for preventing the object 10 from suffering from cardiac arrest. The apparatus 100 may transmit the control signal to the selected specific device. For example, when a heart rate of the object 10 that is included in the bio-information indicates that a pulse of the object 10 is irregular, the apparatus 100 may control a device around the apparatus 100 in order to correct the irregular pulse of the object 10. The apparatus 100 may transmit the alarm signal to the specific device through the IoT hub 200.

The apparatus 100 may transmit a first alarm signal to a near-field connection device using near-field wireless communication in order to prevent the object 10 from suffering from cardiac arrest. For example, the apparatus 100 may transmit the alarm signal to the portable terminal 210 or the wearable terminal 220. Examples of the portable terminal 210 may include, but are not limited to, a smartphone, a PDA, a cellular phone, a navigation system, and a DMB terminal. The wearable terminal 220 may refer to, as non-limiting examples, a body-borne terminal such as a smart watch, an HMD, or a wearable computer. The portable terminal 210 or the wearable terminal 220 that receives the alarm signal may display a message 214 indicating that the object 10 is likely to suffer from cardiac arrest or may output a vibration signal or an alarm sound. In this case, a user of the portable terminal 210 or the wearable terminal 220 may recognize a state of the object 10 based on the message 214 indicating that the object 10 is likely to suffer from cardiac arrest. Also, the portable terminal 210 or the wearable terminal 220 that receives the alarm signal may display information about measures for preventing the object 10 from suffering from cardiac arrest. The information about the measures for preventing the object 10 from suffering from cardiac arrest may be stored in the portable terminal 210 or the wearable terminal 220, or may be obtained from an external device through a search or an additional request.

According to another exemplary embodiment, the apparatus 100 may transmit the alarm signal to the audio output device 240. In this case, the audio output device 240 may generate an alarm sound 244 (e.g., a sound indicating that the object 10 is likely to suffer from cardiac arrest), and thus may notify the object 10 or a third person of the state of the object 10. According to another exemplary embodiment, the apparatus 100 may transmit the alarm signal to a device that is connected to a home network. For example, the apparatus 100 may adjust a temperature in a room by using the air conditioner/heater 250, may change the air in the room by using the air cleaner 260, may open or close a window by using the window controller 270, may adjust an illuminance in the room by using the lighting device 280, or may ventilate the room by using the ventilator 290.

Also, when it is determined that the object 10 goes into cardiac arrest, the apparatus 100 may transmit a second alarm signal (e.g., information indicating that the object 10 has gone into cardiac arrest) to a far-field connection device using far-field communication. That is, when the object 10 goes into cardiac arrest and thus is in an emergency, the apparatus 100 may notify not only the device around the apparatus 100 but also a far-field connection device that the object 10 is in an emergency. For example, the apparatus 100 may transmit the alarm signal to the portable terminal 310 or the wearable terminal 320 that is located in a far-field communication zone through the network 300, and thus may enable a user (e.g., a doctor in charge) of the portable terminal 310 or the wearable terminal 320 to recognize the state of the object 10. Examples of the portable terminal 310 may include, but are not limited to, a smartphone, a PDA, a cellular phone, a navigation system, and a DMB terminal. Also, the wearable terminal 320 may refer to, as non-limiting example, a body-borne terminal such as a smart watch, an HMD, or a wearable computer. The portable terminal 310 or the wearable terminal 320 may be a designated terminal of a doctor designated for the object 10.

According to another exemplary embodiment, the apparatus 100 may transmit the alarm signal to the external server 330 of a medical institute or an emergency care center through the network 300. The external server 330 that receives the alarm signal may notify the medical institute or the emergency care center that the object 10 is in an emergency through the emergency receiver 332. For example, the external server 330 that receives the alarm signal may transmit information about a device for diagnosing the object 10 or a drug for emergency treatment to the portable terminal 310 of a rescue squad. In this case, the rescue squad may rapidly gather up the device or the drug before departure.

Also, the apparatus 100 may receive information related to the state of the object 10 in response to the alarm signal that is transmitted to an external device. For example, the apparatus 100 may receive information about an action to be taken by the object 10 who goes into cardiac arrest state, and may output the received information on the display device 230. Also, at least one of the apparatus 100, the display device 230, the portable terminal 210, and the wearable terminal 220 may receive information about the device for diagnosing the object 10 or the drug for emergency treatment from the external server 330 that receives the alarm signal. Accordingly, when the rescue squad has arrived, the rescue squad may receive the information about the device for diagnosing the object 10 or the drug for emergency treatment.

The apparatus 100 may be a device that is included in a bed, as shown in FIG. 2, or is located under a mattress and may measure a respiration movement, a pulse, a body temperature, and a blood pressure of the object 10, or may be a device that is separate from the bed. The apparatus 100 may be included in the IoT hub 200. The apparatus 100 may be included in the display device 230. However, one or more exemplary embodiments are not limited thereto, and the apparatus 100 may be any appropriate device capable of obtaining information about the object 10.

Figure 3A:
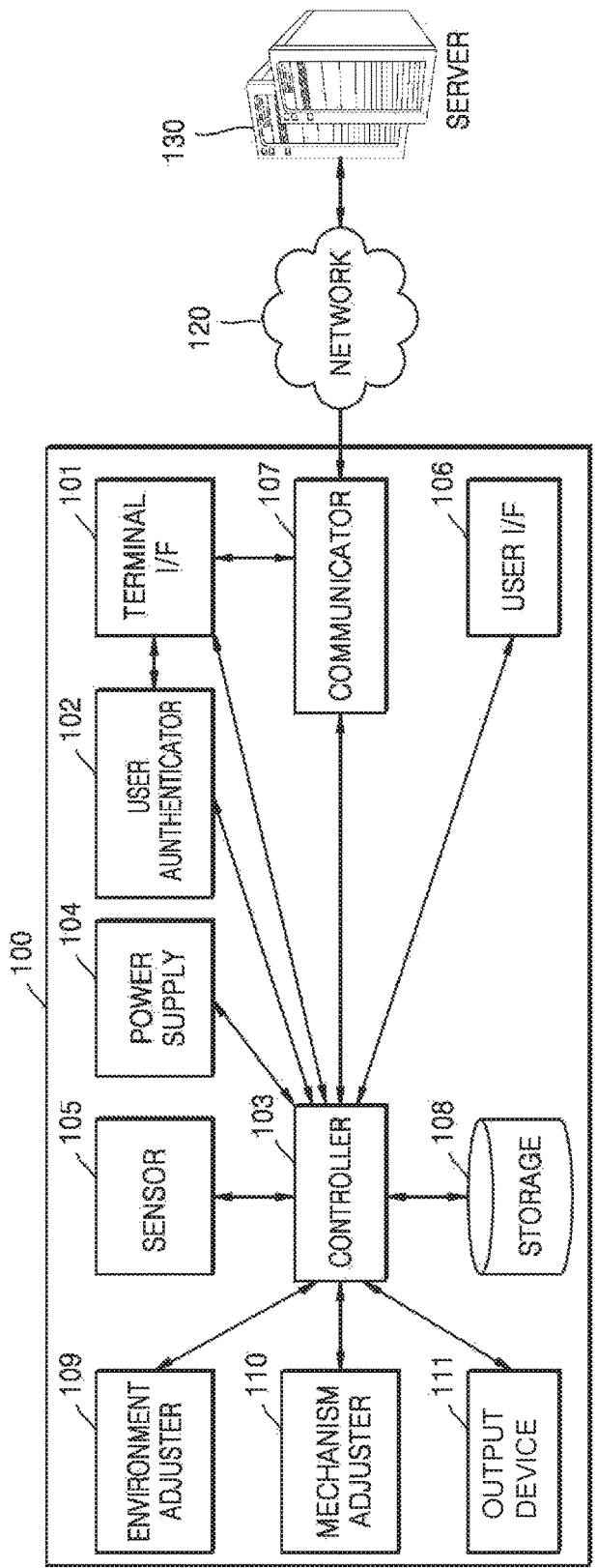
FIG. 3A is a block diagram of an apparatus for inducing a sound sleep, according to an exemplary embodiment.

FIG. 3A is a block diagram of the apparatus 100 according to an exemplary embodiment. The apparatus 100 may include a terminal interface (I/F) 101, a user authenticator 102, e.g., a user authenticating unit, a controller 103, e.g., a processor, a power supply 104, e.g., a power supply unit, a sensor 105, a user interface (I/F) 106, a communicator 107, e.g., a transceiver, a storage 108, e.g., a memory or a storage unit, an environment adjuster 109, e.g., an environment adjusting unit, a mechanism adjuster 110, e.g., a mechanism adjusting unit, and an output device 111, e.g., an audio/video (A/V) unit or an outputter. The apparatus 100 of FIG. 3A is a device for monitoring a sleep state of the object 10 and may be applied to another similar device. Examples of the other similar device may include, as non-limiting examples, a TV, a set-top box, a refrigerator, a washing machine, a PC, a laptop computer, a tablet computer, and a smartphone.

The terminal interface 101 may detect another device that may be connected to the apparatus 100. For example, the terminal interface 101 may detect the portable terminal 210, the wearable terminal 220, the display device 230, the audio output device 240, e.g., a speaker, the air conditioner/heater 250, the air cleaner 260, the window controller 270, the lighting device 280, the ventilator 290, the portable terminal 310, the wearable terminal 320, and the external server 330. Representative examples of the portable terminals 210 and 310 may include a cellular phone, a PDA, an MPEG audio layer 3 (MP3) player, a laptop computer, and a palm-top computer. Representative examples of the wearable terminals 220 and 320 may include a smart watch, an HMD, and a wearable computer.

The user authenticator 102 determines whether a user of the apparatus 100 has a right to use the apparatus 100. The apparatus 100 according to an exemplary embodiment may be installed in a private house or may be installed in a public accommodation such as a hospital. The user authenticator 102 for preventing the apparatus 100 installed in a public accommodation allows only users who have a right to use the apparatus 100 to use the apparatus 100. For example, only the user who pays a fee for the apparatus 100 and gets the right to use the apparatus 100 may use the apparatus 100. However, when the apparatus 100 is installed in a private house, the user authenticator 102 may be omitted.

The user authenticator 102 may authenticate a user by using the portable terminal 210 or the wearable terminal 220 of the object 10. The user authenticator 102 may authenticate the user through voice recognition, fingerprint recognition, or iris recognition. An authentication method may vary according to one or more exemplary embodiments.

When bio-information of the object 10 is not obtained (for example, the portable terminal 210 or the wearable terminal 220 of the object 10 is not located in a near-field communication zone) or when the user authenticator 102 determines that the object 10 has no right to use the apparatus 100, the controller 103 maintains a stand-by mode in which the power supply 104 supplies power only to the terminal interface 101, the user interface 106, and the controller 103. When it is determined that the portable terminal 210 or the wearable terminal 220 is connected in a wired manner or may be connected using near-field wireless communication via the terminal interface 101, the controller 103 controls a power adjusting function of the power supply 104 to change a power state of the apparatus 100 from the stand-by mode to an active mode in which power is supplied to all of the elements in addition to the terminal interface 101, the user authenticator 102, and the controller 103. However, when the apparatus 100 is included or installed in a piece of furniture such as a bed or a sofa, the controller 103 may control the power supply 104 to change from the stand-by mode to the active mode according to a seating state of the user, that is, a pressed state of the piece of furniture, instead of whether the portable terminal 210 or the wearable terminal 220 is detected. However, one or more exemplary embodiments are not limited thereto, and a method performed by the controller 103 to control power may vary according to various exemplary embodiments.

When the apparatus 100 is installed in a public accommodation, the controller 103 may control the power adjusting function of the power supply 104 to change from the stand-by mode to the active mode only when the user authenticator 102 determines that the user of the apparatus 100 has the right to use the apparatus 100. When it is determined that there is no object 10 in the active mode, the controller 103 may control the power adjusting function of the power supply 104 to change from the active mode to the stand-by mode. That is, when the portable terminal 210 or the wearable terminal 220 of the user is connected to the terminal interface 101 by being inserted into a connector that is attached to the terminal interface 101 or using near-field wireless communication, the apparatus 100 may enter the active mode in which all functions are performed. However, when the connection between the terminal interface 101 and the portable terminal 210 or the wearable terminal 220 of the user is turned off, the apparatus 100 may enter the stand-by mode in which only a function of detecting the connection between the terminal interface 101 and the portable terminal 210 or the wearable terminal 220 is performed.

Also, the controller 103 may control a communication function of the communicator 107 to download personal information of the object 10 from the portable terminal 210 or the wearable terminal 220 of the object 10, to connect the apparatus 100 to a server 130 that is located at a remote place through a network 120, or to transmit an alarm signal to the portable terminal 30 or the wearable terminal 320 of a rescue squad (for example, a 911 rescue squad) or a doctor in charge through a public switched telephone network (PSTN). The server 130 may include, as non-limiting examples, at least one of a cloud server, a personalized server, a medical institute server, and a health information storage server (e.g., an electronic medical record (EMR) server, an electronic health record (EHR) server, or a personal health record (PHR) server). The server 130 may include an intelligence engine, and may analyze sleep state information of the object 10 that is obtained by the apparatus 100 through the intelligence engine and may transmit information for controlling a peripheral device to the apparatus 100. For example, the server 130 may transmit to the apparatus 100 information for controlling a hygrometer to measure humidity at 1-hour intervals when the object 10 is sleeping and to measure humidity at 2-hour intervals when the object 10 is awake.

Also, the controller 103 may control a sensing function of the sensor 105 to sense an environment around the apparatus 100 or to measure the bio-information of the object 10. The controller 103 may control at least one function provided by the apparatus 100 based on at least one of the personal information that is downloaded and remote control information that is received through the communicator 107, the information about the environment and the bio-information that are obtained by the sensor 105, and direct control information that is input to the user interface 106. According to an exemplary embodiment, functions provided by the apparatus 100 may include an environment adjusting function of the environment adjuster 109, a mechanism operation adjusting function of the mechanism adjuster 110, an A/V content output adjusting function of the output device 111, a noise reducing function of the output device 111, a power adjusting function of the power supply 104, the communication function of the communicator 107, and the sensing function of the sensor 105.

Examples of the personal information of the object 10 may include body state information of the object 10, identification information of the object 10, health care history information of the object 10, and preferred A/V content information of the object 10. Examples of the body state information of the object 10 may include the bio-information measured by the portable terminal 210, the wearable terminal 220, or the camera 232, and the bio-information measured by a measurement device of the apparatus 100. That is, the controller 103 may control a wake-up time managing function, an alarm signal transmitting function, and an environment adjusting function provided by the apparatus 100 according to a body state of the object 10 indicated by the personal information that is downloaded through the communicator 107. When the bio-information indicates an emergency such as an apnea state for a long period of time, a heart attack, or cardiac arrest state, the controller 103 may control the communication function of the communicator 107 to transmit an alarm signal indicating a state of the object 10 to a far-field connection device.

Examples of the bio-information of the object 10 may include an ECG, an oxygen saturation level ($SpO_2$), an EEG, a blood pressure, a pulse, a respiration movement, and a body temperature of the object 10. The sensor 105 may include various sensors in order to obtain the bio-information of the object 10. Alternatively, the apparatus 100 may receive, from another device, the bio-information that is obtained by the other device. For example, the apparatus 100 may receive image information about the object 10 that is obtained through the camera 232, or may receive the bio-information that is detected through the portable terminal 210 or the wearable terminal 220.

Examples of the identification information of the object 10 may include a gender, an age, a height, a weight, and a schedule for today of the object 10. Also, examples of the health care history information of the object 10 may include preferred content information from among A/V content indicated by a health care history of the object 10, and preferred environment information (e.g., a temperature, humidity, or an illuminance) around the apparatus 100. Health care information may be information that is generated based on the health care history of the object 10, information that is manually set in real time by a health care professional, or information that is automatically set by a health care system.

If the identification information of the object 10 is the age of the object 10, the controller 103 may control the sensing function of the sensor 105 to reduce an interval at which the sensor 105 measures an ECG in proportion to the age of the object 10. That is, as the age of the object 10 increases, an interval at which an ECG is measured may decrease, in order to prevent an abrupt heart attack in old age may be prevented by reducing an ECG measurement interval.

The controller 103 may determine a first wake-up time of the object 10 based on schedule information of the object 10 and may change the first wake-up time to a second wake-up time by taking into account sleep state information of the object 10.

The controller 103 may determine an alarm condition corresponding to a sleep depth of the object 10. For example, the controller 103 may determine an alarm cycle, an alarm intensity, and an alarm type according to the sleep depth of the object 10. Also, the controller 103 may determine the alarm condition according to the sleep depth of the object 10 and an urgency of an alarm content.

When a noise signal is detected within a predetermined distance from the object 10 who is sleeping, the controller 103 may analyze the noise signal and may determine a noise pattern having periodic characteristics. The controller 103 may control the output device 111 to output an anti-phase noise pattern having a phase that is opposite to that of the determined noise pattern. In this case, noise around the object 10 may be removed or reduced.

The power supply 104 may change a power state of a customized bed from the stand-by mode to the active mode or from the active mode to the stand-by mode under the control of the controller 103.

The sensor 105 may obtain the bio-information of the object 10 under the control of the controller 103. The sensor 105 may obtain information about a body state of the object 10 (e.g., the sleep state information when the object 10 is sleeping) by measuring a bio-signal of the object 10, The user interface 106 may receive selection information about whether the bio-information of the object 10 is measured, and selection information about whether the portable terminal 310 and the wearable terminal 320 that are located at a remote place are connected to the server 330. The user interface 106 may receive control information for enabling the object 10 to manually control the apparatus 100.

The communicator 107 may download the personal information of the object 10 from another device under the control of the controller 103. Also, the communicator 107 may receive information from the other device. For example, when the object 10 is in an emergency, the communicator 107 may receive information about an action to be taken by the object 10 from the portable terminal 310, the wearable terminal 320, or the server 330.

The storage 108 may store a program for processing and controlling the controller 103, and may store input/output data (e.g., the bio-information of the object 10, the sleep state information of the object 10, and the schedule information of the object 10).

The storage 108 may include at least one type of storage medium selected from among a flash memory type, a hard disk type, a multimedia card micro type, a card type memory (e.g., an SD or XD memory), random-access memory (RAM), static RAM (SRAM), read-only memory (ROM), electrically erasable programmable read-only memory (EE-PROM), programmable read-only memory (PROM), a magnetic memory, a magnetic disk, and an optical disk. The apparatus 100 may run a web storage or a cloud server that performs a storage function of the storage 108 on the Internet. Programs that are stored in the storage 108 may be classified into a plurality of modules according to functions of the programs.

Figure 3B:
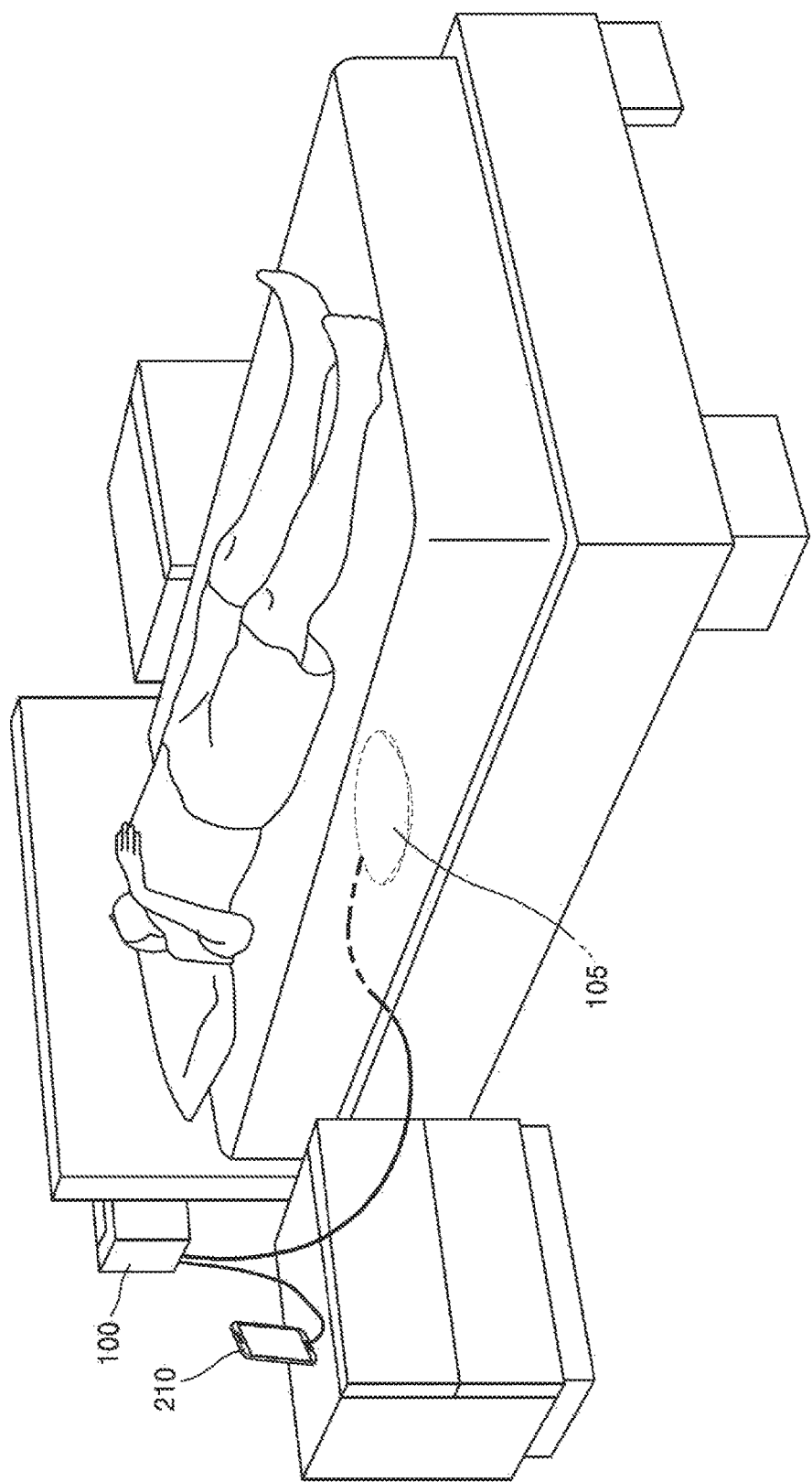
FIG. 3B is a view illustrating an outer appearance of the apparatus, according to an exemplary embodiment.

FIG. 3B is a view illustrating an outer appearance of the apparatus 100, according to an exemplary embodiment.

The apparatus 100, including the controller 103, may be located around the object 10, who is sleeping. For example, the apparatus 100 may be attached to a bed. However, one or more exemplary embodiments are not limited thereto. For example, the apparatus 100 may be included in the IoT hub 200, may be included in the display device 230, or may be attached to a pillow. Also, the apparatus 100 may be any apparatus appropriate for obtaining information about the object 10.

According to an exemplary embodiment, the apparatus 100 may be connected to the portable terminal 210 (e.g., a smartphone, a wearable glass, or a smart watch) of the object 10. For example, the apparatus 100 may be connected to IoT devices such as a washing machine, a coffee machine, a refrigerator, a robot cleaner, an air conditioner, a humidifier, and a lighting device. The apparatus 100 may be connected in a wired or wireless manner to the IoT devices. Also, the apparatus 100 may be indirectly connected to the IoT devices through a home network or the IoT hub 200, or may be directly connected to the IoT devices.

The sensor 105 may be located inside or outside the apparatus 100. The sensor 105 may be separate from the controller 103 of the apparatus 100 and may be located in a mattress. Alternatively, the sensor 105 may be located in the pillow, may be located on a wrist or an ankle of the object 10, or may be located at an edge of the bed.

The sensor 105 may be connected in a wired or wireless manner to the apparatus 100. The sensor 105 may be connected to the apparatus 100 in a wired manner through a cable, or in a wireless manner using near-field wireless communication such as Bluetooth, ZigBee, or Wi-Fi Direct.

Figure 4:
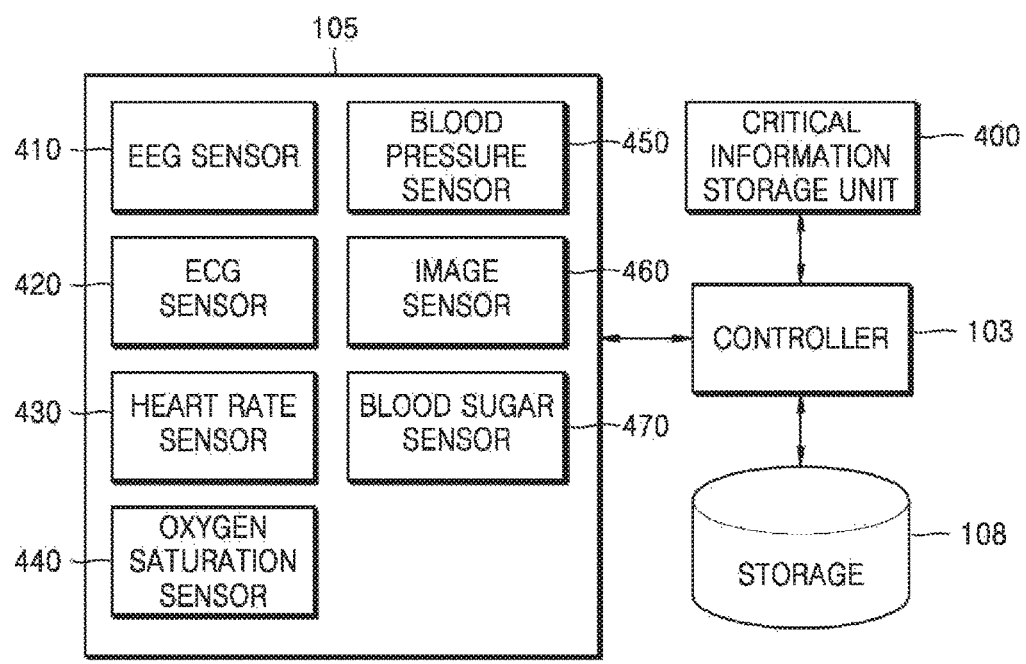
FIG. 4 is a block diagram of a sensor of the apparatus, according to an exemplary embodiment.

FIG. 4 is a block diagram of the sensor 105 of the apparatus 100, according to an exemplary embodiment.

The sensor 105 of the apparatus 100 may include an EEG sensor 410, an ECG sensor 420, a heartrate sensor 430, an oxygen saturation sensor 440, a blood pressure sensor 450, an image sensor 460, and a blood sugar sensor 470. The elements shown in FIG. 4 are exemplarily, and the sensor 105 may include additional, alternative, or fewer elements than those illustrated in FIG. 4. Also, the elements of FIG. 4 may be provided in an external device, instead of being included in the apparatus 100.

The EEG sensor 410 includes a sensor that may electrically detect an EEG of the object 10. The ECG sensor 420 includes a sensor that may detect an ECG that is a record of electric current that is generated by a heart muscle during each heartbeat. The heartrate sensor 430 includes a sensor that may measure a heart rate per unit time. The oxygen saturation sensor 440 includes a sensor that may detect oxygen saturation in the blood of the object 10 either by using an oximeter or by using an oxygen dissociation curve. The blood pressure sensor 450 may include a sensor that may measure blood pressure of the object 10 by using a direct method or a compression method. The direct method is a method involving directly inserting a tube into a carotid artery and measuring blood pressure by using a pressure gauge that is connected to the tube. The compression method is a method involving measuring blood pressure by measuring a pressure that changes or blocks the flow of blood. The image sensor 460 may include a device for capturing an image of the object 10. The image sensor 460 may include at least one of an infrared camera and a depth camera. The infrared camera refers to a camera that may obtain an image by detecting infrared rays. The depth camera refers to a camera that may detect a depth value from the depth camera to the object 10. The blood sugar sensor 470 includes a sensor that may measure a blood sugar level of the object 10 by measuring glucose or the like in blood.

The sensor 105 may include a microphone for detecting a snoring sound, an odor sensor or an alcohol sensor for measuring an alcohol concentration of the object 10, a motion sensor for detecting a movement of the object 10, a temperature sensor for measuring a temperature of the object 10, and a humidity sensor for measuring the amount of emitted sweat. According to an exemplary embodiment, the humidity sensor may measure the amount of emitted sweat of the object 10 by measuring a change in the amount of moisture of a sheet that contacts the object 10.

Also, the apparatus 100 according to an exemplary embodiment may further include a critical information storage 400, e.g., a critical information storage unit. The critical information storage 400 stores reference bio-information that is compared with the bio-information that is obtained through the sensor 105. For example, the reference bio-information may include a first critical value and a second critical value that are compared with the bio-information. When a value that is included in the bio-information is greater than the first critical value and is less than the second critical value, the controller 103 may control the communicator 107 to transmit a first alarm signal that is stored in the storage 108 to a near-field connection device using near-field communication. When a response signal to the first alarm signal is not received or the value that is included in the obtained bio-information is greater than or equal to the second critical value, the controller 103 may transmit a second alarm signal that is stored in the storage 108 to a far-field connection device using far-field communication.

Figure 5:
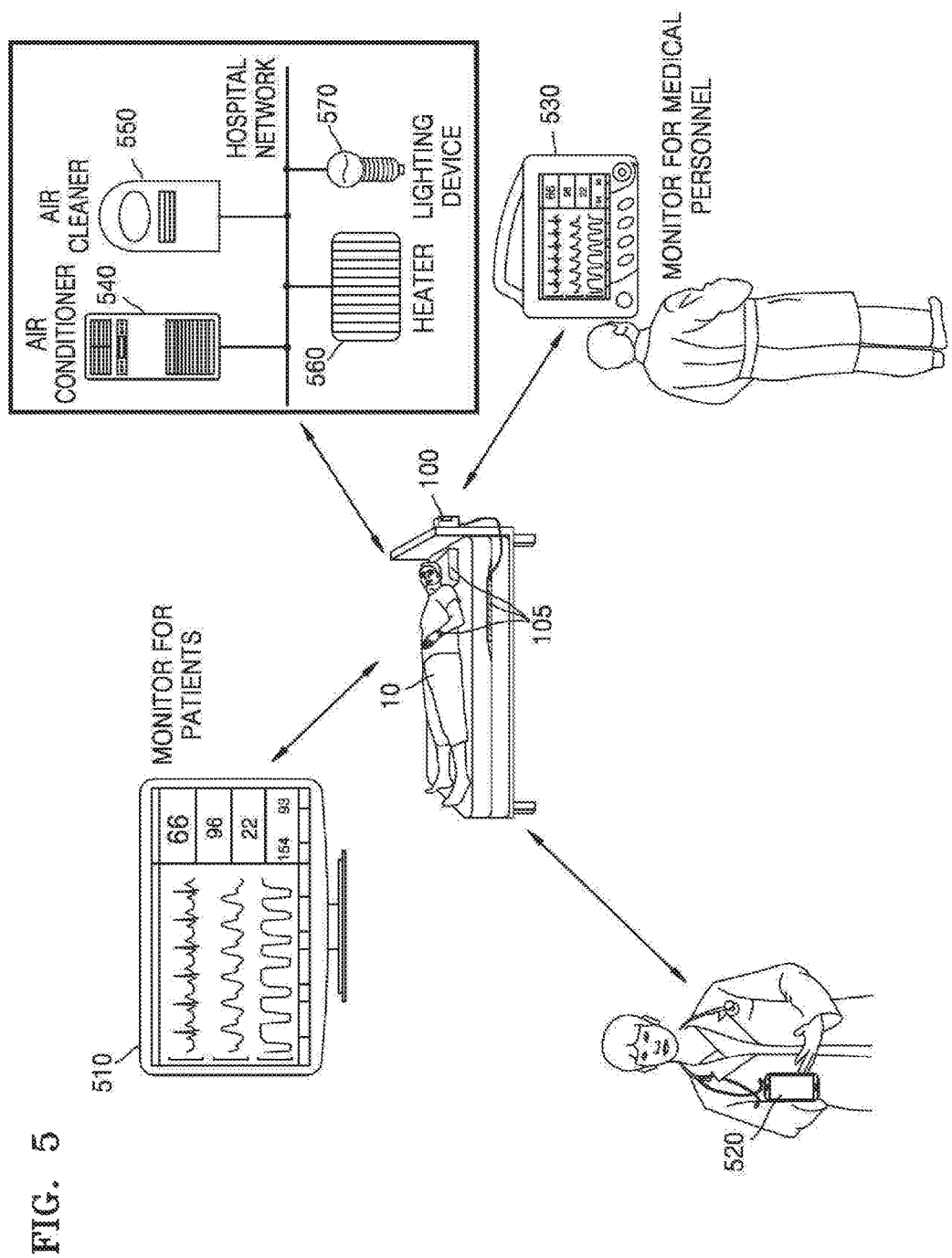
FIG. 5 is a view illustrating a system for monitoring the object in a hospital, according to an exemplary embodiment.

FIG. 5 is a view illustrating a system for monitoring the object 10 in a hospital, according to an exemplary embodiment.

When the apparatus 100 is installed in the hospital, the apparatus 100 may obtain information about a state of the object 10. For example, the apparatus 100 may obtain information about at least one of an EEG, an ECG, a heart rate, an oxygen saturation, a blood pressure, a movement, a blood sugar level, a respiration movement, a body temperature, a sleep depth, and a sleep pattern that are sensed through the sensor 105. The apparatus 100 may transmit the obtained information to a portable terminal 520 of a doctor in charge, a monitor for patients 510, or a monitor for medical personnel 530. Information that is displayed on the monitor for patients 510 and information that is displayed on the portable terminal 520 of the doctor in charge or the monitor for medical personnel 530 may be different from each other.

Also, the apparatus 100 may control devices such as an air conditioner 540, an air cleaner 550, a heater 560, and a lighting device 570 that are connected to a hospital network in order to control an environment around the object 10 based on the obtained information.

Figure 6:
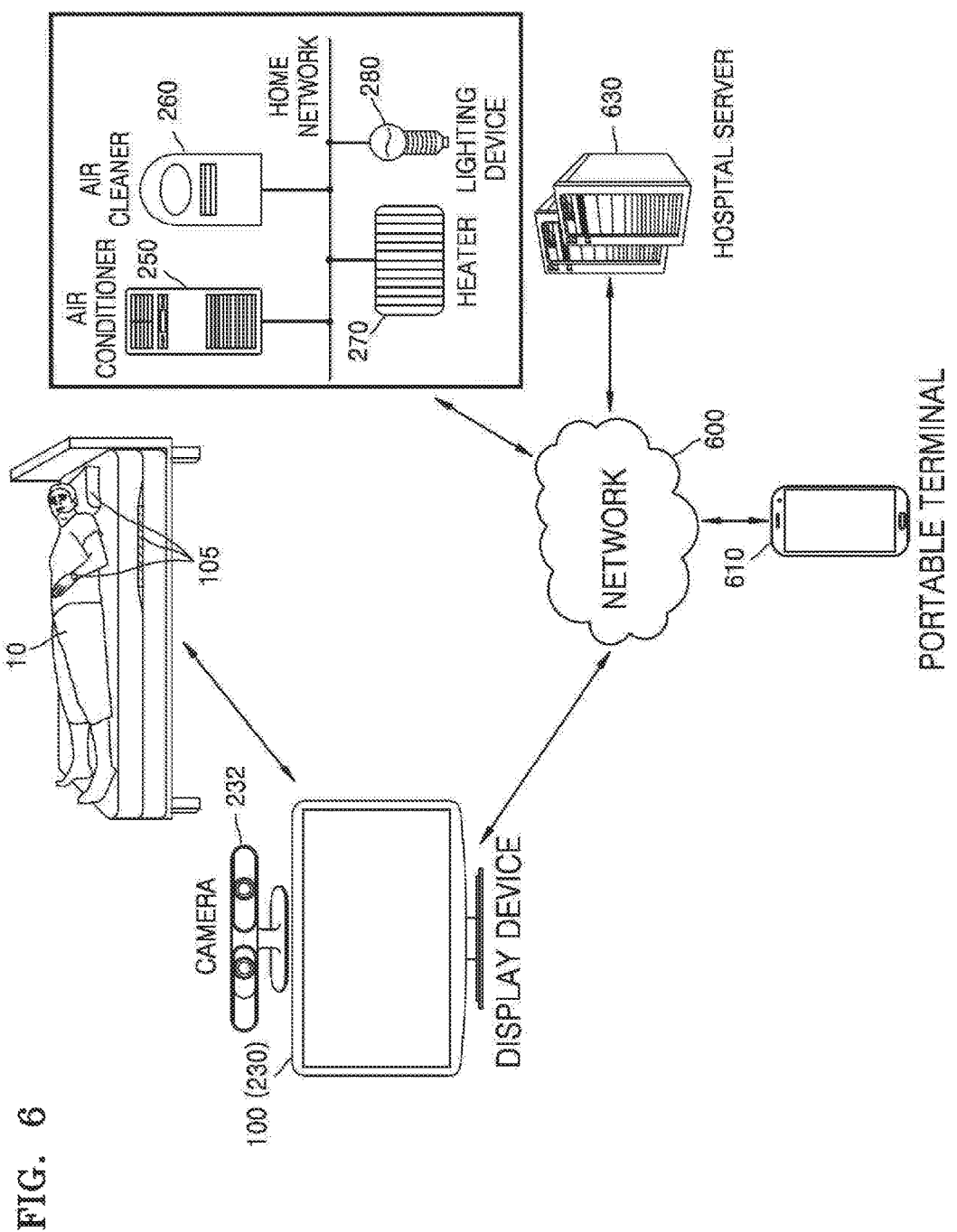
FIG. 6 is a view illustrating a system used by a display device to monitor the object, according to an exemplary embodiment.
Figure 7:
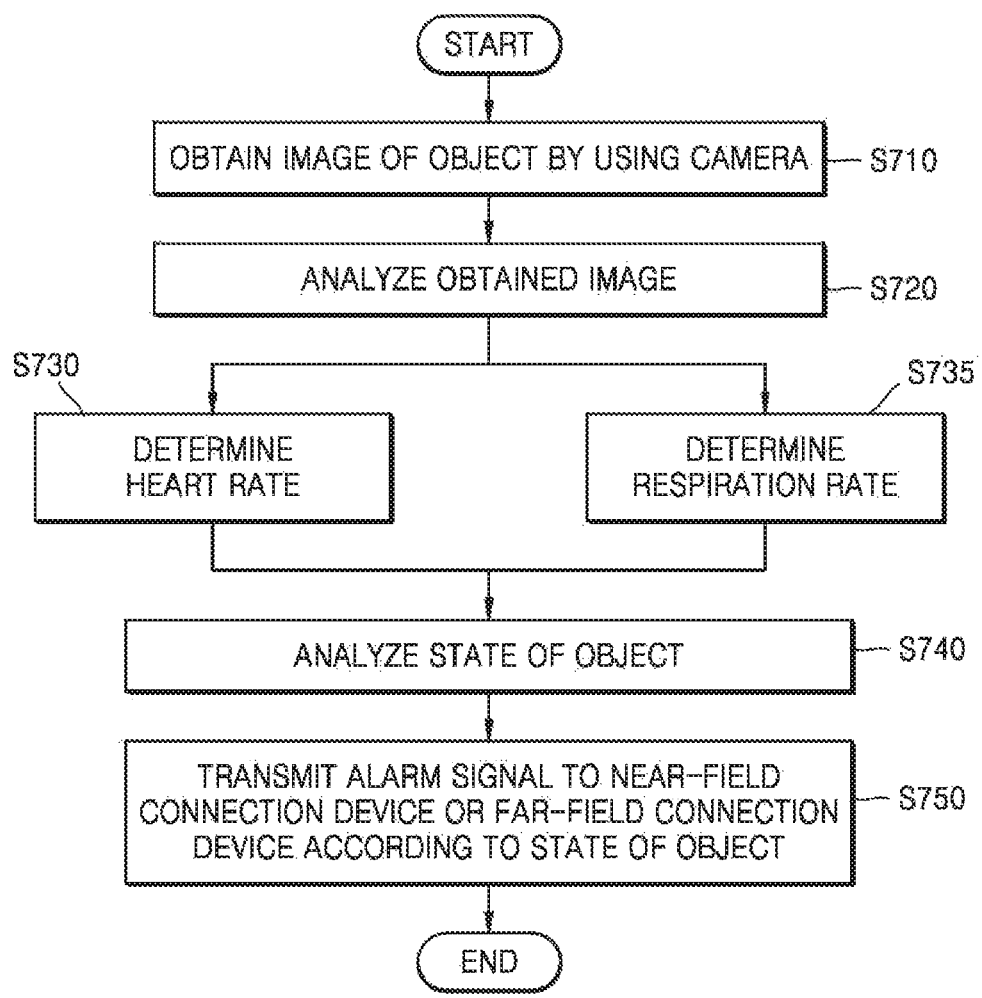
FIG. 7 is a flowchart illustrating a method performed by the display device to determine a heart rate/respiration rate, according to an exemplary embodiment.
Figure 8:
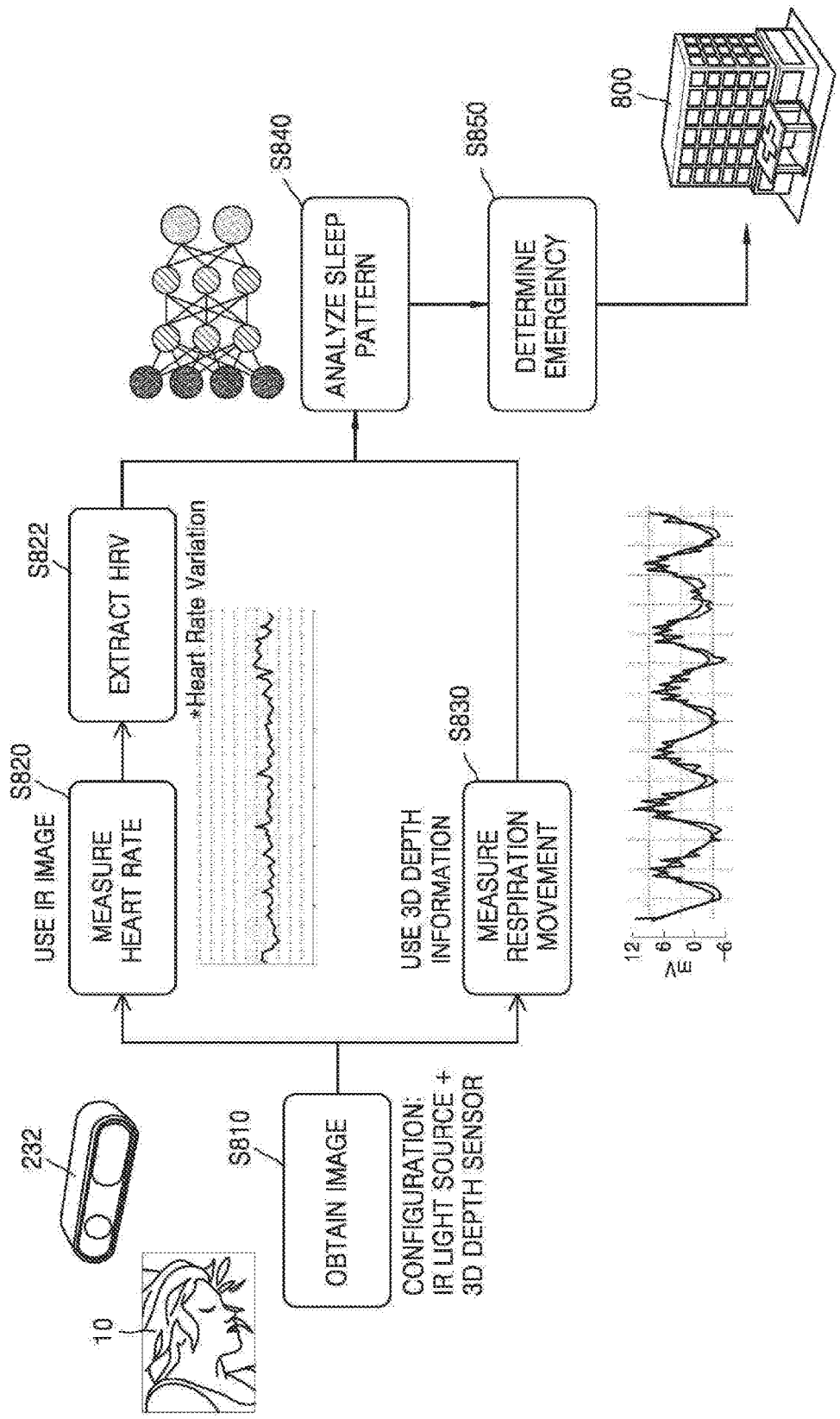
FIG. 8 is a view illustrating a method performed by the display device to determine a heart rate/respiration rate, according to an exemplary embodiment.

FIGS. 6 through 8 will be explained based on the assumption that the apparatus 100 is included in the display device 230. According to an exemplary embodiment, the display device 230 may measure information about a heart rate or a respiration movement of the object 10 based on depth information or an infrared image that is obtained through the camera 232.

FIG. 6 is a view illustrating a system used by the display device 230 to monitor the object 10, according to an exemplary embodiment. An operation performed by the display device 230 to measure the information about the heart rate or the respiration will be explained below in detail with reference to FIGS. 7 and 8.

The display device 230 may calculate a similarity between a current sleep pattern of the object 10 and an abnormal sleep pattern that is stored in the storage 108 by using the information about the heart rate or the respiration movement. If it is determined that the current sleep pattern of the object 10 is an abnormal pattern, the display device 230 may output a message or a voice signal for notifying the object 10 of an emergency, and may transmit a message for notifying a terminal 610 of a family member of the object 10 of the emergency. Also, when there is no additional response to the operation, the display device 230 may automatically notify a server 630 of a closest emergency center or a predetermined medical institute of a state of a patient.

Also, the display device 230 may control devices such as the air conditioner 250, the air cleaner 260, the heater 270, and the lighting device 280 that are connected to a home network in order to control an environment around the object 10 based on the information about the heart rate or the respiration movement. For example, when a sleep depth of the object 10 is low, the display device 230 may further reduce an illuminance of a room by controlling the lighting device 280.

FIG. 7 is a flowchart illustrating a method performed by the display device 230 to determine a heart rate/respiration rate, according to an exemplary embodiment.

In operation S710, the display device 230 may obtain an object image by using the camera 232. For example, the display device 230 may obtain an infrared image or a depth image.

The display device 230 may detect infrared radiation that is radiated from a solid object by using an infrared camera, may change a radiant temperature of the solid object into an electrical signal, and may obtain a two-dimensional (2D) visible image (i.e., an infrared image).

Also, the display device 230 may measure a depth value of the object 10 by using a depth camera, may image the measured depth value, and may generate a depth image.

In operation S720, the display device 230 may analyze the obtained image. In operations S730 and S735, the apparatus 100 may determine a heart rate and a respiration rate based on a result of the analysis of the obtained image.

For example, the display device 230 may measure the heart rate of the object 10 by comparing frames of the infrared image. In particular, the display device 230 may determine the heart rate of the object 10 by comparing feature points or feature vectors around an artery in the infrared image with each other.

Also, the display device 230 may determine the respiration rate by comparing frames of the depth image. For example, since the chest repeatedly expands and contracts as the object 10 breathes, the display device 230 may determine the respiration rate by tracking a change in the chest in the depth image.

According to an exemplary embodiment, the display device 230 may obtain sleep information of the object 10. For example, the display device 230 may obtain information about a snoring pattern of the object 10 by using a microphone. Also, the display device 230 may obtain information about a change in a body temperature of the object 10 by using the infrared image. The display device 230 may obtain information about the amount of emitted sweat, information about how the object 10 turns over during sleep, and information about an EEG of the object 10 from an external sensor.

In operation S740, the display device 230 may analyze a state of the object 10.

According to an exemplary embodiment, the display device 230 may calculate a similarity between a current sleep pattern of the object 10 and an abnormal sleep pattern that is stored in the storage 108. As a result of the calculation, when the similarity between the current sleep pattern of the object 10 and the abnormal sleep pattern that is stored in the storage 108 is high (for example, greater than or equal to 95%), it may be determined that the object 10 is in a bad state.

For example, when the measured heart rate is less than or equal to a minimum critical heart rate or greater than or equal to a maximum critical heart rate, the display device 230 may determine that the heart rate of the object 10 is abnormal. Also, when the respiration rate of the object 10 per minute is less than or equal to a critical value, the display device 230 may determine that the object 10, who is sleeping, is in an apnea state.

In operation S750, the display device 230 may transmit an alarm signal to a near-field connection device or a far-field connection device according to the state of the object 10.

If it is determined that the current sleep pattern of the object 10 is an abnormal sleep pattern, the display device 230 may output a message or a voice signal for notifying the object 10 of an emergency. Also, the display device 230 may transmit a message for notifying the terminal 610 of a family member of the object 10 of the emergency. When there is no response within a predetermined period of time after the message is transmitted to the terminal 610 of the other family member, the display device 230 may automatically notify the server 630 of a closest emergency center or a predetermined medical institute of the state of the object 10. For example, when there is no access of a third person to the object 10 within 5 minutes after the message is transmitted to the terminal 610 of the family member, the display device 230 may transmit an emergency rescue message including the state of the object 10 to the server 630 of the emergency center or the predetermined medical institute.

According to another exemplary embodiment, the display device 230 may transmit the alarm signal to the near-field connection device or the far-field connection device according to a seriousness of the state of the object 10. For example, when the object 10 is in a sleep hypopnea state (e.g., a state where there is a 50% reduction in air flow and a 4% decrease in oxygen saturation that lasts for 10 seconds or longer), the display device 230 may transmit the alarm signal to the near-field connection device. The near-field connection device that is a device located around the display device 230 may transmit/receive a signal using near-field communication with the display device 230. In contrast, when a sleep apnea state of the object 10 lasts for 30 seconds or more, the display device 230 may transmit the alarm signal to the far-field connection device, instead of the near-field connection device. Examples of the far-field connection device may include an emergency center server, a medical institute server, and a designated terminal of a doctor.

FIG. 8 is a view illustrating a method performed by the display device 230 to determine a heart rate/respiration rate, according to an exemplary embodiment.

In operation S810, the display device 230 may obtain an image of the object 10 by using the camera 232. In this case, the camera 230 may be a depth camera. For example, the depth camera may measure a depth value of the object 10 (specifically, the chest). The depth camera may include an IR light source and a three-dimensional (3D) depth sensor.

According to an exemplary embodiment, the depth sensor may obtain the depth value of the object 10 by using various methods. For example, the depth sensor may measure the depth value by using at least one of a time-of-flight (TOF) method, a stereoscopic vision method, and a structured light pattern method.

The TOF method refers to a method of measuring a distance to a solid object by analyzing a time taken for light to be reflected from the solid object and return. In a TOF system, an infrared light-emitting diode (LED) emits infrared light and an infrared camera measures a time taken for light to be reflected from a solid object and return to the infrared camera. The depth sensor may include an infrared LED and an infrared camera. The depth sensor may obtain distance information as a moving image by repeatedly emitting and receiving light, for example, ten or more times per second. Also, the depth sensor may generate a depth map representing distance information by using a brightness or a color of each pixel.

The stereoscopic vision method refers to a method of obtaining a stereoscopic image of a solid object by using two cameras. In this case, the depth sensor may include two cameras. The depth sensor may calculate a distance based on the principle of triangulation by using difference information between images of the two cameras. A person perceives a depth based on a difference between images projected to the right and left eyes, and the depth sensor measures a distance by using a method similar to that of human eyes. For example, when a distance is short, a difference between images obtained by the two cameras is large, and when a distance is long, a difference between images obtained by the two cameras is small.

The structured light pattern method refers to a method of measuring a distance to a solid object by analyzing a position of a pattern that is formed on the solid object. The depth sensor generally projects a linear pattern or a point pattern to a solid object, and the linear pattern or the point pattern varies according to a curve of the solid object.

The structured light pattern method may be performed by replacing one of the two cameras that is used in the stereoscopic vision method with a light projector. For example, the depth sensor may calculate in real time a depth map by analyzing, using an algorithm, a position of a pattern that is formed when light emitted from an infrared projector is projected onto a surface of a solid object.

In operations S820 and S822, the display device 230 may determine a heart rate of the object 10 by using an infrared image.

In operation S830, the display device 230 may measure a respiration movement by using depth information of the object 10. For example, the display device 230 may obtain respiration information (e.g., a respiration rate, a respiration volume, and/or a respiration cycle) of the object 10.

In operation S840, the display device 230 may analyze a sleep pattern of the object 10 based on the heart rate and the respiration information of the object 10.

In operation S850, as a result of the analysis of the sleep pattern, when it is determined that the sleep pattern of the object 10 is abnormal, the display device 230 may determine that the object 10 is in an emergency, and may make a call or transmit a message to a predetermined hospital server 800.

Operations S810 through S850 respectively correspond to operations S710 through S750 of FIG. 7.

Although the display device 230 obtains the heart rate information and the respiration information by using the camera 232 in FIGS. 6 through 8, one or more exemplary embodiments are not limited thereto. For example, a smart watch or a separate sensor may obtain the heart rate information or the respiration information.

Figure 9:
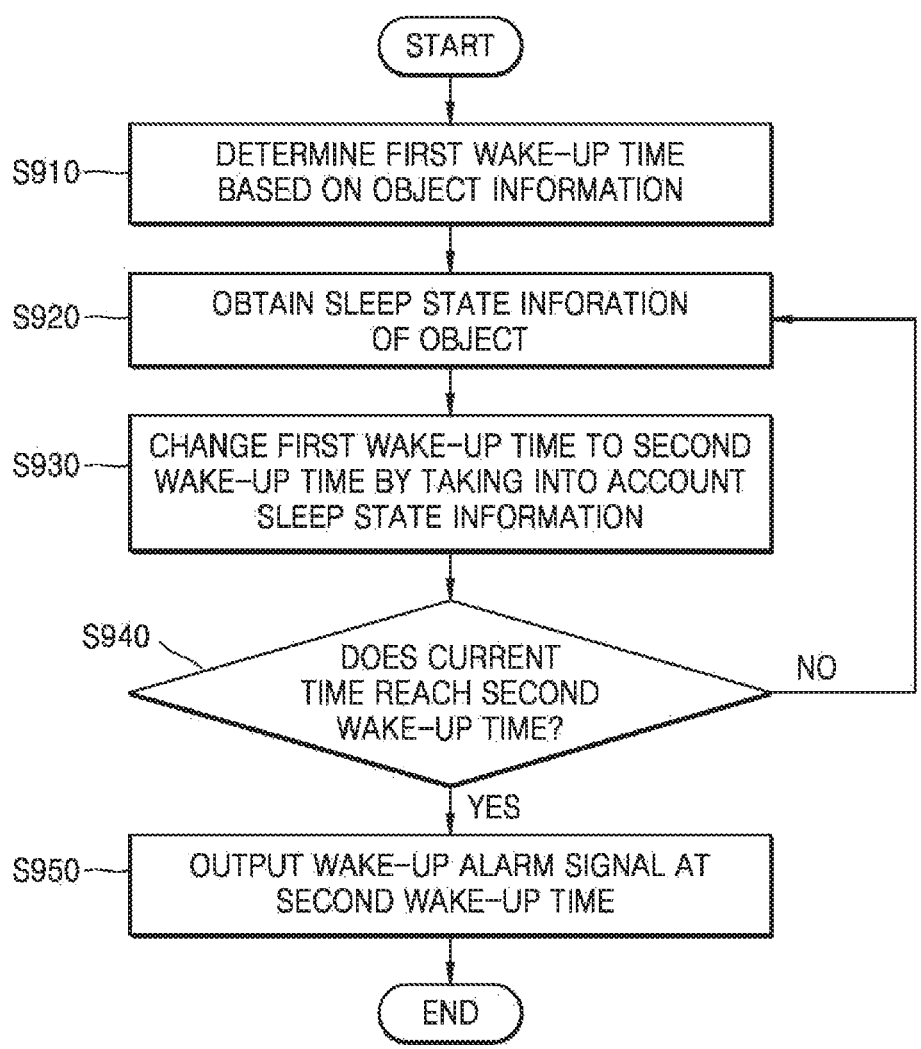
FIG. 9 is a flowchart illustrating a method performed by the apparatus to adjust a wake-up time, according to an exemplary embodiment.

FIG. 9 is a flowchart illustrating a method performed by the apparatus 100 to adjust a wake-up time, according to an exemplary embodiment.

In operation S910, the apparatus 100 may determine a first wake-up time of the object 10. The term 'wake-up time' used herein may be a time at which a wake-up alarm signal is transmitted to the object 10. Also, the object 10 may refer to a person who is sleeping.

According to an exemplary embodiment, the first wake-up time may be a fixed value or a variable value. For example, the first wake-up time may be an average wake-up time of the object 10, or a target wake-up time that is designated by the object 10.

According to an exemplary embodiment, the apparatus 100 may determine the first wake-up time of the object 10 based on object information. According to an exemplary embodiment, the object information may include at least one of average wake-up time information (e.g., 7 AM), wake-up time information before going to sleep (e.g., 6 AM), bedtime information (e.g., 10 PM), schedule information before going to sleep (e.g., dining out, night work, tennis for 1 hour, and swim for 30 minutes), blood alcohol level information before going to sleep (e.g., 0.02%), body temperature information before going to sleep (e.g., 36.5° C.), heart rate information before going to sleep (e.g., 70 times/minute), identification information (e.g., a gender, an age, a height, and a weight), and health care history information (e.g., a blood pressure, a blood sugar level, and a cancer treatment history) of the object 10.

For example, when a blood alcohol level of the object 10 before going to sleep is higher than or equal to 0.03%, the apparatus 100 may determine 7:10 that is 10 minutes later than the average wake-up time (e.g., 7 AM) as the first wake-up time. Also, when the object 10 swims before going to sleep, the apparatus 100 may determine 7:30, which is an average wake-up time the day after the object 10 swam, as the first wake-up time.

In operation S920, the apparatus 100 may obtain sleep state information of the object 10 who is sleeping. The sleep state information that is information related to a sleep of the object 10 may include, as non-limiting examples, bio-information of the object 10 who is sleeping, environment information around the object 10 who is sleeping, and analysis information obtained by analyzing the bio-information of the object 10. For example, the sleep state information may include, as non-limiting examples, at least one of heart rate information, respiration information, movement information (e.g., the number of times the object 10 changes his/her posture during sleep), snoring pattern information, iris movement information, EEG information, emitted sweat information, blood pressure information, blood sugar level information, oxygen saturation information ($SpO_2$), and body temperature information of the object 10.

According to an exemplary embodiment, the apparatus 100 may obtain the bio-information from the wearable terminal 220. For example, the apparatus 100 may obtain pulse information, body temperature information, and/or blood pressure information of the object 10 who is sleeping from a smart band or a smart watch. Also, the apparatus 100 may receive body temperature information and/or emitted sweat information from sleep socks. The apparatus 100 may receive respiration information, pulse information, body temperature information, and/or blood pressure information from a sensor system (e.g., the sensor 105) that is located under a mattress. According to an exemplary embodiment, the sensor system may be of a sheet type including at least two sensors.

According to an exemplary embodiment, the apparatus 100 may obtain sleep state information by analyzing the bio-information of the object 10 that is received from the wearable terminal 220 that is an external terminal. The apparatus 100 may receive from the wearable terminal 220 sleep pattern information of the object 10 that is obtained by analyzing the bio-information received from the wearable terminal 220.

According to an exemplary embodiment, the apparatus 100 may receive environment information around the object 10 who is sleeping from IoT devices.

The IoT device may store service information related to a service that is provided by the IoT device. For example, the IoT device may include a space (e.g., a memory or a disk) in which sensor data that is collected by the sensor or user use history data is stored.

According to an exemplary embodiment, the apparatus 100 may obtain temperature information and/or humidity information from the air conditioner 250. The apparatus 100 may receive fine dust concentration information, humidity information, and/or temperature information from the air cleaner 260.

According to an exemplary embodiment, the apparatus 100 may obtain an image of the object 10 from the camera 232 (e.g., a depth camera or an infrared camera) that is included in the display device 230 (e.g., a TV). In this case, the image of the object 10 may be a still image or a moving image. The apparatus 100 may analyze the image of the object 10, and may obtain heart rate information or respiration information (e.g., a respiration rate, a respiration cycle, or a respiration volume) of the object 10. For example, the apparatus 100 may receive infrared image information of the object 10 from the display device 230. The apparatus 100 may obtain the heart rate information of the object 10 based on the infrared image information.

Also, since the chest repeatedly expands and contracts as the object 10 breathes, the apparatus 100 may obtain the respiration information of the object 10 by comparing feature vectors that are included in a plurality of frames with each other.

In operation S930, the apparatus 100 may change the first wake-up time to a second wake-up time by taking into account the sleep state information of the object 10.

For example, when the number of times the object 10 changes a posture is greater than or equal to a critical number of times (e.g., 30 times), the apparatus 100 may change a target wake-up time from 7 AM to 7:10 AM Also, when the number of times the object 10 changes a posture is greater than or equal to the critical number of times (e.g., 30 times), an apnea cycle of the object 10 is twice or more longer than an average apnea cycle, and a body temperature is higher than or equal to 38° C., the apparatus 100 may adjust the target wake-up time from 7 AM to 7:30 AM According to an exemplary embodiment, the first wake-up time and the second wake-up time may be earlier than a critical time. The critical time may be preset by the object 10 or may be preset by an external device. For example, when the object 10 has to wake up by 8 AM at the latest, the object 10 may set the critical time to 8 AM. Also, when a mobile phone of the object 10 analyzes a time for work of the object 10 and determines that the object 10 usually leaves home before 8:10 AM, the mobile phone may set the critical time to 8 AM in the apparatus 100.

According to an exemplary embodiment, the apparatus 100 may delay or advance the target wake-up time according to a sleep state of the object 10, before or by the critical time.

In operation S940, the apparatus 100 may compare a current time with the second wake-up time and may determine whether the current time reaches the second wake-up time.

When the current time does not reach the second wake-up time, the apparatus 100 may again obtain the sleep state information of the object 10. For example, the apparatus 100 may monitor the sleep state of the object 10 by using at least one of the bio-information of the object 10 that is received from the wearable terminal 220 or a sensor that is embedded in the apparatus 100, the environment information that is received from the IoT device, and the image information of the object 10 that is received from the camera 232.

In operation S950, the apparatus 100 may output a wake-up alarm signal at the second wake-up time. The wake-up alarm signal may be a signal for inducing a wake-up of the object 10. For example, the wake-up alarm signal may include, as non-limiting examples, at least one of an audio signal, a video signal, a vibration signal, a smell signal, and a touch signal. According to an exemplary embodiment, the apparatus 100 may output the wake-up alarm signal by using a vibration motor, a display, e.g., a display unit, or a speaker that is included in the apparatus 100.

According to an exemplary embodiment, the apparatus 100 may output the wake-up alarm signal at the second wake-up time through an external device. For example, the apparatus 100 may output the wake-up alarm signal through a display device (e.g., a TV) or an alarm clock.

Also, the apparatus 100 may open a window through the window controller 270, may change an illuminance or a color in a room by using the lighting device 280, or may output a preset sound through the audio output device 240. Also, the apparatus 100 may activate a fan of the air conditioner 250, or may move an air cell or a mechanical frame of a bed.

According to an exemplary embodiment, the apparatus 100 may set an optimum wake-up time according to the sleep state of the object 10 by monitoring the sleep state of the object 10. Also, the apparatus 100 may output the wake-up alarm signal so that the object 10 may wake up at a time at which the object 10 has the best condition.

According to an exemplary embodiment, when a plurality of objects are in a bed, the apparatus 100 may adjust wake-up times according to the plurality of objects. For example, a target wake-up time before going to sleep of each of a first object and a second object may be 7:30 AM In this case, when an apnea cycle of the first object who is sleeping is twice or more longer than a usual apnea cycle, the apparatus 100 may adjust the target wake-up time of the first object from 7:30 AM to 8 AM When it is 7:30 AM, the apparatus 100 may output a second wake-up alarm signal corresponding to the second object, and when it is 8 AM, the apparatus 100 may output a first wake-up alarm signal corresponding to the first object. The second wake-up alarm signal and the first wake-up alarm signal may be different signals in which preferences of the second object and the first object are respectively reflected. For example, the first wake-up alarm signal and the second wake-up alarm signal may be signals for outputting different songs. Alternatively, the first wake-up alarm signal may be a signal for making a vibration from a smart watch that is worn on a wrist of the first object, and the second wake-up alarm signal may be a signal for outputting radio news from an audio output device of the second object.

According to an exemplary embodiment, the apparatus 100 may measure an actual wake-up time of the object 10, the apparatus 100 may determine a remaining time (e.g., 30 minutes) from the actual wake-up time (e.g., 7:30 AM) of the object 10 to a preset critical time (e.g., 8 AM). The apparatus 100 may select at least one activity to be performed by the object 10 for the remaining time. The apparatus 100 may provide information about the selected at least one activity.

For example, it is assumed that the object 10 wakes up at 7 AM, leaves home at 8 AM, and needs a preparation time of 1 hour before going to work. When the object 10 wakes up at 7:30 AM, the apparatus 100 may determine that there is only a remaining time of 30 minutes. In this case, the apparatus 100 may transmit to the object 10 information indicating that taking a shower, washing hair, and eating breakfast, from among things generally done during the preparation time before going to work, should be omitted. Also, the apparatus 100 may transmit to the object 10 schedule information indicating that only washing face, shaving, getting dressed, packing bag, and drinking milk, from among the things generally done during the preparation time before going to work, should be performed. According to an exemplary embodiment, as the remaining time decreases, the number of things selected by the apparatus 100 may decrease.

According to an exemplary embodiment, the apparatus 100 may display information about the selected at least one schedule on an external display device (e.g., a TV).

Although the apparatus 100 changes the target wake-up time of the object 10 in FIG. 9, one or more exemplary embodiments are not limited thereto. According to an exemplary embodiment, a server that is connected to the apparatus 100 may obtain the sleep pattern information of the object 10 through the apparatus 100 and may change the target wake-up time based on the sleep pattern information. The server may also transmit information about the changed target wake-up time to the apparatus 100.

Figure 10:
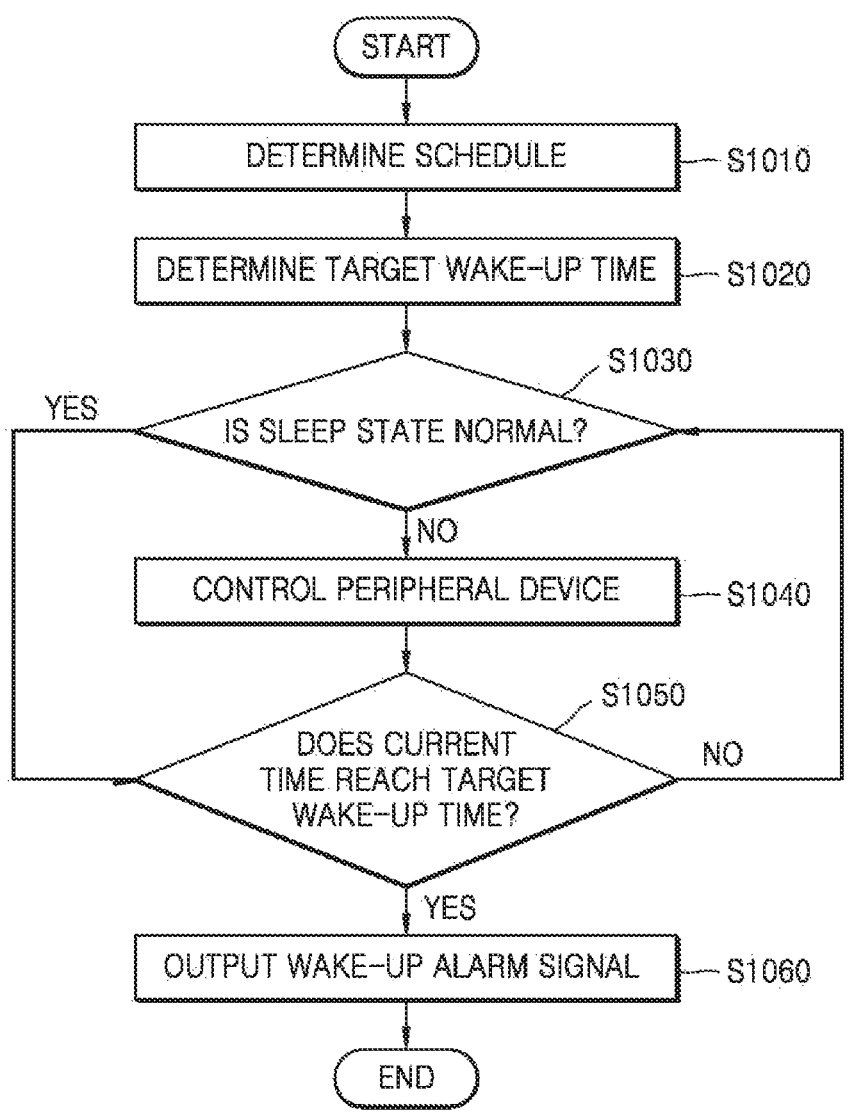
FIG. 10 is a flowchart illustrating a method performed by the apparatus to control a peripheral device according to a sleep state of the object, according to an exemplary embodiment.

FIG. 10 is a flowchart illustrating a method performed by the apparatus 100 to control a peripheral device according to a sleep state of the object 10, according to an exemplary embodiment.

In operation S1010, the apparatus 100 may determine a schedule of the object 10. For example, the apparatus 100 may determine whether the object 10 exercised before going to sleep, whether the object 10 drank alcohol before going to sleep, or whether the object 10 drank coffee in a coffee shop before going to sleep, based on schedule information recorded by the object 10, context information (e.g., position information) of the object 10, or bio-information of the object 10. Also, the apparatus 100 may determine a next day's schedule of the object 10. For example, the apparatus 100 may determine whether the object 10 has a meeting in the morning, has a business trip in the morning, or has a day-off.

In operation S1020, the apparatus 100 may determine a target wake-up time based on the schedule before going to sleep or the next day's schedule of the object 10. For example, when the object 10 rode a bicycle before going to sleep, the apparatus 100 may determine 7:30 AM, which is 30 minutes later than a usual wake-up time, as the target wake-up time. Also, when the object 10 rode a bicycle before going to sleep but there is a meeting at 8 AM the next day, the apparatus 100 may determine 7 AM as the target wake-up time.

In operation S1030, the apparatus 100 may determine a sleep state of the object 10. For example, the apparatus 100 may determine whether the sleep state of the object 10 is normal by using the bio-information of the object 10 and/or environment information (e.g., a temperature, humidity, luminance, or noise in a room) around the object 10. If it is determined that the sleep state of the object 10 is normal, the method proceeds to operation S1050. In operation S1050, the apparatus 100 may determine whether a current time reaches the target wake-up time.

If it is determined in operation S1030 that the sleep state of the object 10 is not normal, the method proceeds to operation S1040. In operation S1040, the apparatus 100 may control a peripheral device in order to improve the sleep quality of the object 10. For example, the apparatus 100 may adjust a temperature in a bedroom by using the air conditioner 250 or may adjust humidity in the bedroom by using a dehumidifier. Also, the apparatus 100 may change an illuminance or a color in the bedroom by using the lighting device 280. When an apnea time of the object 10 is greater than or equal to a critical value (e.g., 20 seconds), the apparatus 100 may wake up the object 10 by outputting a sound.

In operation S1050, the apparatus 100 may determine whether the current time reaches the target wake-up time. If it is determined in operation S1050 that the current time does not reach the target wake-up time, the method returns to operation S1030. In operation S1030, the apparatus 100 may monitor again the sleep state of the object 10 to further monitor the sleep state of the object 10.

If it is determined in operation S1050 that the current time reaches the target wake-up time, the method proceeds to operation S1060. In operation S1060, the apparatus 100 may output a wake-up alarm signal. For example, the wake-up alarm signal may include, as non-limiting examples, at least one of an audio signal, a video signal, a vibration signal, a smell signal, and a touch signal. According to an exemplary embodiment, the apparatus 100 may output the wake-up alarm signal by using a vibration motor, a display, or a speaker that is included in the apparatus 100. Also, the apparatus 100 may wake up the object 10 by spraying a specific air freshener or water preferred by the object 10.

According to an exemplary embodiment, the apparatus 100 may output the wake-up alarm signal at the target wake-up time through an external device. For example, the apparatus 100 may output the wake-up alarm signal (e.g., may display an alarm image or may output an alarm sound) through the display device 230 (e.g., a TV), the portable terminal 210, the wearable terminal 220, or an alarm clock. Also, the apparatus 100 may open a window through the window controller 270, may change an illuminance or a color in a room by using the lighting device 280, or may output a preset sound through the audio output device 240. Also, the apparatus 100 may cause wind to blow through the air conditioner 250 or may move an air cell and a mechanical frame of a bed.

Figure 11:
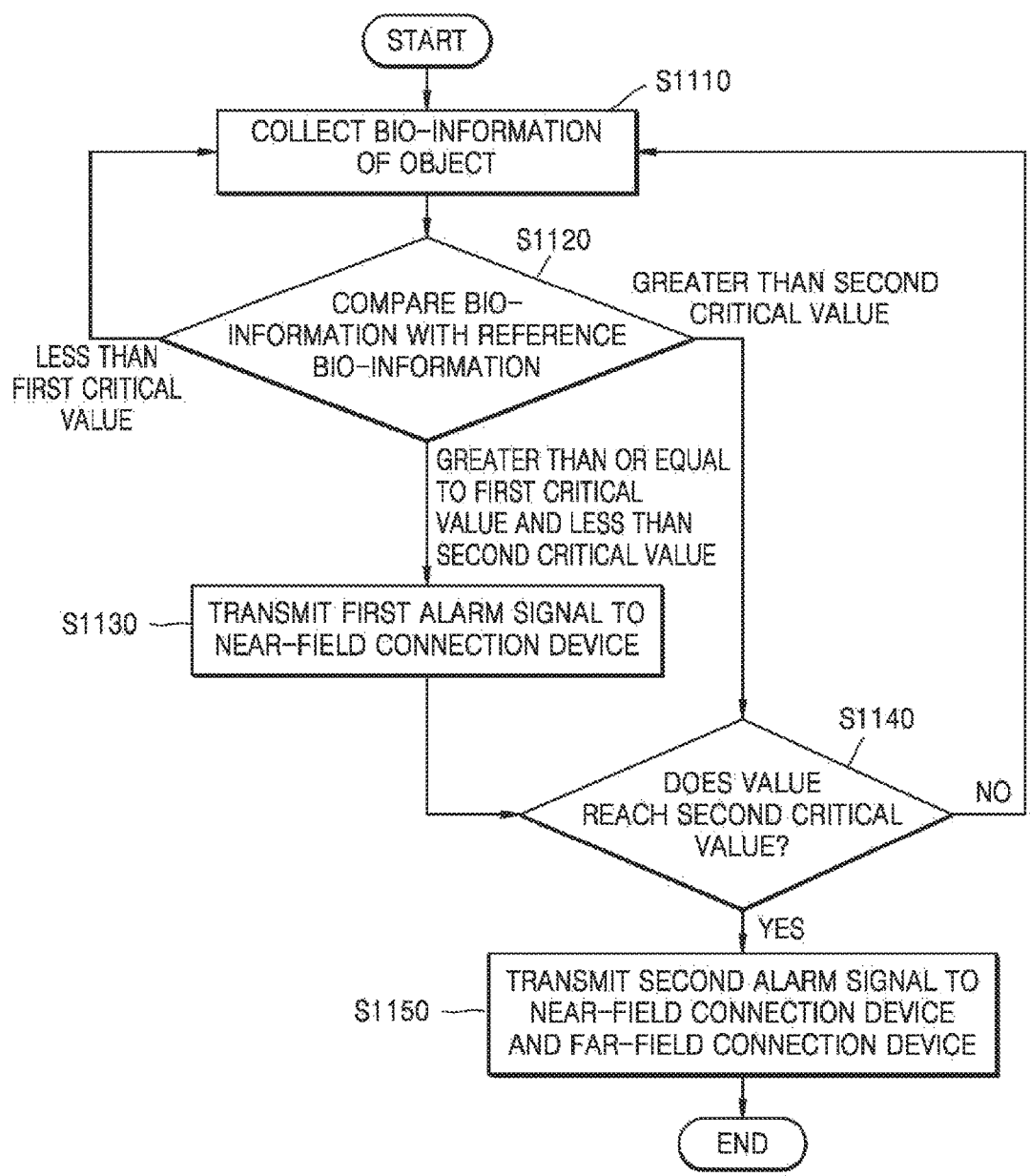
FIG. 11 is a flowchart illustrating a method of monitoring the object who is sleeping, according to an exemplary embodiment.

FIG. 11 is a flowchart illustrating a method of monitoring the object 10 who is sleeping, according to an exemplary embodiment.

In operation S1110, the apparatus 100 may obtain (or collect) bio-information of the object 10 who is sleeping.

In operation S1120, the apparatus 100 may compare the obtained bio-information with reference bio-information. According to an exemplary embodiment, the reference bio-information may include a critical value that is set based on a clinical test. According to an exemplary embodiment, the reference bio-information may include a critical value that is set based on personal measurement information of the object 10. According to an exemplary embodiment, the reference bio-information may vary according to an age, a gender, and a body size of the object 10.

According to an exemplary embodiment, the reference bio-information may include, as non-limiting examples, at least one of a reference temperature value, a reference respiration rate value, a reference signal saturation value, and a reference apnea cycle value. According to an exemplary embodiment, the reference bio-information may include a plurality of critical values.

If it is determined in operation S1120 that a value that is included in the obtained bio-information is greater than a first critical value and is less than a second critical value, wherein the first and second critical values are included in the reference bio-information, the method proceeds to operation S1130. In operation S1130, the apparatus 100 may transmit a first alarm signal related to the obtained bio-information to near-field connection devices. The near-field connection devices may be devices that are located in a near-field communication zone of the apparatus 100.

According to an exemplary embodiment, the apparatus 100 may select at least one near-field connection device for adjusting the value that is included in the obtained bio-information. The apparatus 100 may transmit a control signal for controlling a predetermined function to the selected at least one near-field connection device. For example, when a body temperature of the object 10 is higher than or equal to 38° C., the apparatus 100 may select the air conditioner 250, the ventilator 290, and the window controller 270 to reduce the body temperature of the object 10. The apparatus 100 may transmit a control signal for reducing a set temperature to the air conditioner 250, may transmit a control signal for increasing a rotation speed to the ventilator 290, and a control signal for opening a window to the window controller 270.

In operation S1140, the apparatus 100 may determine whether the value that is included in the obtained bio-information reaches the second critical value that is included in the reference bio-information. The second critical value may be a value indicating that the object 10 is in a worse state than that of the first critical value. For example, the first critical value may be a 'body temperature of 38° C.' and the second critical value may be a 'body temperature of 40° C.'.

If it is determined in operation S1140 that the value that is included in the obtained bio-information is greater than or equal to the second critical value, the method proceeds to operation S1150. In operation S1150, the apparatus 100 may transmit a second alarm signal related to the obtained bio-information to a far-field connection device. In this case, the apparatus 100 may also transmit the second alarm signal related to the obtained bio-information to the near-field connection device. The far-field connection device may include a medical institute server or a designated terminal of a doctor.

According to an exemplary embodiment, the apparatus 100 may receive diagnosis information and guide information from the far-field connection device in response to the second alarm signal. For example, the apparatus 100 may receive information about a device for diagnosing the object 10 or a drug for emergency treatment from the far-field connection device.

According to one exemplary embodiment, when the value that is included in the obtained bio-information is greater than or equal to the second critical value, the apparatus 100 may obtain an image of the object 10 by using the camera 232. For example, when a body temperature of the object 10 is higher than or equal to 40° C., the apparatus 100 may capture an image of the object 10 by controlling the camera 232. In this case, the image of the object 10 may be a still image or a moving image.

The apparatus 100 may transmit the obtained image of the object 10 to the far-field connection device. According to an exemplary embodiment, the apparatus 100 may prevent a private life of the object 10 from being continuously exposed by activating the camera 232 only when it is determined that the object 10 is in an emergency and transmitting the image of the object 10 to an external server. Also, the apparatus 100 may reduce power consumed by the camera 232.

According to an exemplary embodiment, when the object 10 is in a normal state, the apparatus 100 may use the image of the object 10 that is obtained through the camera 232 to analyze a sleep pattern of the object 10, but may not store the image of the object 10 in a memory. However, when it is determined that the object 10 is in an emergency, the apparatus 100 may store the image that is obtained through the camera 232 and may transmit the image to the external server.

According to an exemplary embodiment, the apparatus 100 may periodically transmit the image of the object 10 to the external server.

According to an exemplary embodiment, when the value that is included in the obtained bio-information is greater than the first critical value and is less than the second critical value, the apparatus 100 may transmit the first alarm signal related to the obtained bio-information to the near-field connection device. When a response signal to the first alarm signal is not received from the near-field connection device for a predetermined period of time, the apparatus 100 may transmit the second alarm signal related to the obtained bio-information to the far-field connection device.

Figure 12:
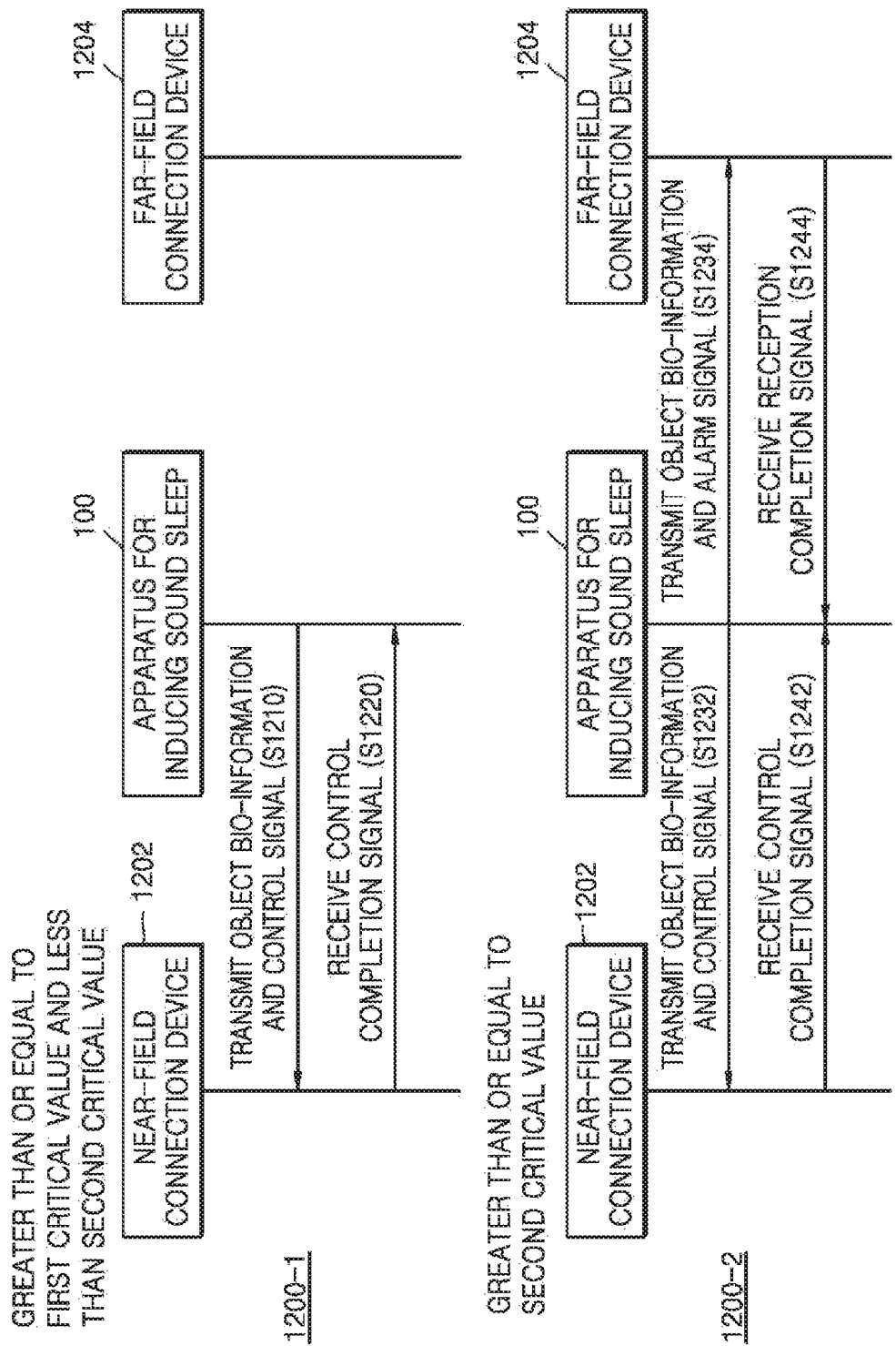
FIG. 12 is a timing diagram illustrating a method performed by the apparatus to communicate with at least one of a near-field connection device and a far-field connection device, according to an exemplary embodiment.

FIG. 12 is a timing diagram illustrating a method performed by the apparatus 100 to communicate with at least one of a near-field connection device and a far-field connection device, according to an exemplary embodiment.

1200-1 of FIG. 12 is a case where a value that is included in obtained bio-information of the object 10 is greater than a first critical value and is less than a second critical value that are included in reference bio-information.

In operation S1210, when the value that is included in the obtained bio-information is greater than the first critical value and is less than the second critical value that are included in the reference bio-information, the apparatus 100 may transmit the bio-information of the object 10 and a control signal to a near-field connection device 1202.

In operation S1220, the apparatus 100 may receive a control completion signal from the near-field connection device 1202. In this case, the apparatus 100 may not transmit the bio-information of the object 10 to a far-field connection device 1204.

1200-2 of FIG. 12 is a case where the value that is included in the obtained bio-information of the object 10 is greater than the second critical value that is included in the reference bio-information.

In operation S1232, the apparatus 100 may transmit the bio-information of the object 10 and the control signal to the near-field connection device 1202. In operation S1234, the apparatus 100 may transmit the bio-information of the object 10 and an alarm signal to the far-field connection device 1204. For example, since the value that is included in the bio-information of the object 10 is greater than the second critical value, the apparatus 100 may determine that the object 10 is in a bad state and may transmit the alarm signal indicating a state of the object 10 and the bio-information of the object 10 to the far-field connection device 1204 as well as the near-field connection device 1202.

In operation S1242, the apparatus 100 may receive a control completion signal from the near-field connection device 1202. In operation S1244, the apparatus 100 may receive a reception completion signal from the far-field connection device 1204.

A method performed by the apparatus 100 to improve the sleep quality of the object 10 by monitoring a sleep state of the object 10 and an ambient environment will now be explained.

Figure 13:
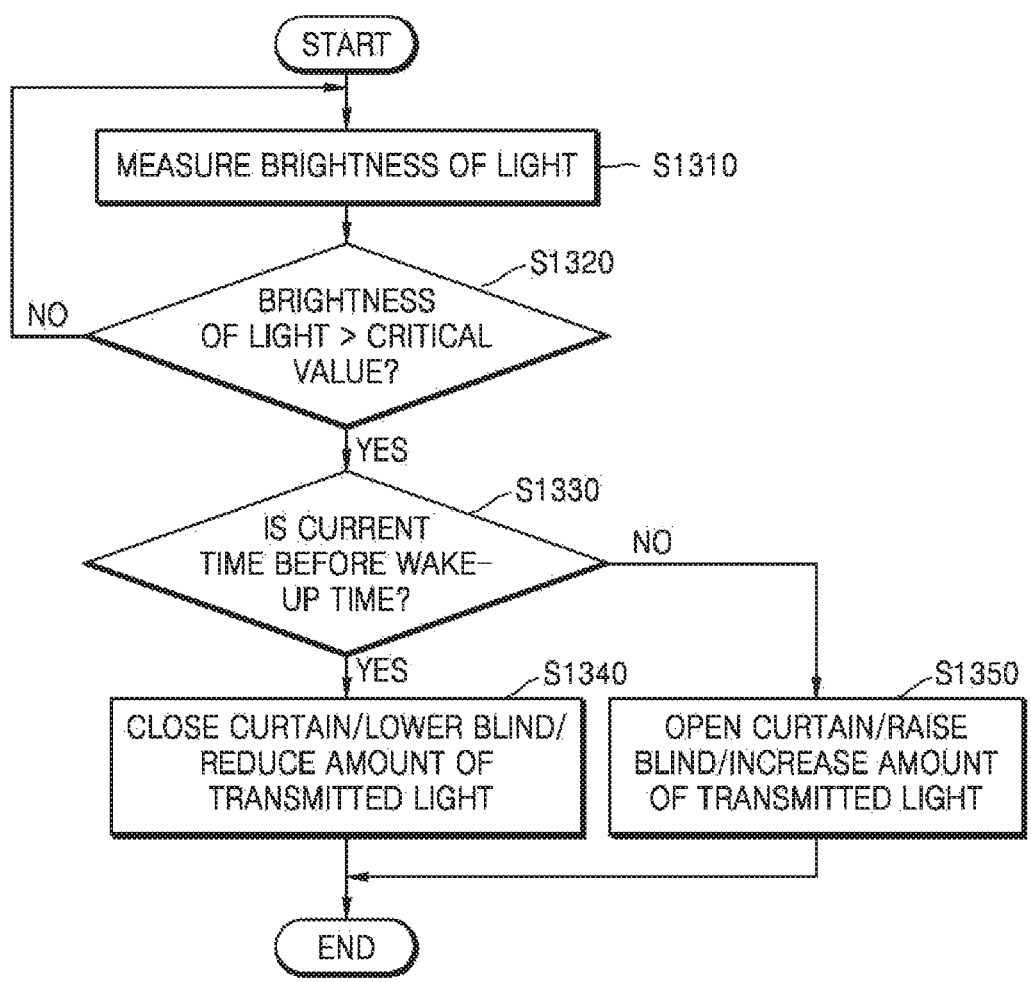
FIG. 13 is a flowchart illustrating a method of adjusting a curtain or a blind according to a brightness of light, according to an exemplary embodiment.

FIG. 13 is a flowchart illustrating a method of adjusting a curtain or a blind according to a brightness of light, according to an exemplary embodiment.

In operation S1310, the apparatus 100 may measure a brightness of light around the object 10 who is sleeping. For example, the apparatus 100 may measure a brightness of light by using an illumination sensor (e.g., an RGB sensor) in a bedroom.

The apparatus 100 may continuously or periodically measure a brightness of light by using the illumination sensor. Also, the apparatus 100 may activate the illumination sensor only for a specific period of time. For example, the apparatus 100 may measure a brightness of light by activating the illumination sensor only from 5 AM to 8 PM.

In operation S1320, the apparatus 100 may determine whether the measured brightness of light is greater than a preset critical value. The critical value may be set by the object 10 or may be preset in the apparatus 100.

For example, the critical value may be 30 lux. Although each person has his/her own favorite brightness in a bedroom, according to a study on a relationship between a brightness and sleep quality, when a brightness is greater than or equal to 30 lux, sleep quality may be bad, and when a brightness is greater than or equal to 100 lux, a sleep depth may be reduced.

When the brightness of light is less than the critical value (e.g., 30 lux) and thus the bedroom is still dark, the apparatus 100 may continuously or periodically measure the brightness of light by using the illumination sensor.

If it is determined in operation S1320 that the brightness of light is greater than or equal to the critical value (e.g., 30 lux), the method proceeds to operation S1330. In operation S1330, the apparatus 100 may determine whether a current time is before or after a wake-up time at which the object 10 is to be woken up. The wake-up time at which the object 10 has to wake up may be a fixed time (e.g., 7 AM) that is selected by the object 10 or may be a time (e.g., a time that is determined from 7 AM to 8 AM) that varies according to a sleep state (e.g., a sleep depth, a sleep duration, and sleep quality) of the object 10.

For example, when a target wake-up time that is determined according to the sleep state of the object 10 is 8 AM and a current time is 6:30 AM, the apparatus 100 may determine that the current time is 'before' the wake-up time. In contrast, when a target wake-up time that is set by the object 10 is 6 AM and a current time is 6:03 AM, the apparatus 100 may determine that the current time is 'after' the wake-up time.

If it is determined in operation S1330 that the current time is 'before' the wake-up time, the method proceeds to operation S1340. In operation S1340, the apparatus 100 may close a curtain by controlling the curtain. Alternatively, the apparatus 100 may lower a blind or may reduce the amount of transmitted light by controlling the blind. In this case, the brightness of the bedroom may be reduced.

Accordingly, according to an exemplary embodiment, when the sun rises before the wake-up time at which the object 10 has to wake up or the object 10 is napping, the apparatus 100 may reduce an illuminance in the bedroom in order to improve the sleep quality of the object 10.

If it is determined in operation S1330 that the current time is 'after' the wake-up time, the method proceeds to operation S1350. In operation S1350, the apparatus 100 may open the curtain by controlling the curtain. Alternatively, the apparatus 100 may raise the blind or may increase the amount of transmitted light by controlling the blind. In this case, the bedroom may get brighter.

Accordingly, according to an exemplary embodiment, when the object 10 still sleeps even after the wake-up time, the apparatus 100 may rapidly wake up the object 10 by increasing an illuminance in the bedroom.

FIG. 14 is illustrates a method performed by the apparatus 100 to control a curtain according to a brightness of light in a bedroom, according to an exemplary embodiment.

In a case 1400-1, a current time may be 6 AM and a target wake-up time that is set in an alarm clock 1420 may be 8 AM. In this case, when the apparatus 100 measures a brightness of light at 6 AM by using an illumination sensor, the brightness in the bedroom may be 50 lux because the sun has risen.

Since the measured brightness in the bedroom (50 lux) is greater than a critical brightness value (30 lux) and the current time (6 AM) is before the target wake-up time (8 AM), the apparatus 100 may reduce an illuminance in order to improve the sleep quality of the object 10.

In a case 1400-2, the apparatus 100 may automatically close a curtain 1410 by manipulating a curtain controller. The apparatus 100 may maintain a state where the curtain 1410 is closed until the target wake-up time (8 AM).

When time passes and the current time is 8 AM, the alarm clock 1420 may output a wake-up alarm sound in order to wake up the object 10. In this case, since the current time (8 AM) reaches the target wake-up time (8 AM), the apparatus 100 may open the curtain 1410 and may wake up the object 10.

An operation performed by the apparatus 100 to remove noise around the object 10 in order to improve the sleep quality of the object 10 will now be explained in detail with reference to FIG. 15.

Figure 15:
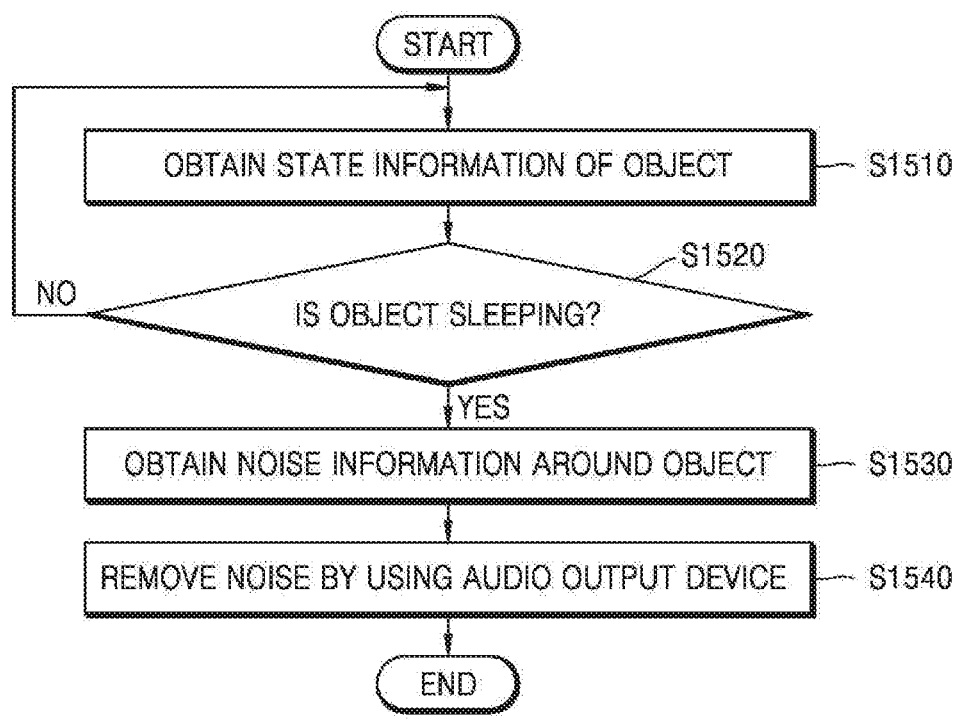
FIG. 15 is a flowchart illustrating a method of removing noise around the object by using an audio output device, according to an exemplary embodiment.

FIG. 15 is a flowchart illustrating a method of removing noise around the object 10 by using an audio output device, according to an exemplary embodiment.

In operation S1510, the apparatus 100 may obtain state information of the object 10.

For example, the apparatus 100 may collect information sensed by the sensor 105 or an external IoT device, and may analyze a state of the object 10 based on the collected information. Also, the apparatus 100 may receive from the external IoT device information about the state of the object 10 that is analyzed by the external IoT device.

Examples of the state of the object 10 may include, but are not limited to, a state in which the object 10 is walking, a state in which the object 10 is stopping, a state in which the object 10 is running, a state in which the object 10 is sleeping, a state in which the object 10 is driving, a state in which the object 10 is going to work, a state in which the object 10 is talking (or having a conversation), a state in which the object 10 is exercising (e.g., jogging, swimming, playing tennis, playing basketball, or going mountain climbing), a state in which the object 10 is drinking liquor, a state in which the object 10 stands, a state in which the object 10 sits, and a state in which the object 10 lies.

According to an exemplary embodiment, the apparatus 100 may determine whether the object 10 is stopping, walking, or running by using at least one of an acceleration sensor, a tilt sensor, a position sensor, and a pressure sensor. For example, when it is found by using acceleration information that is measured by the acceleration sensor that the object 10 moves at an average speed of 0.001 km/h for a predetermined period of time (1), the apparatus 100 may determine that the object 10 is stopping, when it is found that the object 10 moves at an average speed of 4 km/h for the predetermined period of time (2), the apparatus 100 may determine that the object 10 is walking, and when it is found that the object 10 moves at an average speed of 15 km/h for the predetermined period of time, the apparatus 100 may determine that the object 10 is running.

In operation S1520, the apparatus 100 may determine whether the object 10 is sleeping, based on the state information of the object 10.

According to an exemplary embodiment, the apparatus 100 may determine whether the object 10 is sleeping by using at least one of an iris recognition sensor, an image sensor, a microphone, an acceleration sensor, and a tilt sensor. For example, when a state where a movement value of the object 10 that is measured by a motion sensor (e.g., an acceleration sensor, a tilt sensor, or a geomagnetic sensor) is less than or equal to a critical value is maintained for a predetermined period of time, the apparatus 100 may determine that the object 10 is sleeping.

When a value of a pressure sensor that is embedded in a pillow or a mattress is greater than or equal to a critical value and a respiration pattern of the object 10 is a respiration pattern during sleep, the apparatus 100 may determine that the object 10 is sleeping. Also, when a sound signal that is obtained through a microphone is analyzed and a sound of a snoring pattern is detected, the apparatus 100 may determine that the object 10 is sleeping.

When the number of times eyes of the object 10 blink which is measured through an iris recognition sensor that is attached to an eye patch is less than a critical number of times (e.g., one eye blinking is detected for 10 minutes) or an iris is not detected for a predetermined period of time (e.g., 5 minutes or longer), the apparatus 100 may determine that the object 10 is sleeping.

According to an exemplary embodiment, the apparatus 100 may capture an image of an eye of the object 10 in predetermined cycles by using an image sensor (e.g., the camera 232), and may detect a pupil by performing edge analysis on the captured image of the eye. In this case, when the pupil is not detected in the captured image of the eye for a predetermined period of time (e.g., 5 minutes or longer), the apparatus 100 may determine that the object 10 is sleeping.

There may be various other methods performed by the apparatus 100 to determine whether the object 10 is sleeping.

If it is determined in operation S1520 that the object 10 is sleeping, the method proceeds to operation S1530. In operation S1530, the apparatus 100 may obtain noise information around the object 10.

According to an exemplary embodiment, the apparatus 100 may receive a noise signal within a predetermined distance from the object 10 through the audio input device (e.g., a microphone). The audio input device may be included in the apparatus 100 or may be included in an external device. Also, since the audio input device is a device for measuring noise around the object 10, the audio input device may be located within a predetermined distance (e.g., 30 cm) from the object 10.

According to an exemplary embodiment, the apparatus 100 may determine a noise pattern having periodic characteristics by analyzing the noise signal. The noise pattern may refer to a signal of a unit interval (e.g., a sample interval) that periodically repeats in the noise signal.

For example, when a noise signal having a periodic noise pattern is generated in an external device such as a refrigerator, a clock, or a humidifier, the apparatus 100 may determine a noise pattern by analyzing the noise signal.

According to an exemplary embodiment, the apparatus 100 may receive the noise information from the outside. For example, the apparatus 100 may receive from an external device cycle information of a noise signal that is generated in the external device. In this case, the external device may obtain the cycle information of the noise signal by analyzing the noise signal through a microphone that is included in the external device.

The apparatus 100 may determine a noise pattern of the noise signal that is input through the audio input device by using the cycle information of the noise signal that is received from the external device.

In operation S1540, the apparatus 100 may remove noise by using an audio output device.

According to an exemplary embodiment, the apparatus 100 may reduce the noise signal by using an active noise cancellation or active noise control (ANC) technology. ANC reduces ambient noise by generating a first noise whose phase is opposite to that of a second noise that is input through a microphone and combining the first noise with the second noise.

According to an exemplary embodiment, the apparatus 100 may generate an anti-phase noise pattern having a phase that is opposite to that of the ambient noise pattern that is determined in operation S1530. The apparatus 100 may continuously output the anti-phase noise pattern through the audio output device (e.g., a speaker). In this case, the noise signal around the object 10 may be reduced due to the anti-phase noise pattern.

According to an exemplary embodiment, the apparatus 100 may synchronize a first cycle in which a noise pattern is repeated in the noise signal with a second cycle in which the anti-phase noise pattern is output. When the first cycle and the second cycle are not synchronized with each other, since noise may not be reduced and may be amplified, the apparatus 100 may increase a reduction in the noise signal by synchronizing the first cycle with the second cycle.

According to an exemplary embodiment, the apparatus 100 may output an anti-phase noise pattern through a plurality of audio output devices.

According to an exemplary embodiment, the apparatus 100 may remove only noise that is generated in a specific device (e.g., a device designated by the object 10). For example, the apparatus 100 may select a first noise pattern that is related to the specific device from among a plurality of noise patterns by using cycle information of a noise signal that is received from the specific device. The apparatus 100 may output a first anti-phase noise pattern having a phase that is opposite to that of the selected first noise pattern through the audio output device (e.g., a speaker).

For example, when the object 10 is insensitive to a sound of a refrigerator and is sensitive to a sound of an hour hand of a clock, the apparatus 100 may not reduce a noise signal that is generated by the refrigerator and may reduce only a noise signal that is generated by the short hand of the clock by using periodic characteristics of a noise pattern of the short hand of the clock.

According to an exemplary embodiment, the audio input device and the audio output device may be embedded in one device or may be disposed as separate devices. Also, according to an exemplary embodiment, the apparatus 100 may reduce noise by using the audio input device and the audio output device that are located in the apparatus 100, and may reduce noise by using the audio input device and the audio output device that are included in the external device. For example, the apparatus 100 may reduce the noise signal around the object 10 by using a smartphone or a TV including the audio/output devices.

An operation performed by the apparatus 100 to remove noise around the object 10 who is sleeping will now be explained in more detail with reference to FIGS. 16 through 19.

FIG. 16 is a graph illustrating a triggered spectral subtraction method using periodic characteristics of a noise pattern, according to an exemplary embodiment.

In operation S1610, the apparatus 100 may determine a noise pattern 1600 of a noise signal 1610 by calculating a cycle value of the noise signal 1610 that is input through a microphone or receiving cycle information from a device that generates noise.

In operation S1620, the apparatus 100 may cancel the noise signal 1610 by outputting an anti-phase noise pattern having a phase that is opposite to that of the noise pattern 1600. In this case, the apparatus 100 may synchronize a cycle in which the noise pattern 1600 repeats with a cycle in which the anti-phase noise pattern is output, and may continuously output the anti-phase noise pattern.

Figure 17:
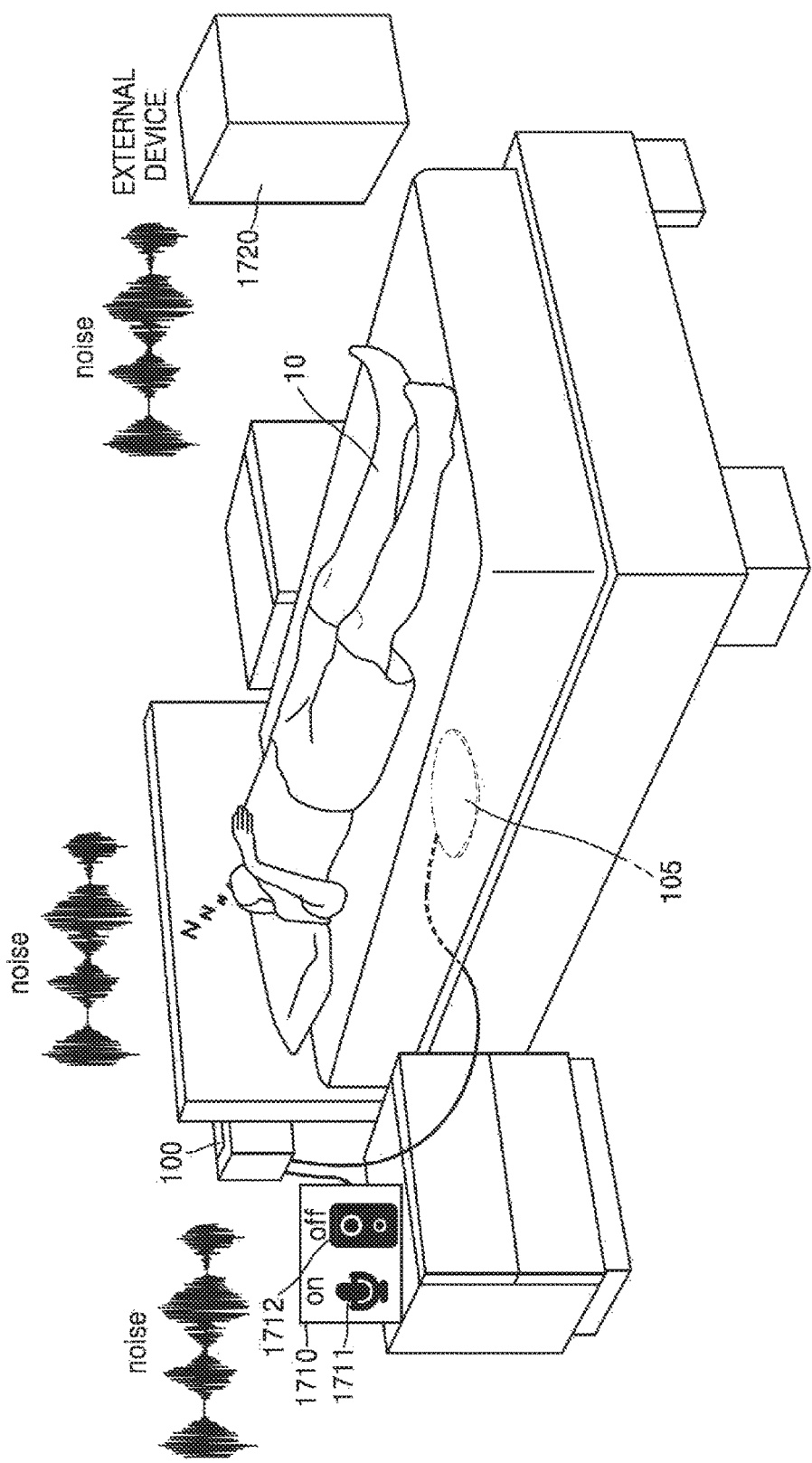
FIGS. 17 and 18 are views illustrating an example where the apparatus removes noise around the object by using an audio output device, according to an exemplary embodiment.
Figure 18:
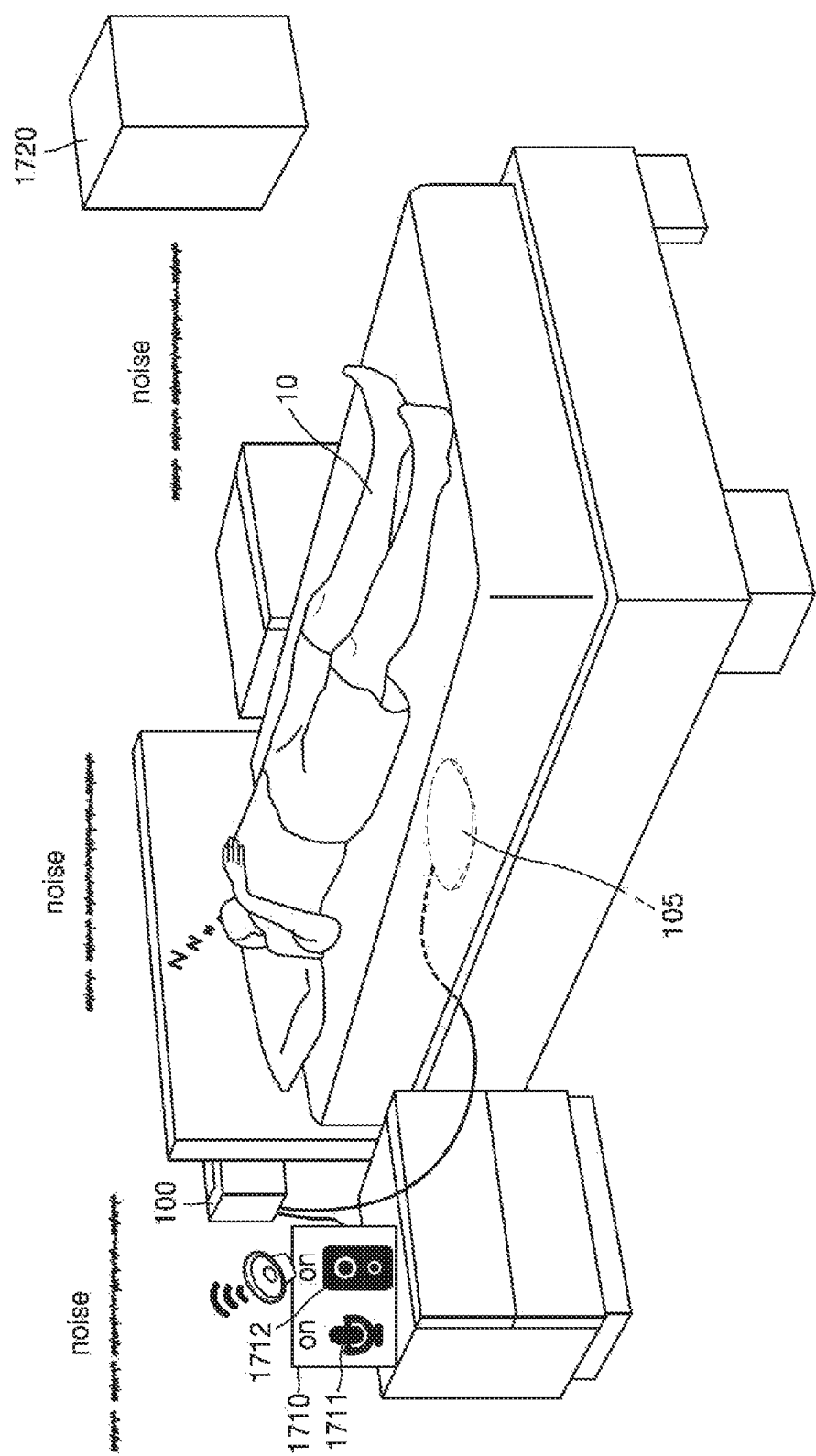

FIGS. 17 and 18 are views illustrating an example where the apparatus 100 removes noise around the object 10 by using an audio output device, according to an exemplary embodiment.

Referring to FIG. 17, the apparatus 100 may recognize that the object 10 is sleeping based on information that is received through the sensor 105. In this case, when a value of a noise signal that is generated in an external device 1720 is greater than or equal to a critical value, the noise signal may disturb the object 10 who is sleeping. Accordingly, the apparatus 100 may analyze the noise signal that is generated in the external device 1720 and is input through an audio input device 1711.

The apparatus 100 may use a microphone that is included in a device 1710 such as a smartphone, a tablet PC, or a TV as the audio input device 1711. In this case, the smartphone, the tablet PC, or the TV may be connected in a wired or wireless manner to the apparatus 100.

The external device 1720 may be located around the object 10 who is sleeping and may generate periodic noise. Examples of the external device 1720 may include, but are not limited to, a clock, a refrigerator, a humidifier, an air conditioner, a washing machine, and a computer.

When it is found, as a result of the analysis of the noise signal, that a value of the noise signal that is generated in the external device 1720 is greater than or equal to a critical value, the apparatus 100 may reduce the noise signal that is generated in the external device 1720 based on an ANC technology in order to improve the sleep quality of the object 10.

Referring to FIG. 18, the apparatus 100 may determine a noise pattern of the noise signal that is generated in the external device 1720 and may output an anti-phase noise pattern through an audio output device 1712. The apparatus 100 may use a speaker that is included in the device 1710 such as a smartphone, a tablet PC, or a TV as the audio output device 1712.

According to an exemplary embodiment, noise around the object 10 may be reduced due to the anti-phase noise pattern that is output through the audio output device 1712. Accordingly, the sleep quality of the object 10 may be improved.

Figure 19:
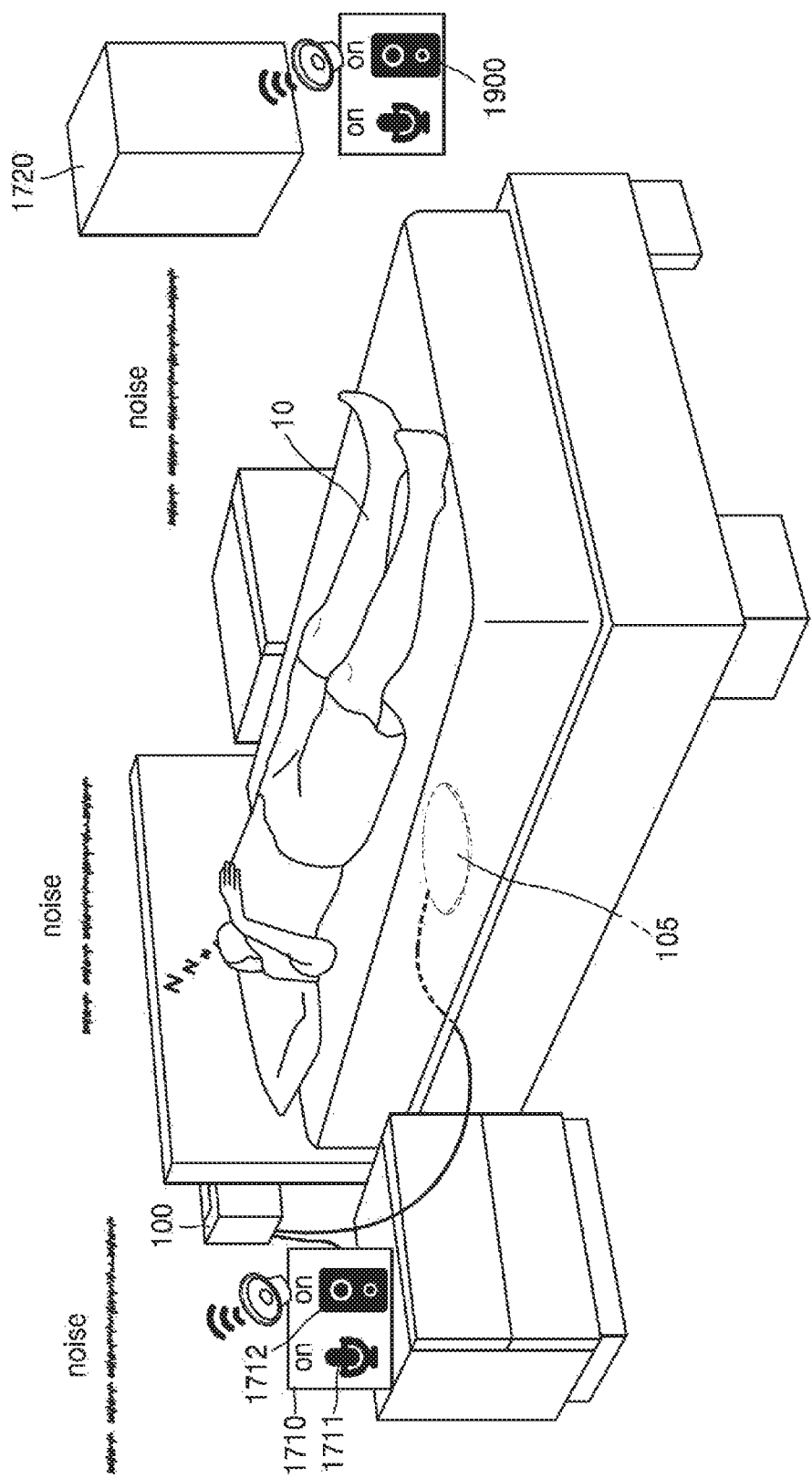
FIG. 19 is a view illustrating an example where the apparatus uses a plurality of audio output devices, according to an exemplary embodiment.

FIG. 19 is a view illustrating an example where the apparatus 100 uses a plurality of audio output devices, according to an exemplary embodiment.

Referring to FIG. 19, the apparatus 100 may output an anti-phase noise pattern through a plurality of audio output devices. For example, the apparatus 100 may output an anti-phase noise pattern through the audio output device 1712 that is located around the object 10 who is sleeping and, at the same time, may further output an anti-phase noise pattern through a second audio output device 1900 that is located around the external device 1720. In this case, a reduction in a noise signal that is generated in the external device 1720 may be increased.

Although not shown in FIG. 19, an anti-phase noise pattern may not be output from the audio output device 1712 that is located around the object 10, and an anti-phase noise pattern may be output only from the second audio output device 1900 that is located around the external device 1720. Further, anti-phase noise patterns may be output through three or more audio output devices.

A method of reducing power consumption of the audio output device 1712 that reduces a noise signal will now be explained.

Figure 20:
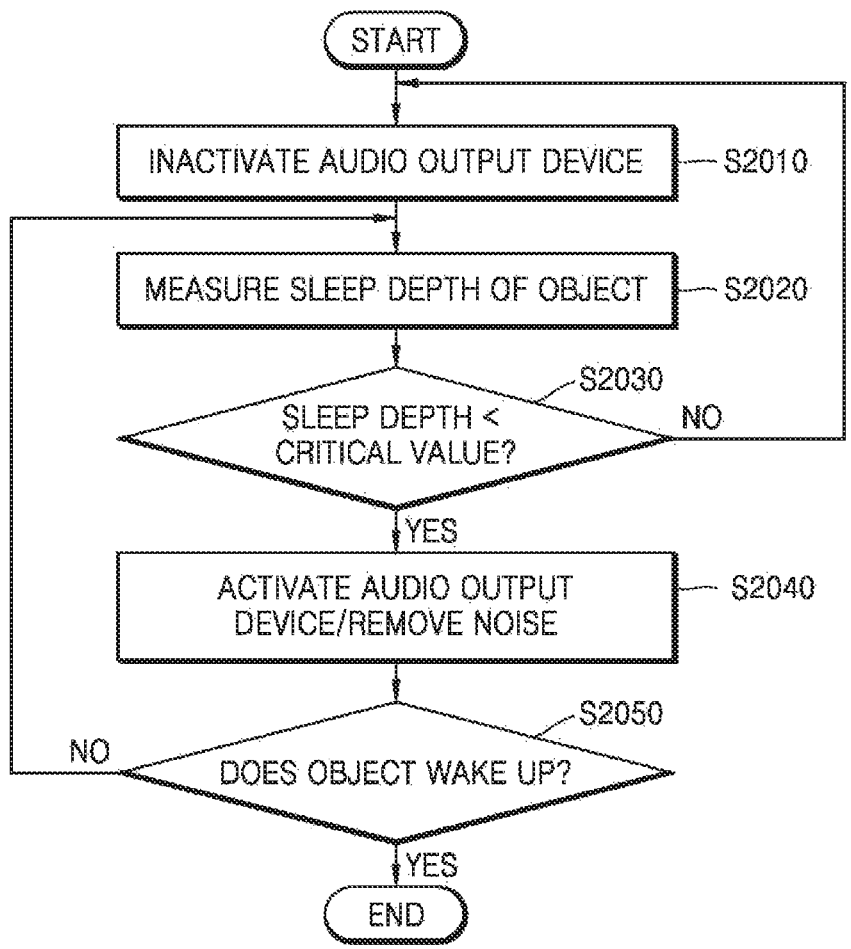
FIG. 20 is a flowchart illustrating a method of removing noise according to a sleep depth of the object, according to an exemplary embodiment.

FIG. 20 is a flowchart illustrating a method of removing noise according to a sleep depth of the object 10, according to an exemplary embodiment.

In operation S2010, the apparatus 100 may inactivate an audio output device in order to reduce stand-by power consumption. For example, when the object 10 is not in a room or a sound is not reproduced through the audio output device, the apparatus 100 may maintain the audio output device in an inactive state.

In operation S2020, the apparatus 100 may recognize that the object 10 is sleeping and may measure a sleep depth of the object 10.

According to an exemplary embodiment, the apparatus 100 may analyze a movement during sleep of the object 10 and may measure the sleep depth based on a result of the analysis. For example, the apparatus 100 may receive movement information of the object 10 through a motion sensor that is located in a pillow or a mattress or on a wrist of the object 10. In this case, when a movement value of the object 10 that is detected by the motion sensor is greater than or equal to a first critical value, the apparatus 100 may determine that a sleep depth level of the object 10 is at a first level. Also, when the movement value of the object 10 is between the first critical value and a second critical value, the apparatus 100 may determine the sleep depth level of the object 10 is at a second level, and when the movement value of the object 10 is less than the second critical value, the apparatus 100 may determine that the sleep depth level of the object 10 is at third level.

According to an exemplary embodiment, the apparatus 100 may measure the sleep depth by using EEG information that is obtained through an EEG sensor. For example, the apparatus 100 may determine whether the object 10 is in a rapid eye movement (REM) sleep state or a non-rapid eye movement (NREM) sleep state by using the EEG information. Also, when the object 10 is in the REM sleep state, the apparatus 100 may determine that the sleep depth of the object 10 is low and when the object 10 is in the NREM sleep state, the apparatus 100 may determine that the sleep depth of the object 10 is high.

In operation S2030, the apparatus 100 may determine whether the sleep depth of the object 10 is less than a critical value. Also, the apparatus 100 may classify levels of the sleep depth of the object 10 according to a preset standard.

According to an exemplary embodiment, if it is determined in operation S2030 that the sleep depth of the object 10 is greater than the critical value, the method returns to operation S2010 in which the apparatus 100 may maintain the audio output device in the inactive state in order to reduce power consumption. For example, when the object 10 sleeps deeply, since a sound sleep of the object 10 is not greatly affected by noise around the object 10, the apparatus 100 may maintain the audio output device in the inactive state and may not output an anti-phase noise signal.

If it is determined in operation S2030 that the sleep depth of the object 10 is less than the critical value, the method proceeds to operation S2040. In operation S2040, the apparatus 100 may activate the audio output device and may reduce noise by using the activated audio output device.

According to an exemplary embodiment, the apparatus 100 may reduce a noise signal by using an ANC technology.

Operation S2030 corresponds to operation S1540 of FIG. 15.

In operation S2040, the apparatus 100 may determine whether the object 10 wakes up. When the object 10 does not wake up, the method returns to operation S2020 in which the apparatus 100 may measure again the sleep depth of the object 10. When the sleep depth is measured to be greater than the critical value, the apparatus 100 may inactivate the activated audio output device. Also, when the sleep depth of the object 10 is less than the critical value, the apparatus 100 may maintain the audio output device in an active state and may continuously remove noise.

An operation performed by the apparatus 100 to control noise according to a sleep depth of the object 10 will be further explained with reference to FIG. 21.

Figure 21:
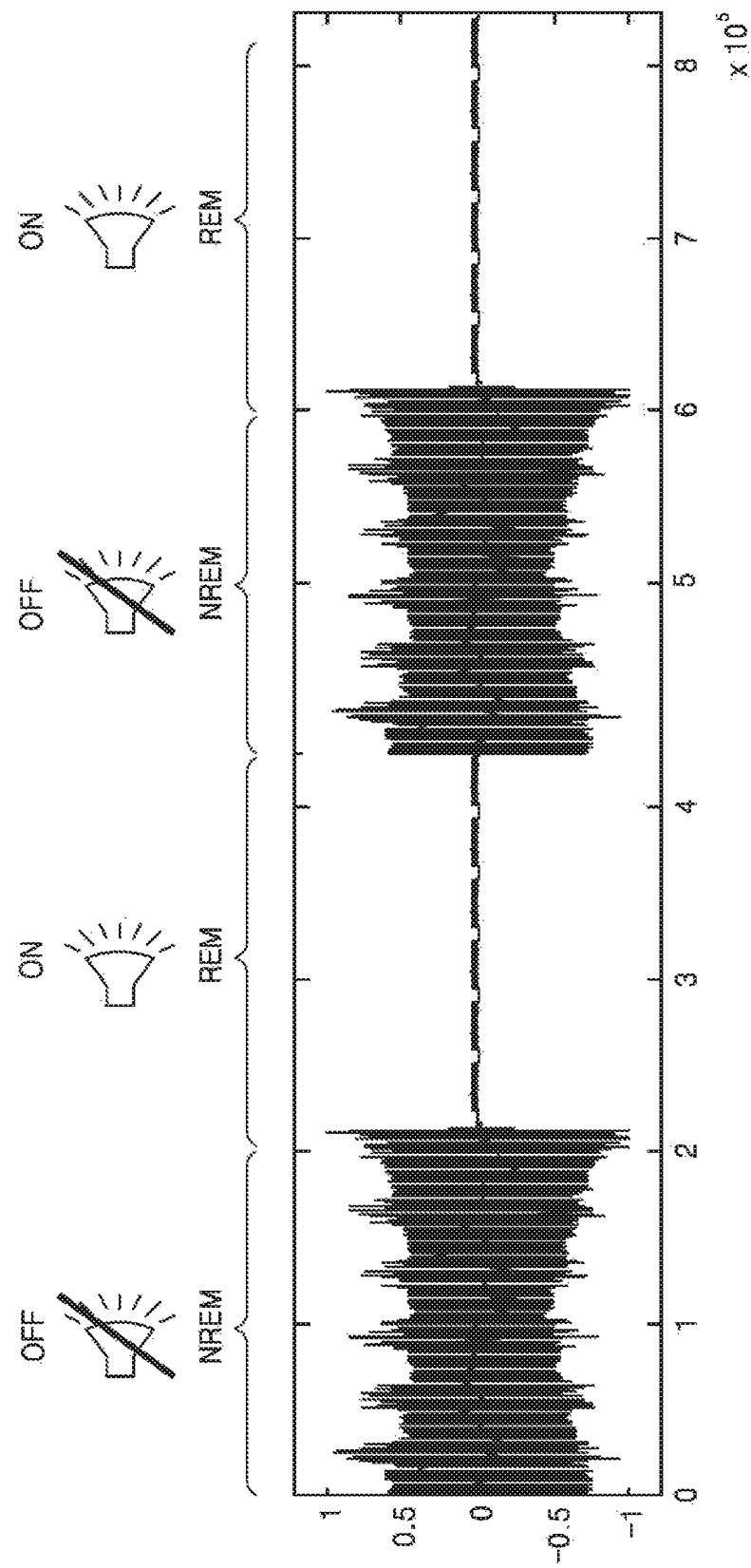
FIG. 21 is a graph illustrating an example where the apparatus determines whether to activate an audio output device according to a sleep depth of the object, according to an exemplary embodiment.

FIG. 21 is a graph illustrating an example where the apparatus 100 determines whether to activate an audio output device according to a sleep depth or cycle of the object 10, according to an exemplary embodiment.

The apparatus 100 may measure a sleep depth of the object 10, and may determine whether to activate the audio output device and whether to output an anti-phase noise pattern according to the measured sleep depth. For example, when the sleep state of the object 10 is a deep sleep state, the apparatus 100 may inactivate the audio output device and may not output the anti-phase noise pattern, and when the sleep state of the object 10 is a shallow sleep state, the apparatus 100 may activate the audio output device and may output the anti-phase noise pattern.

As shown in FIG. 21, since the audio output device is inactivated and the anti-phase noise signal is not output in a NREM sleep interval in which the object 10 is in a deep sleep state, noise around the object 10 may not be reduced. In contrast, since the audio output device is activated and the anti-phase noise signal is output through the audio output device in a REM sleep interval, noise around the object 10 may be reduced.

According to an exemplary embodiment, an output intensity of the anti-phase noise pattern may be adjusted according to the sleep depth of the object 10. For example, when the object 10 is in a deep sleep state, since the object 10 is not greatly affected by noise, the apparatus 100 may reduce the output intensity of the anti-phase noise pattern and may reduce a noise reduction. Also, when the object 10 is in a shallow sleep state, since the object 10, who is sleeping, is disturbed by noise, the apparatus 100 may increase the output intensity of the anti-phase noise pattern and may increase the noise reduction. For example, when the object 10 is in a deep sleep state, the apparatus 100 may adjust the noise reduction to be about 50%, and, when the object 10 is in a shallow sleep state, the apparatus 100 may adjust the noise reduction to be about 99%. As the noise reduction increases, it may be more quite around the object 10.

An example where an alarm condition is adjusted according to a sleep depth of the object 10 will now be explained with reference to FIG. 22.

Figure 22:
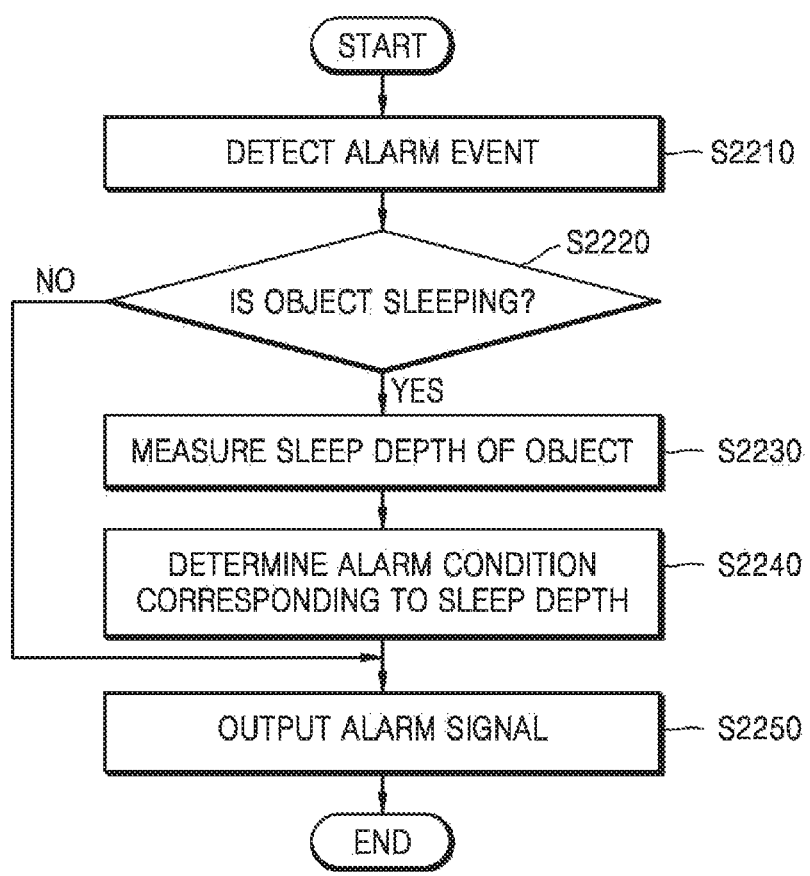
FIG. 22 is a flowchart illustrating a method of adjusting an alarm condition according to a sleep depth of the object, according to an exemplary embodiment.

FIG. 22 is a flowchart illustrating a method of adjusting an alarm condition according to a sleep depth of the object 10, according to an exemplary embodiment.

In operation S2210, the apparatus 100 may detect an alarm event.

The alarm event may refer to an event in which information that has to be notified to the object 10 is generated. The alarm event may be an event for notifying a situation that occurs inside the apparatus 100 or an event for notifying a situation that occurs outside the apparatus 100. Examples of the alarm event may include, but are not limited to, a scheduled alarm event, a wake-up alarm event, a charge request alarm event, a message reception alarm event, an update alarm event, a recommended content alarm event, a health information alarm event, an emergency alarm event, a traffic information alarm event, and an advertising alarm event.

For example, when the apparatus 100 receives an alarm message from an external device using near-field communication, the apparatus 100 may detect that an event for outputting the alarm message occurs.

In operation S2220, when the alarm event occurs, the apparatus 100 may determine whether the object 10 is sleeping.

According to an exemplary embodiment, the apparatus 100 may determine whether the object 10 is sleeping by using, for example, at least one of an iris recognition sensor, an image sensor, a microphone, an acceleration sensor, and a tilt sensor. For example, the apparatus 100 may determine that the object 10 is sleeping when a state where a movement value of the object 10 that is measured by a motion sensor (e.g., an acceleration sensor, a tilt sensor, or a geomagnetic sensor) is less than or equal to a critical value is maintained for a predetermined period of time.

When a value of a pressure sensor that is embedded in a pillow or a mattress is greater than or equal to a critical value and a respiration pattern of the object 10 is a respiration pattern during sleep, the apparatus 100 may determine that the object 10 is sleeping. Also, the apparatus 100 may analyze a sound signal that is obtained through a microphone, and when a sound of a snoring pattern is detected, may determine that the object 10 is sleeping.

When the number of times eyes of the object 10 blink, which is measured through an iris recognition sensor attached to an eye patch, is less than a critical number of times (e.g., one eye blinking is detected for 10 minutes) or an iris is not detected for a predetermined period of time (e.g., 5 minutes), the apparatus 100 may determine that the object 10 is sleeping.

According to an exemplary embodiment, the apparatus 100 may capture an image of an eye of the object 10 in predetermined cycles by using an image sensor (e.g., the camera 232), and may detect a pupil by performing edge analysis on the captured image of the eye. In this case, when the pupil is not detected in the captured image of the eye for a predetermined period of time (e.g., 5 minutes or longer), the apparatus 100 may determine that the object 10 is sleeping.

According to an exemplary embodiment, when it is not determined in operation S2220 that the object 10 is sleeping, the method proceeds to operation S2250. In operation S2250, the apparatus 100 may output an alarm signal related to the alarm event by using a predetermined alarm condition. For example, when a message is received from the external device, the apparatus 100 may output an alarm sound indicating that the message is received and may directly display the received message on a display.

If it is determined in operation S2220 that the object 10 is sleeping, the method proceeds to operation S2230. In operation S2230, the apparatus 100 may measure a sleep depth of the object 10.

According to an exemplary embodiment, the apparatus 100 may analyze a movement of the object 10 during sleep and may measure the sleep depth based on a result of the analysis. For example, the apparatus 100 may receive movement information of the object 10 through a motion sensor that is located in the pillow or the mattress or on a wrist of the object 10. In this case, when a movement value of the object 10 that is detected by the motion sensor is greater than or equal to a first critical value, the apparatus 100 may determine that a sleep depth level of the object 10 is at a first level. Also, when the movement value of the object 10 is between the first critical value and a second critical value, the apparatus 100 may determine that the sleep depth level of the object 10 is at a second level, and when the movement value of the object 10 is less than the second critical value, the apparatus 100 may determine that the sleep depth level of the object 10 is at a third level.

According to an exemplary embodiment, the apparatus 100 may measure the sleep depth by using EEG information that is obtained through an EEG sensor. For example, the apparatus 100 may determine whether the object 10 is in a REM sleep state or a NREM sleep state by using the EEG information. Also, when the object 10 is in the REM sleep state, the apparatus 100 may determine that the sleep depth of the object 10 is low and when the object 10 is in the NREM sleep state, the apparatus 100 may determine that the sleep depth of the object 10 is high.

In operation S2240, the apparatus 100 may determine an alarm condition corresponding to the sleep depth of the object 10. In operation S2250, the apparatus 100 may output an alarm signal related to the alarm event by using the determined alarm condition.

According to an exemplary embodiment, the apparatus 100 may adjust an output intensity of the alarm signal according to the sleep depth of the object 10. For example, as the sleep depth of the object 10 decreases, the object 10 easily responds to an external environment. Accordingly, the apparatus 100 may reduce the output intensity of the alarm signal if it is determined that the sleep depth of the object 10 is low. In contrast, as the sleep depth increases, the object 10 does not easily respond to the external environment. Accordingly, the apparatus 100 may increase the output intensity of the alarm signal if it is determined that the sleep depth of the object 10 is high.

Figure 23:
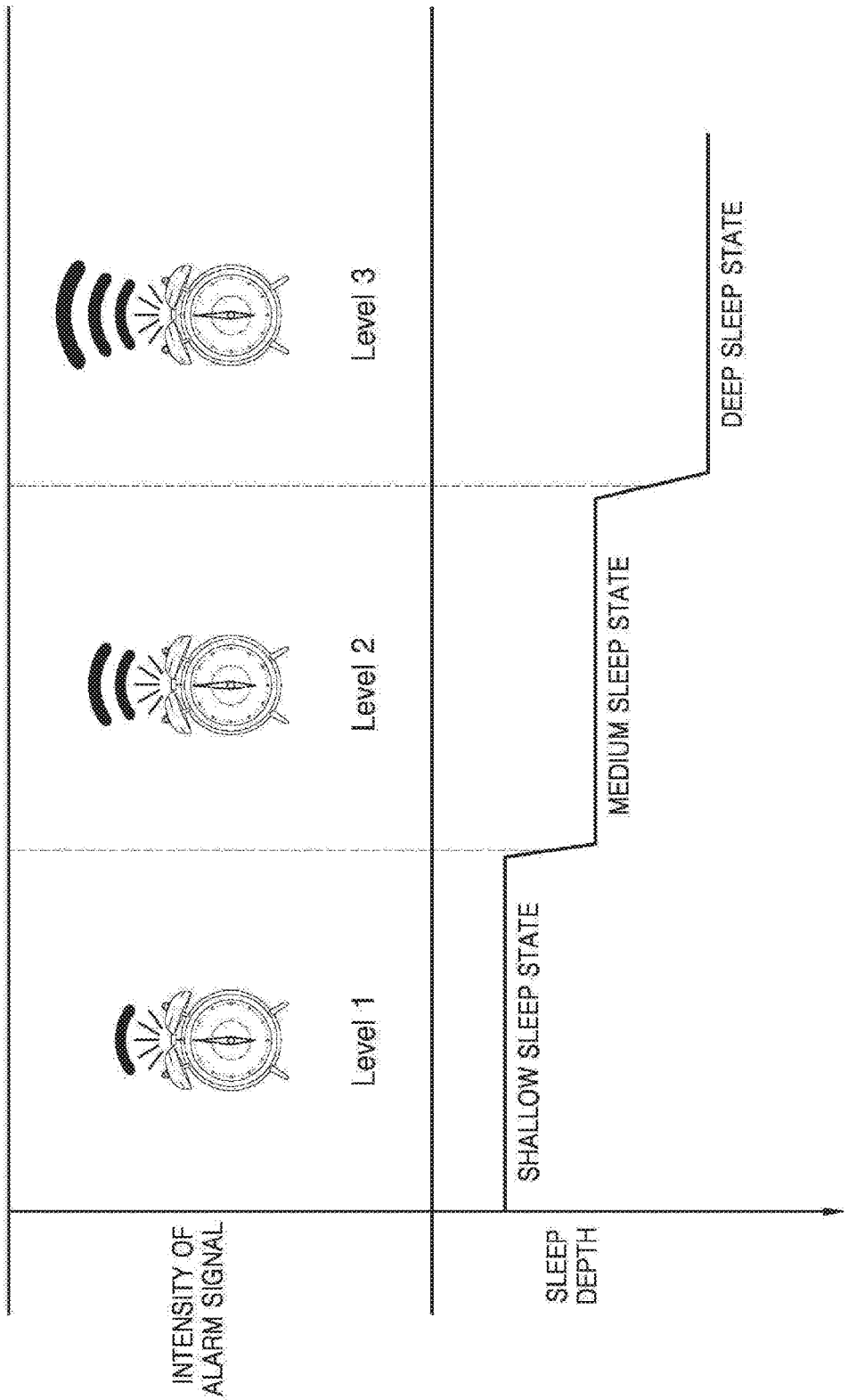
FIG. 23 is a view illustrating an example where an intensity of an alarm signal is adjusted according to a sleep depth of the object, according to an exemplary embodiment.

FIG. 23 is a view illustrating an example where an intensity of an alarm signal is adjusted according to a sleep depth of the object 10, according to an exemplary embodiment.

Referring to FIG. 23, when the object 10 is in a shallow sleep state, the apparatus 100 may determine the intensity of the alarm signal to be a first level, when the object 10 is in a transitional sleep state between the shallow sleep state and a deep sleep state, the apparatus 100 may determine the intensity of the alarm signal to be a second level, and when the object 10 is in the deep sleep state, the apparatus 100 may determine the intensity of the alarm signal to be a third level.

Accordingly, when the object 10 deeply sleeps, the apparatus 100 may increase the intensity of the alarm signal so that the object 10 may rapidly respond to the alarm signal.

Although an intensity of an alarm signal increases as a sleep depth increases in FIG. 23, the apparatus 100 may reduce the intensity of the alarm signal as the sleep depth increases.

Referring back to FIG. 22, the apparatus 100 may adjust an output cycle of the alarm signal according to the sleep depth of the object 10. For example, as the sleep depth of the object 10 increases, the apparatus 100 may increase the output cycle of the alarm signal in order to not wake up the object 10. Alternatively, as the sleep depth of the object 10 increases, the apparatus 100 may reduce the output cycle of the alarm signal in order to wake up the object 10.

The apparatus 100 may determine the alarm condition corresponding to the sleep depth of the object 10 by taking into account an urgency of the alarm event. For example, when the urgency of the alarm event is high, the apparatus 100 may reduce the output cycle of the alarm signal as the sleep depth of the object 10 increases, in order to wake up the object 10. Also, when the urgency of the alarm event is low, the apparatus 100 may increase the output cycle of the alarm signal as the sleep depth of the object 10 increases, in order not to wake up the object 10.

Figure 24:
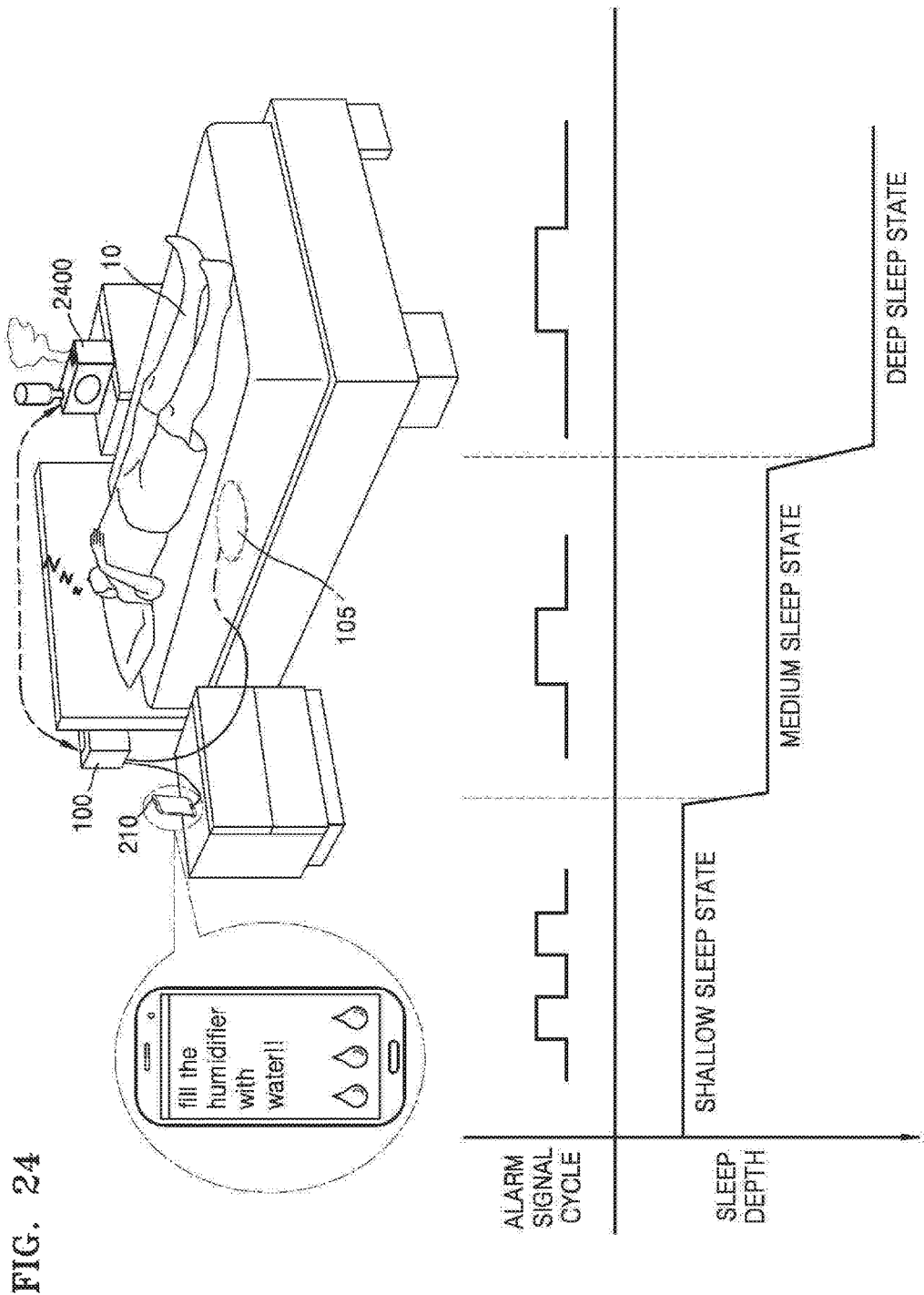
FIGS. 24 and 25 are views illustrating an example where an alarm signal cycle is adjusted according to a sleep depth of the object and an urgency of an alarm event, according to an exemplary embodiment.
Figure 25:
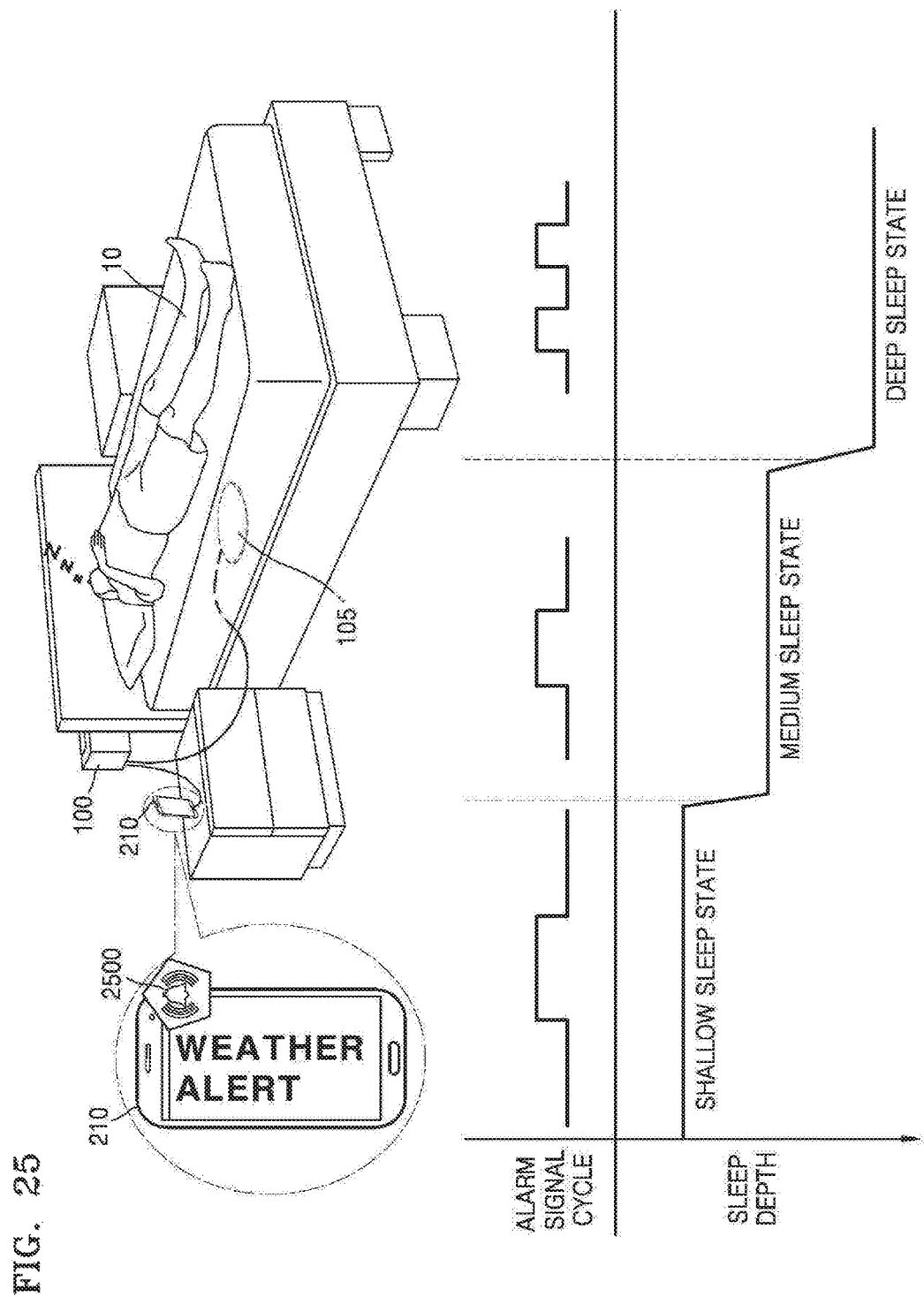

FIGS. 24 and 25 are views illustrating an example where an alarm signal cycle is adjusted according to a sleep depth of the object 10 and an urgency of an alarm event, according to an exemplary embodiment.

Referring to FIG. 24, the apparatus 100 may receive from a humidifier 2400 a signal indicating that the humidifier 2400 needs to be filled with water. In this case, the apparatus 100 may detect that an alarm event for outputting a message indicating that the humidifier 2400 needs to be filled with water occurs.

The apparatus 100 may determine an urgency of the alarm event. For example, the apparatus 100 may determine whether the alarm event corresponds to an urgent alarm event that is stored in the storage 108. Also, the apparatus 100 may analyze content that is included in a message that is received from the outside and may determine the urgency of the alarm event.

When the event for outputting the message indicating that the humidifier 2400 needs to be filled with water is not designated as the urgent alarm event, the apparatus 100 may determine that the urgency of the alarm event is low.

Since the urgency of the alarm event for outputting the message indicating that the humidifier 2400 needs to be filled with water is low, when the object 10 is deeply sleeping (e.g., in a NREM sleep state), the apparatus 100 may increase an output cycle of the alarm signal in order not to wake up the object 10. In contrast, when the object 10 is shallowly sleeping (e.g., in a REM sleep state), the apparatus 100 may reduce the output cycle of the alarm signal so that the object 10 fills the humidifier 2400 with water. The apparatus 100 may control the portable terminal 210 of the object 10 to output a message indicating that the humidifier 2400 needs to be filled with water according to the determined output cycle.

Referring to FIG. 25, the apparatus 100 may receive a disaster warning signal (e.g., an earthquake, flood, or fire warning signal) from an external server. In this case, the apparatus 100 may detect that an alarm event 2500 for outputting a disaster warning message and a disaster warning sound occurs.

The apparatus 100 may determine an urgency of the alarm event 2500. For example, since the alarm event 2500 corresponds to an urgent alarm event that is stored in the storage 108, the apparatus 100 may determine that the urgency of the alarm event 2500 is high. Also, the apparatus 100 may analyze a message (e.g., a weather alert message) that is included in the disaster warning signal received from the external server and may determine that the urgency of the alarm event 2500 is high.

Since the urgency of the alarm event 2500 is high, when the object 10 is deeply sleeping (e.g., in a NREM sleep state), the apparatus 100 may reduce an output cycle of an alarm signal in order to wake up the object 10. For example, the apparatus 100 may control the portable terminal 210 to output the disaster warning message and the disaster warning sound at 1-minute intervals when the object 10 is shallowly sleeping (e.g., in a REM sleep state), and may control the portable terminal 210 to output the disaster warning message and the disaster warning sound at 10-second intervals when the object 10 is deeply sleeping (e.g., in the NREM sleep state).

According to an exemplary embodiment, the apparatus 100 may determine an output time of the alarm signal according to a sleep depth of the object 10. For example, the apparatus 100 may control the portable terminal 210 not to output the alarm signal when the sleep depth of the object 10 is high (e.g., the NREM sleep state) and to output the alarm signal when the sleep depth of the object 10 is low (e.g., the REM sleep state).

According to an exemplary embodiment, the apparatus 100 may determine an output type of the alarm signal according to the sleep depth of the object 10. The output type of the alarm signal may be at least one of a vibration signal, an audio signal, and a video signal.

For example, when the sleep depth of the object 10 is high (e.g., the NREM sleep state), the apparatus 100 may output the alarm signal as a video signal, and when the sleep depth of the object 10 is low (e.g., the REM sleep state), the apparatus 100 may output the alarm signal as an audio signal. Also, when the urgency of the alarm event is high and the sleep depth of the object 10 is high, the apparatus 100 may output the alarm signal as all of a vibration signal, an audio signal, and a video signal.

An example where, when the object 10 is sleeping, the apparatus 100 may automatically notify an external device that the object 10 is sleeping will now be explained.

Figure 26:
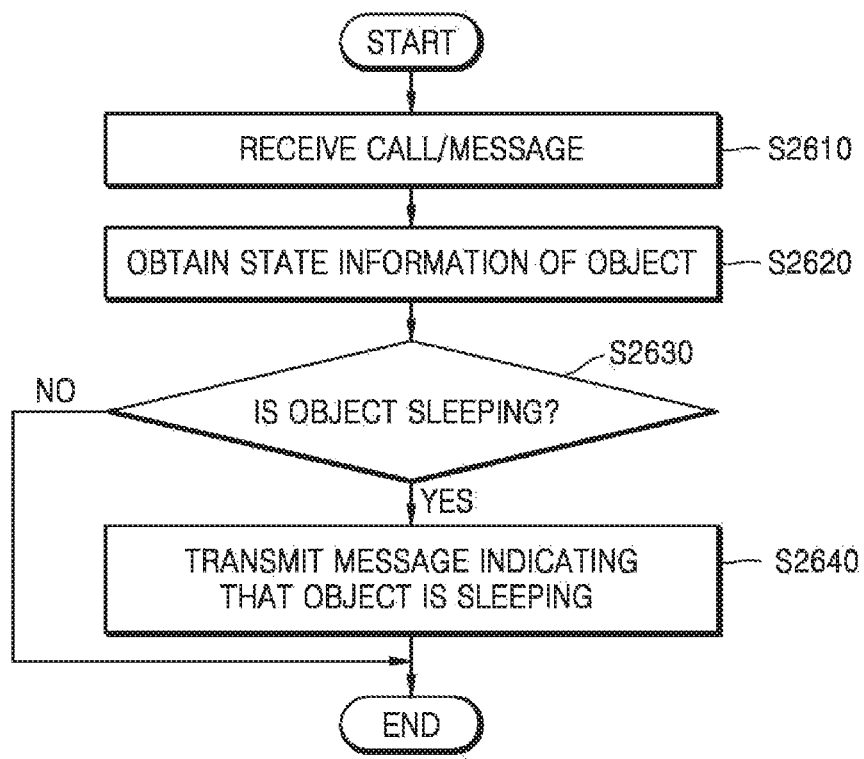
FIG. 26 is a flowchart illustrating a method of transmitting to the outside a message indicating that the object is sleeping, according to an exemplary embodiment.

FIG. 26 is a flowchart illustrating a method of transmitting to the outside a message indicating that the object 10 is sleeping, according to an exemplary embodiment.

In operation S2610, the apparatus 100 may detect that the portable terminal 210 of the object 10 receives a call or a message from an external device. According to an exemplary embodiment, the portable terminal 210 of the object 10 may be connected in a wired or wireless manner to the apparatus 100. According to another exemplary embodiment, the apparatus 100 may be included in the portable terminal 210.

In operation S2620, the apparatus 100 may obtain state information of the object 10. For example, the apparatus 100 may collect information sensed by the sensor 105 or an external IoT device, and may analyze a state of the object 10 based on the collected information. Also, the apparatus 100 may receive from the external IoT device information about the state of the object 10 that is analyzed by the external IoT device. Operation S2620 corresponds to operation S1510 of FIG. 15.

In operation S2630, the apparatus 100 may determine whether the object 10 is sleeping based on the state information of the object 10.

Operation S2630 corresponds to operation S1520 of FIG. 15.

If it is determined in operation S2630 that the object 10 is sleeping, the method proceeds to operation S2640. In operation S2640, the apparatus 100 may transmit a message indicating that the object 10 is sleeping to the external device. For example, when the object 10 is in a deep sleep state, the apparatus 100 may automatically transmit a response message indicating that the object 10 is sleeping to the external device. Also, when a predetermined period of time (e.g., 1 minute) elapses after the call or the message is received, the apparatus 100 may transmit the message indicating that the object 10 is sleeping to the external device.

In this case, the external device may be a device that is designated by the object 10. For example, in order to prevent private life information of the object 10 from being unrestrictedly exposed, only when the external device that transmits the call or the message is a designated device (e.g., a device of a family member or a significant other), the apparatus 100 may transmit the message indicating that the object 10 is sleeping to the external device.

Figure 27:
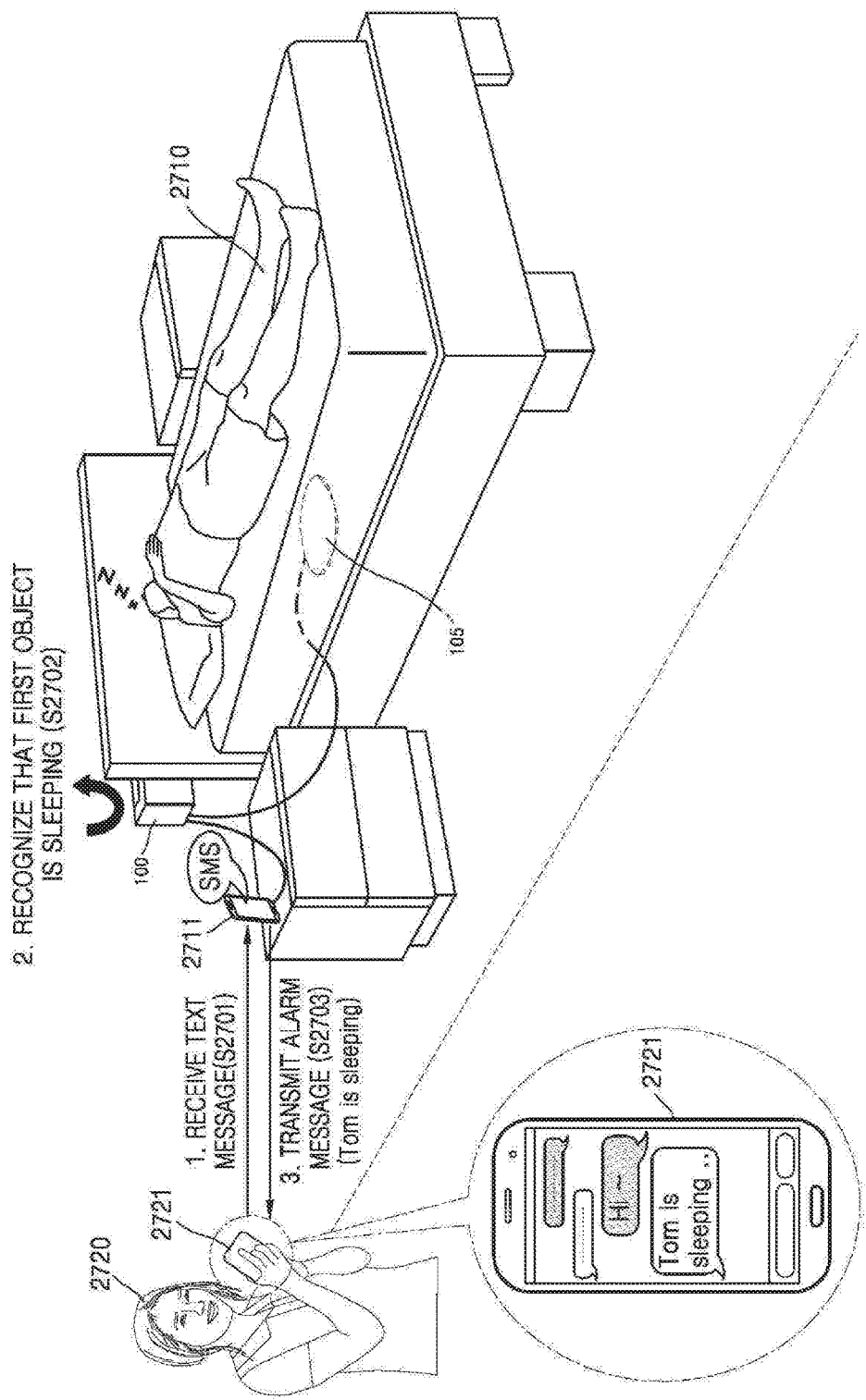
FIG. 27 is a view illustrating an example where the apparatus transmits a message indicating that a first object is sleeping to a device of a second object, according to an exemplary embodiment.

FIG. 27 is a view illustrating an example where the apparatus 100 transmits a message indicating that a first object is sleeping to a device of a second object, according to an exemplary embodiment.

Referring to FIG. 27, in operation S2701, a first device 2711 of a first object 2710 who is sleeping may receive a text message from a second device 2721 of a second object 2720. The first device 2711 may notify the apparatus 100 that the text message is received.

In operation S2702, since the apparatus 100 is monitoring a state of the first object 2710, the apparatus 100 may recognize that the first object 2710 is sleeping when the text message is received. The apparatus 100 may determine whether the second device 2721 of the second object 2720 is a terminal that is designated to share state information of the first object 2710. If it is determined that the second device 2721 is a terminal that is designated to share the state information of the first object 2710, the apparatus 100 may control the first device 2711 to transmit the state information of the first object 2710 to the second device 2721 of the second object 2720 (S2703).

For example, in operation S2703, the first device 2711 of the first object 2710 may transmit an alarm message (e.g., "Tom is sleeping") indicating that the first object 2710 is sleeping to the second device 2721.

According to an exemplary embodiment, when the first object 2710 is in a shallow sleep state, the apparatus 100 may control the first device 2711 not to output a text message reception alarm sound and to transmit a message indicating that the first object 2710 is sleeping.

According to an exemplary embodiment, the second object 2720 may recognize that the first object 2710 is sleeping by checking the alarm message (e.g., "Tom is sleeping") received from the first device 2711 in response to the text message. Accordingly, the second object 2720 does not have to unnecessarily wait for a response message of the first object 2710.

Figure 28:
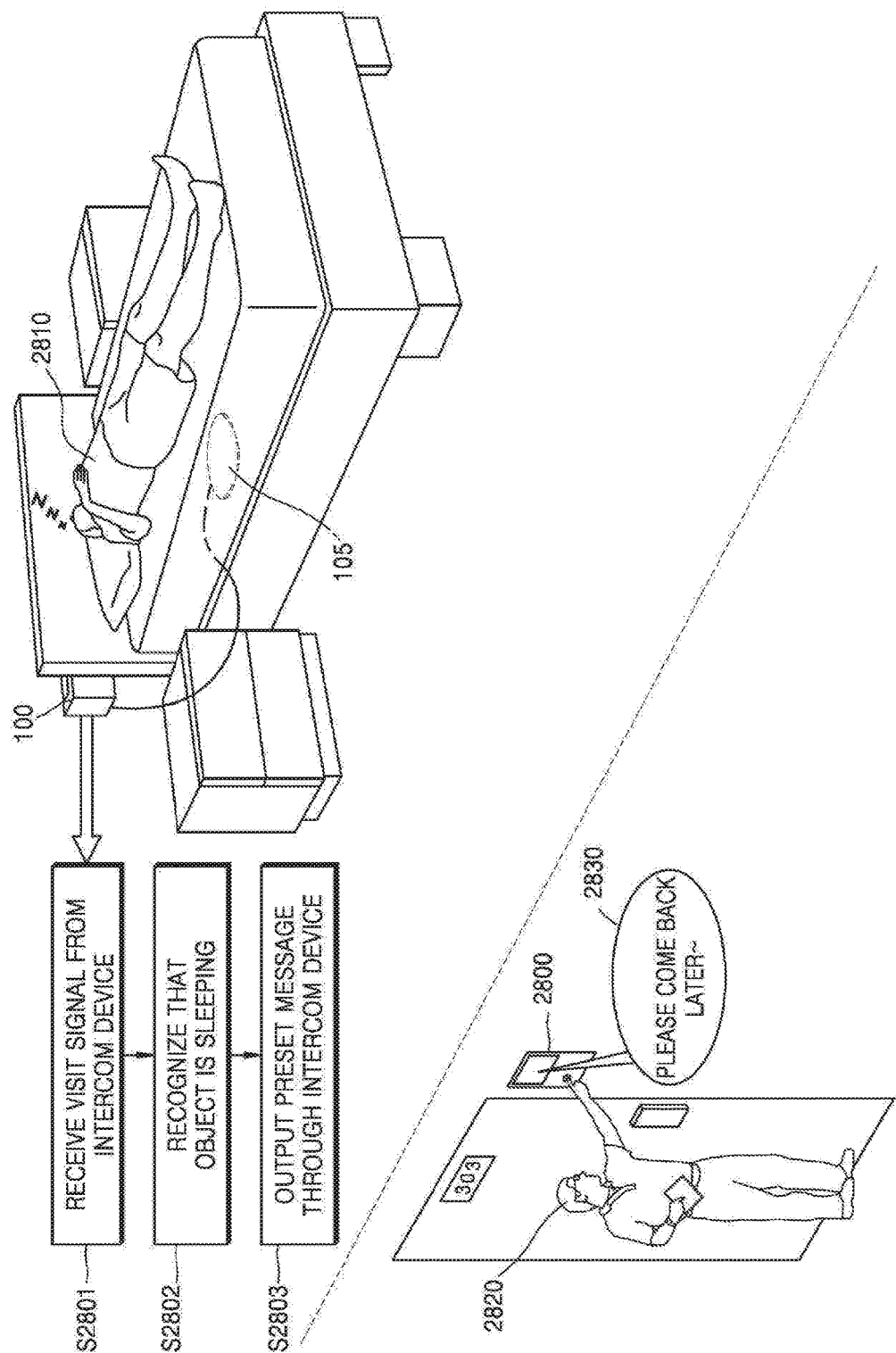
FIG. 28 is a view illustrating an example where the apparatus outputs a preset message through an intercom device, according to an exemplary embodiment.

FIG. 28 is a view illustrating an example where the apparatus 100 outputs a preset message through an intercom device 2800, according to an exemplary embodiment.

In operation S2801, the apparatus 100 may receive a visit signal from the intercom device 2800. For example, a second object 2820 may come to a house of a first object 2810 and may push a doorbell of the intercom device 2800 that is attached to a front door of the house of the first object 2810. In this case, the intercom device 2800 may transmit to the apparatus 100 a visit signal indicating that a stranger, the second object 2820, visits.

In operation S2802, since the apparatus 100 is monitoring a state of the first object 2810, the apparatus 100 may recognize that the first object 2810 is sleeping when the visit signal is received.

In operation S2803, since the first object 2810 is sleeping and thus may not respond to the visit of the second object 2820, the apparatus 100 may output a preset message through the intercom device 2800. For example, the apparatus 100 may control the intercom device 2800 to output the preset message saying 'Please come back later' as a voice or text. In this case, the second object 2820 does not have to wait for a long time in front of the house of the first object 2810 by pushing the doorbell several times.

When a home delivery service is expected at 3 PM, the first object 2810 may go to sleep after setting the apparatus 100 that when a visit signal is received, a message saying 'Please leave it at the security office' is output. When the second object 2820 (e.g., a courier) pushes the doorbell that is included in the intercom device 2800 at 3 PM, the apparatus 100 may control the intercom device 2800 to output the message saying 'Please leave it at the security office'.

A method performed by the apparatus 100 to change a wake-up alarm method when the object 10 wakes up and then went back to sleep according to an exemplary embodiment will now be explained.

Figure 29:
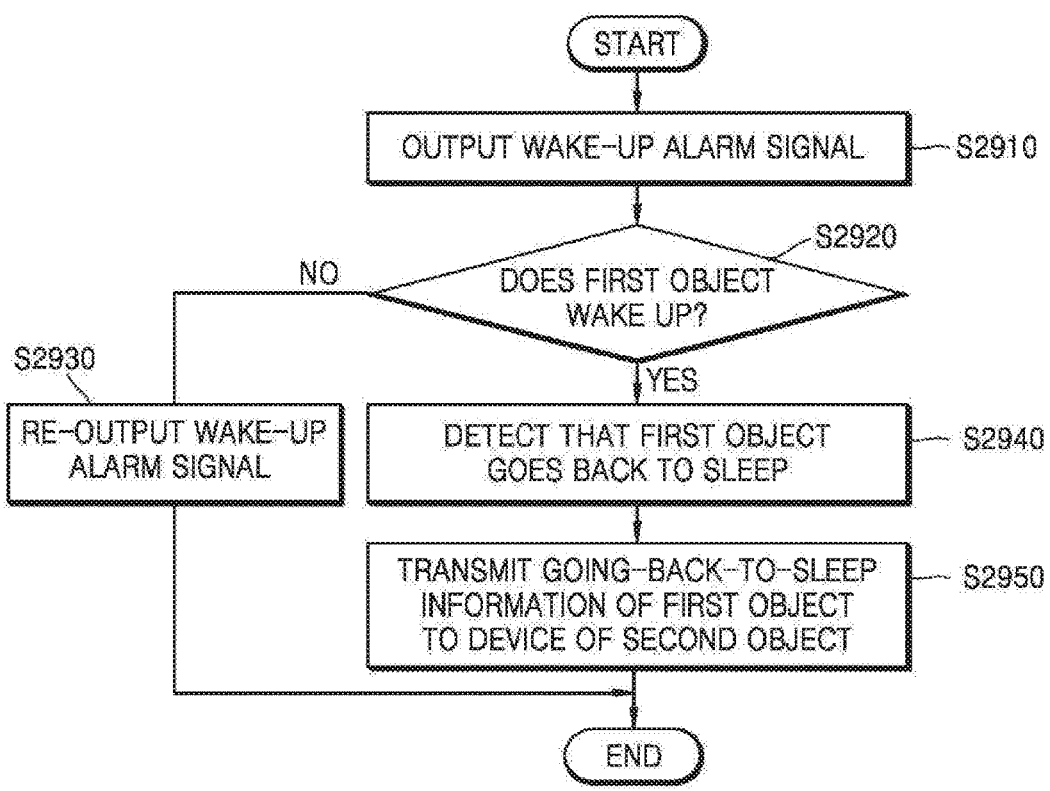
FIG. 29 is a flowchart illustrating a method performed by the apparatus to transmit going-back-to-sleep information of a first object to a device of a second object, according to an exemplary embodiment.

FIG. 29 is a flowchart illustrating a method performed by the apparatus 100 to transmit going-back-to-sleep information of a first object to a device of a second object, according to an exemplary embodiment.

In operation S2910, the apparatus 100 may output a wake-up alarm signal.

According to an exemplary embodiment, the apparatus 100 may output the wake-up alarm signal at a target wake-up time that is adjusted according to a sleep state of the first object. For example, when the number of times a posture of the first object is changed is greater than or equal to a critical number of times (e.g., 30 times), the apparatus 100 may change the target wake-up time from 7 AM to 7:10 AM and may output the wake-up alarm signal at 7:10 AM Also, when the number of times the posture of the first object is changed is greater than or equal to the critical number of times (e.g., 30 times), an apnea cycle of the first object is twice or more longer than an average apnea cycle, and a body temperature is higher than or equal to 38° C., the apparatus 100 may change the target wake-up time from 7 AM to 7:30 AM and may output the wake-up alarm signal at 7:30 AM In operation S2920, the apparatus 100 may determine whether the first object wakes up.

According to an exemplary embodiment, the apparatus 100 may capture an image of an eye of the first object in predetermined cycles by using an image sensor (e.g., the camera 232), and may detect a pupil by performing edge analysis on the captured image of the eye. In this case, when the pupil is detected a predetermined number of times or more in the image of the eye, the apparatus 100 may determine that the first object wakes up.

If it is determined in operation S2920 that the first object does not wake up after the wake-up alarm signal is output, the method proceeds to operation S2930. In operation S2930, the apparatus 100 may re-output the wake-up alarm signal. For example, the apparatus 100 may re-output a sound at 1-minute intervals to wake up the first object.

In operation S2940, the apparatus 100 may detect that the first object who wakes up went back to sleep. According to an exemplary embodiment, when it is detected that the first object sleeps within a preset time (e.g., 15 minutes) after the wake-up alarm signal is output, the apparatus 100 may determine that the first object went back to sleep.

For example, when it is detected that the first object wakes up according to the wake-up alarm signal at 7:30 AM, and then it is detected that the first object is sleeping at 7:40 AM, the apparatus 100 may determine that the first object went back to sleep.

A method performed by the apparatus 100 to determine whether the object 10 sleeps has been explained above.

In operation S2950, the apparatus 100 may transmit going-back-to-sleep information of the first object to the device of the second object. The second object may be a person that is designated by the first object. For example, the second object may be at least one of family members of the first object or a roommate of the first object. Also, the going-back-to-sleep information may be information indicating that the first object wakes up and then went back to sleep.

According to an exemplary embodiment, the second object may be a plurality of people. In this case, the apparatus 100 may transmit the going-back-to-sleep information of the first object to a plurality of devices. For example, the apparatus 100 may transmit information indicating that the first object is going back to sleep to a mobile phone of a friend of the first object and a mobile phone of a mother of the first object.

According to an exemplary embodiment, when the first object went back to sleep by mistake, the apparatus 100 may enable the second object to wake up the first object by transmitting the going-back-to-sleep information of the first object to the device of the second object.

Figure 30:
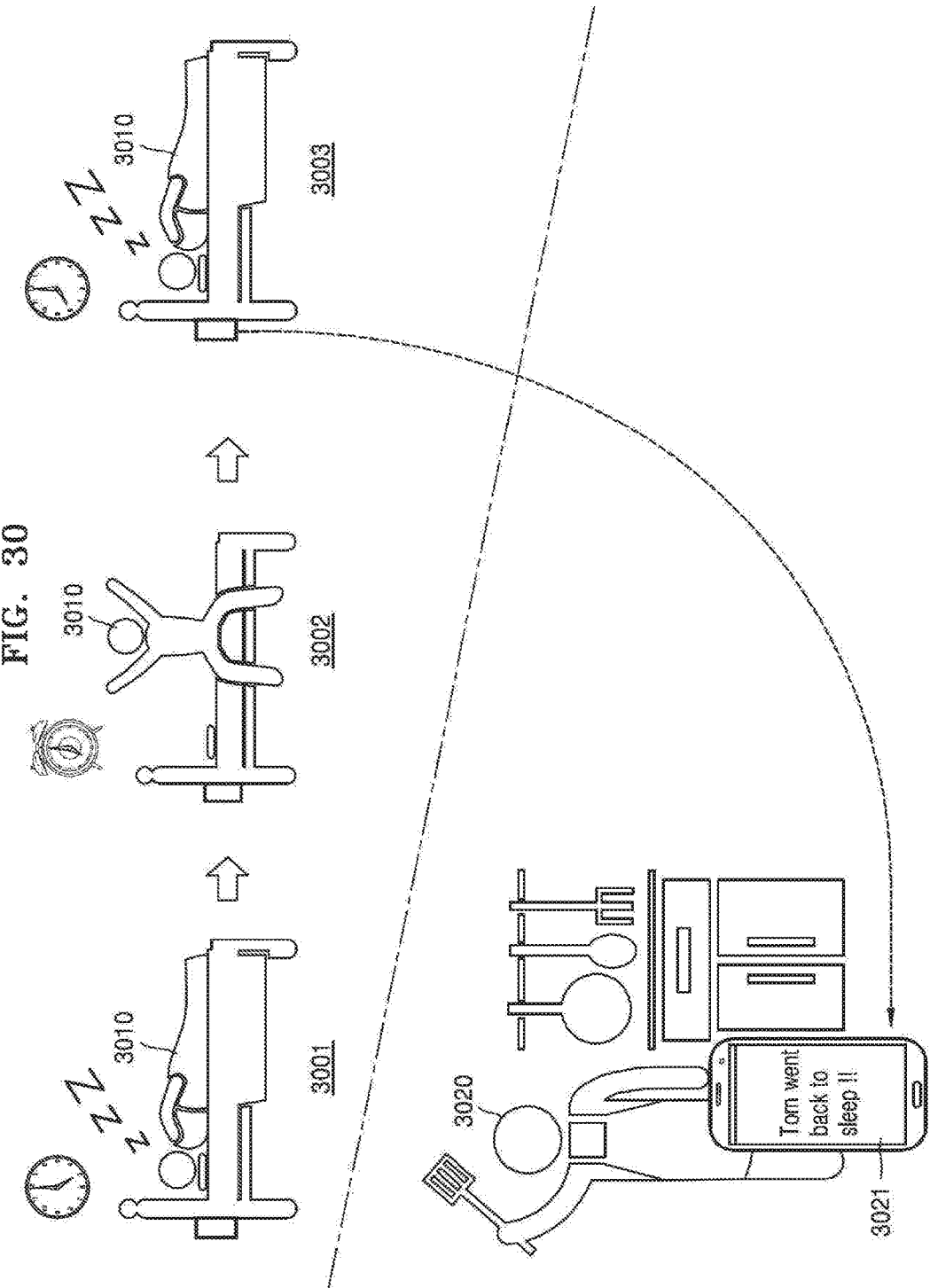
FIG. 30 is a view illustrating an example where the apparatus transmits going-back-to-sleep information of a first object to a device of a second object, according to an exemplary embodiment.

FIG. 30 is a view illustrating an example where the apparatus 100 transmits going-back-to-sleep information of a first object 3010 to a device of a second object 3020, according to an exemplary embodiment.

Referring to 3001 of FIG. 30, since it is 5 AM, the first object 3010 may be sleeping. The apparatus 100 may analyze a sleep pattern of the first object 3010 and may adjust a target wake-up time according to the sleep pattern of the first object 3010. For example, the apparatus 100 may determine the target wake-up time of the first object 3010 to be 7 AM Referring to 3002 of FIG. 30, the apparatus 100 may output a wake-up alarm signal at 7 AM that is the target wake-up time. For example, the apparatus 100 may output a specific sound through an alarm clock.

The first object 3010 may wake up in response to the wake-up alarm signal. In this case, the apparatus 100 may detect that the first object 3010 wakes up by using a motion sensor or a pressure sensor.

Referring to 3003 of FIG. 30, the first object 3010 may wake up, may inactivate an alarm function of the alarm clock, and then may go back to sleep. In this case, the apparatus 100 may detect that the first object 3010 went back to sleep, and may transmit going-back-to-sleep information of the first object 3010 to a mobile phone 3021 of the second object 3020 who exists around the first object 3010. For example, the apparatus 100 may transmit a message saying 'Tom went back to sleep!!' to the mobile phone 3021 of the second object 3020 who is a mother of the first object 3010.

The second object 3020 may check the message (e.g., 'Tom went back to sleep!!' displayed on the mobile phone 3021, may go to a bedroom of the first object 3010, and may wake up the first object 3010.

Figure 31:
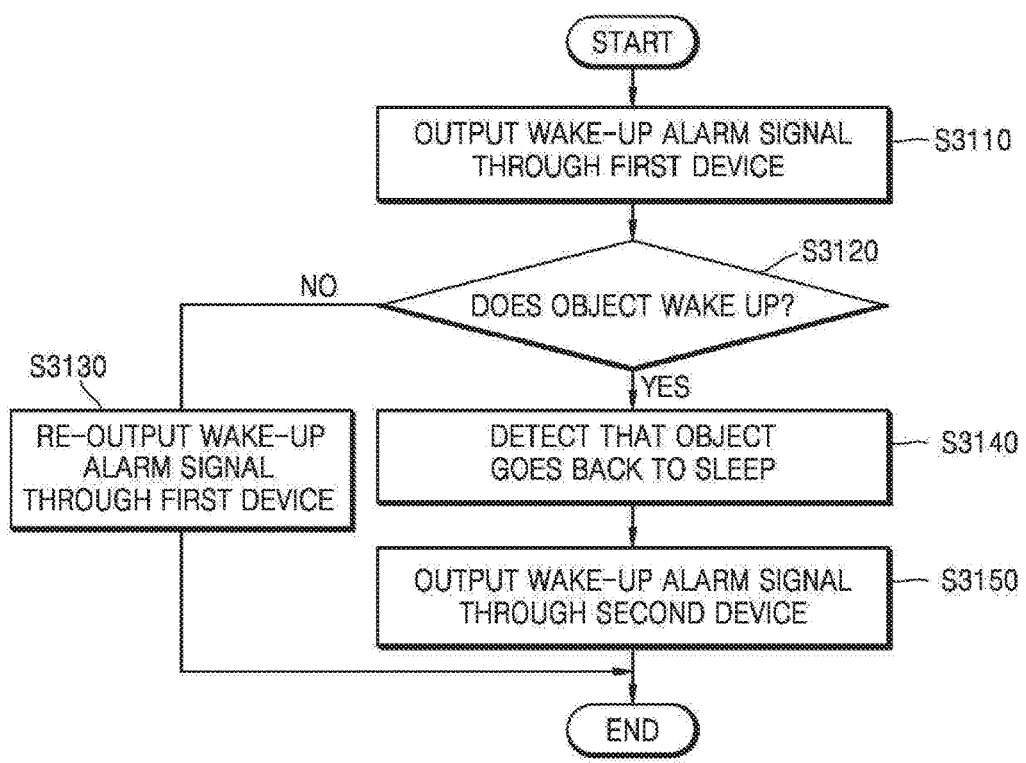
FIG. 31 is a flowchart illustrating a method performed by the apparatus to output a wake-up alarm signal by sequentially using a plurality of devices, according to an exemplary embodiment.

FIG. 31 is a flowchart illustrating a method performed by the apparatus 100 to output a wake-up alarm signal by sequentially using a plurality of devices, according to an exemplary embodiment.

In operation S3110, the apparatus 100 may output a wake-up alarm signal through a first device. For example, the apparatus 100 may output the wake-up alarm signal through one of an alarm clock, the portable terminal 210, the wearable terminal 220, and the display device 230 of the object 10.

According to an exemplary embodiment, the apparatus 100 may output the wake-up alarm signal at a target wake-up time that is adjusted according to a sleep state of the object 10.

In operation S3120, the apparatus 100 may determine whether the object 10 wakes up. The apparatus 100 may determine whether the object 10 wakes up by using one or more of the previously described methods.

If it is determined in operation S3120 that the object 10 does not wake up after the wake-up alarm signal is output, the method proceeds to operation S3130. In operation S3130, the apparatus 100 may re-output the wake-up alarm signal through the first device. For example, the apparatus 100 may re-output a sound at 1-minute intervals through the first device to wake up the object 10.

In operation S3140, the apparatus 100 may detect that the object 10 who wakes up went back to sleep. According to an exemplary embodiment, when it is detected that the object 10 seeps within a preset time (e.g., 30 minutes) after the wake-up alarm signal is output, the apparatus 100 may determine that the object 10 went back to sleep.

Methods performed by the apparatus 100 to determine whether the object 10 sleeps have been described above.

In operation S3150, if it is determined that the object 10 went back to sleep, the apparatus 100 may output the wake-up alarm signal through a second device that is different from the first device. For example, the apparatus 100 may transmit to the second device a control command to output the wake-up alarm signal.

An example where the apparatus 100 further outputs a wake-up alarm signal through a second device that is different from a first device will now be explained with reference to FIG. 32.

Figure 32:
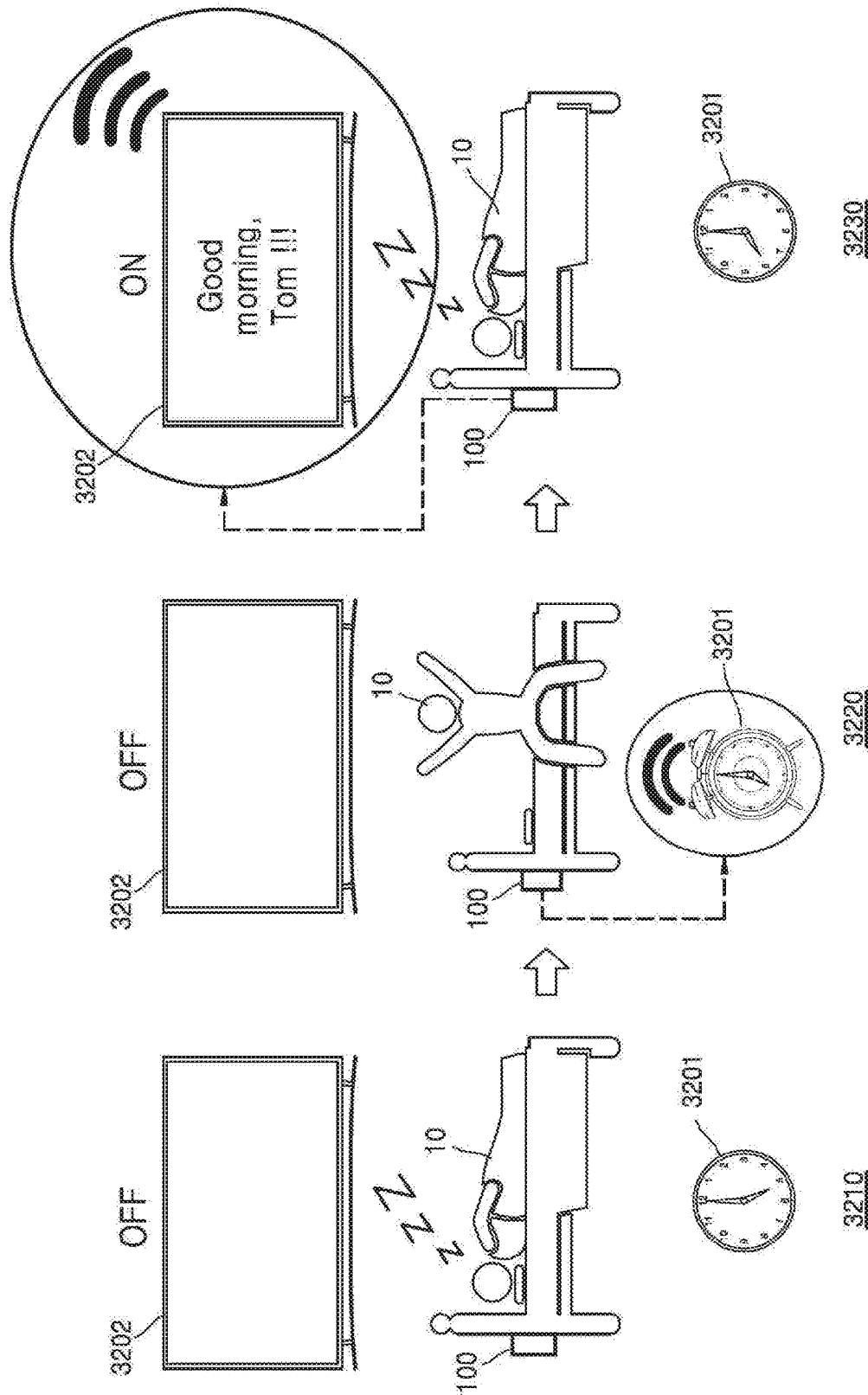
FIG. 32 is a view illustrating an example where, when the object went back to sleep, the apparatus outputs a wake-up alarm signal through a display device as well as an alarm clock, according to an exemplary embodiment.

FIG. 32 is a view illustrating an example where the apparatus 100 outputs a wake-up alarm signal through a display device 3002 as well as an alarm clock 3001 when the object 10 went back to sleep, according to an exemplary embodiment.

Referring to 3210 of FIG. 32, since it is 5 AM, the object 10 may be sleeping. The apparatus 100 may analyze a sleep pattern of the object 10 and may adjust a target wake-up time according to the sleep pattern of the object 10. For example, the apparatus 100 may determine the target wake-up time of the object 10 to be 7 AM Referring to 3220 of FIG. 32, the apparatus 100 may output a wake-up alarm signal at 7 AM that is the target wake-up time. For example, the apparatus 100 may output a first wake-up alarm signal (e.g., an alarm sound) through the alarm clock 3001. The object 10 may wake up in response to the first wake-up alarm signal. In this case, the apparatus 100 may detect that the object 10 wakes up by using a motion sensor or a pressure sensor.

Referring to 3230 of FIG. 32, the object 10 may wake up, may inactivate an alarm function of the alarm clock 3001, and may go back to sleep. The apparatus 100 may detect that the object 10 went back to sleep and may output a second wake-up alarm signal through the display device 3002. For example, the display device 3002 may output a wake-up alarm sound and a wake-up alarm message (e.g., Good morning, Tom!!!).

According to an exemplary embodiment, when the object 10 wakes up and then went back to sleep by mistake, the apparatus 100 may effectively wake up the object 10 by outputting the second wake-up alarm signal through a second device that is different from a first device that outputs the first wake-up alarm signal.

When the object 10 went back to sleep after the second wake-up alarm signal is output, the apparatus 100 may output a third wake-up alarm signal through a third device. As non-limiting examples, the apparatus 100 may output a vibration signal through a smart watch that is worn on the object 10.

Figure 33:
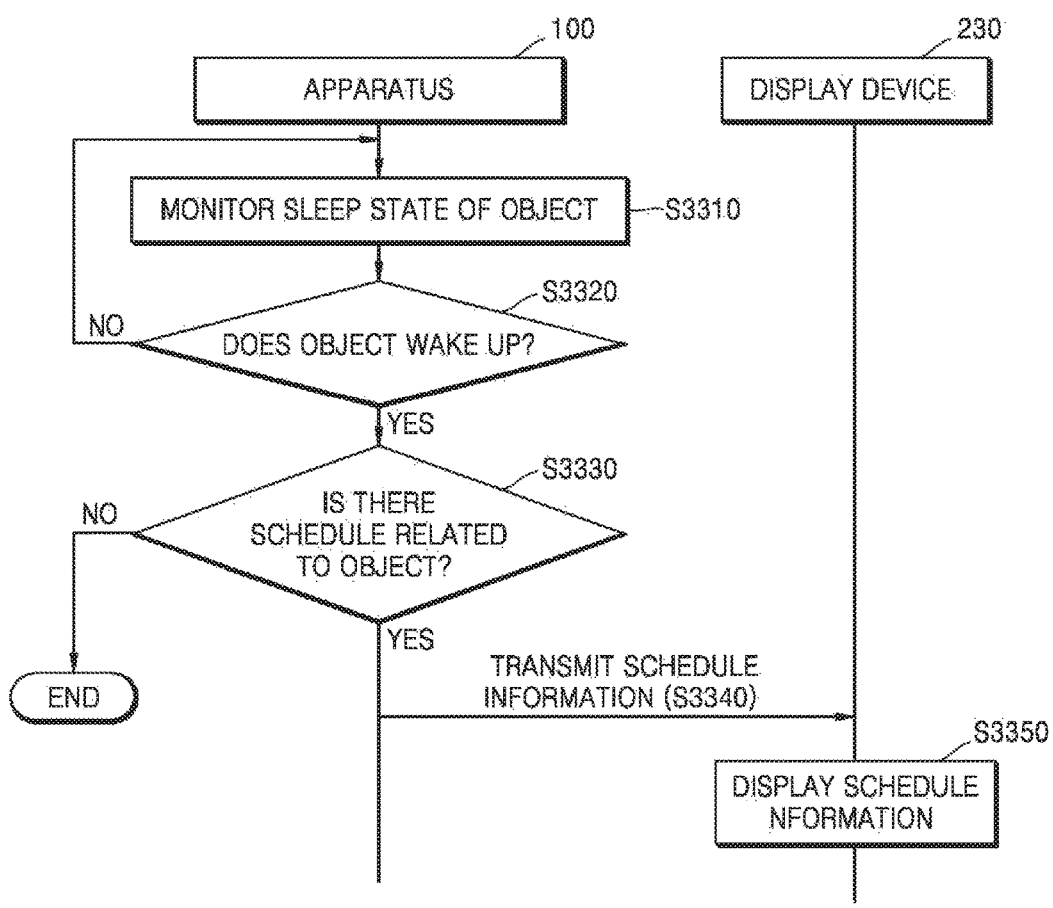
FIG. 33 is a timing diagram illustrating a method of displaying schedule information through a display device when the object wakes up, according to an exemplary embodiment.

FIG. 33 is a timing diagram illustrating a method of displaying schedule information through a display device when the object 10 wakes up, according to an exemplary embodiment.

In operation S3310, the apparatus 100 may monitor a sleep state of the object 10. Exemplary methods performed by the apparatus 100 to monitor a sleep state of the object 10 have been described above.

In operation S3320, the apparatus 100 may determine whether the object 10 wakes up. Exemplary methods performed by the apparatus 100 to determine whether the object 10 wakes up have been described above.

If it is determined in operation S3320 that the object 10 wakes up, the method proceeds to operation S3330. In operation S3330, the apparatus 100 may determine whether there is a schedule related to the object 10. For example, the apparatus 100 may determine whether there is a schedule registered in a personal cloud server of the object 10 or the portable terminal 210 of the object 10.

If it is determined in operation S3330 that there is a schedule related to the object 10, the method proceeds to operation S3340. In operation S3340, the apparatus 100 may transmit schedule information to the display device 230.

When the apparatus 100 is included in the display device 230, operation S3340 may be omitted.

In operation S3350, the display device 100 may display the schedule information. For example, the display device 100 may display information about a schedule that is to be performed within a predetermined period of time after the object 10 wakes up or a first event scheduled after the object 10 wakes up (e.g., buying a train ticket).

According to an exemplary embodiment, the object 10 may rapidly check the schedule information through the display device 230 after waking up. In particular, when there is a special event, the object 10 may be reminded of the special event after waking up. For example, when an auction of a specific product on a social commerce site starts at 6 AM, the object 10 may set a wake-up alarm to 5:55 AM and may go to sleep. When the object 10 wakes up at 5:55 AM, the object 10 may check a message (e.g., an auction of a specific product starts at 6 AM) that is output through the display device 230.

Figure 34:
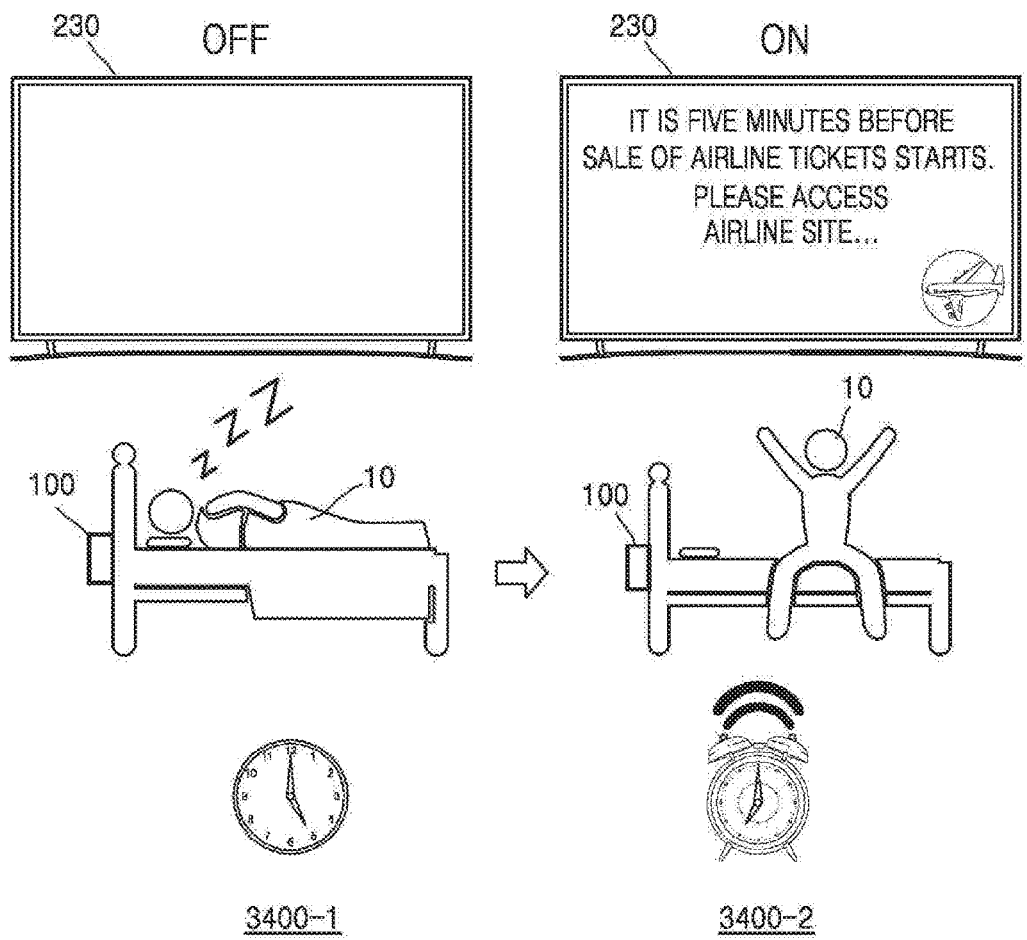
FIG. 34 is a view illustrating an example where, when the object wakes up, schedule information is displayed on the display device, according to an exemplary embodiment.

FIG. 34 is a view illustrating an example where, when the object 10 wakes up, schedule information is displayed on the display device 230, according to an exemplary embodiment.

Referring to 3400-1 of FIG. 34, the object 10 may set a wake-up alarm to 7 AM that is 2 hours earlier than 9 AM, which is an average wake-up time, in order to buy a discount airline ticket that is offered by an airline as a special event, and then may go to sleep. In this case, a target wake-up time of the object 10 may be 7 AM Referring to 3400-2 of FIG. 34, the apparatus 100 may output a wake-up alarm signal at 7 AM that is the target wake-up time. For example, the apparatus 100 may output a wake-up alarm sound through an alarm clock.

The object 10 may wake up in response to the wake-up alarm signal. In this case, since the object 10 wakes up 2 hours earlier than 9 AM, the object 10 may forget to buy the airline ticket and go back to sleep. Accordingly, in order to prevent the object 10 from forgetting a special event, the apparatus 100 may control the display device 230 to display the schedule information within a predetermined time (e.g., 1 hour) after the wake-up alarm signal is output. For example, when sales of discount airline tickets start at 7:05 AM, the apparatus 100 may output a voice message or a text message, 'It is 5 minutes before the sale of airline tickets starts. Please access an airline site,' through the display device 230.

An example where power consumption of a peripheral device is reduced while the object 10 is sleeping will now be explained.

Figure 35:
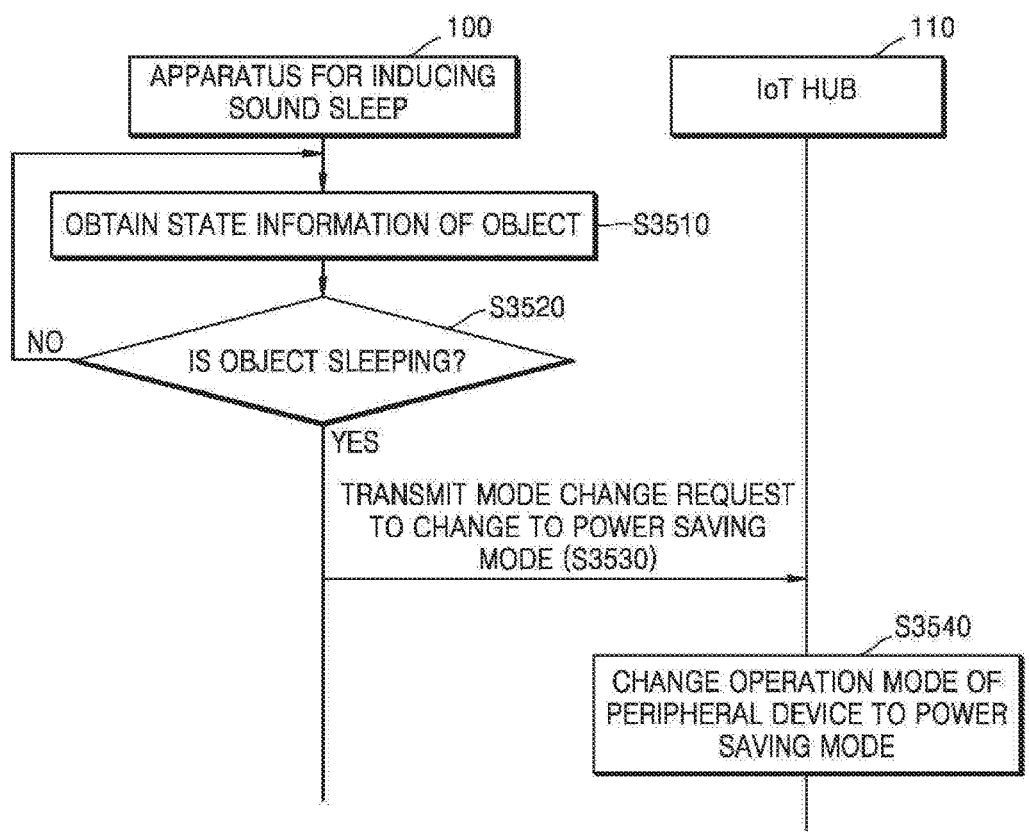
FIG. 35 is a timing diagram illustrating a method of changing an operation mode of a peripheral device to a power saving mode when the object is sleeping, according to an exemplary embodiment.

FIG. 35 is a timing diagram illustrating a method of changing an operation mode of a peripheral device to a power saving mode when the object 10 is sleeping, according to an exemplary embodiment.

In operation S3510, the apparatus 100 may obtain state information of the object 10. Operation S3510 corresponds to operation S1510 of FIG. 15.

In operation S3520, the apparatus 100 may determine whether the object 10 is sleeping based on the state information of the object 10. Operation S3520 corresponds to operation S1520 of FIG. 15.

If it is determined in operation S3520 that the object 10 is sleeping, the method proceeds to operation S3530. In operation S3530, the apparatus 100 may transmit to the IoT hub 200 a mode change request for changing an operation mode of a peripheral device to a power saving mode.

According to an exemplary embodiment, the apparatus 100 may select some peripheral devices that may change to the power saving mode from among a plurality of peripheral devices that are connected to the IoT hub 200. For example, the apparatus 100 may classify a refrigerator, an air cleaner, and a humidifier as devices that need to continuously operate, and may classify a washing machine, a microwave oven, a TV, a computer, and a Wi-Fi access point (AP) as devices that may change to the power saving mode.

In operation S3540, the IoT hub 200 may change the operation mode of the peripheral device to the power saving mode, in response to the mode change request.

For example, the IoT hub 200 may transmit a control signal for commanding to set the power saving mode to a peripheral device that is connected to the IoT hub 200. Also, the IoT hub 200 may transmit to a power supply controller a request to cut off power supply to some devices (e.g., a TV, a microwave oven, an oven, and a coffee machine). In this case, the power supply controller may cut off power supply to the some devices, thereby reducing power consumption.

According to an exemplary embodiment, the IoT hub 200, instead of the apparatus 100, may select some peripheral devices that may change to the power saving mode, from among a plurality of peripheral devices. In this case, the IoT hub 200 may transmit a control command to change the selected some peripheral devices to the power saving mode and may receive mode change completion messages from the selected peripheral devices.

Figure 36:
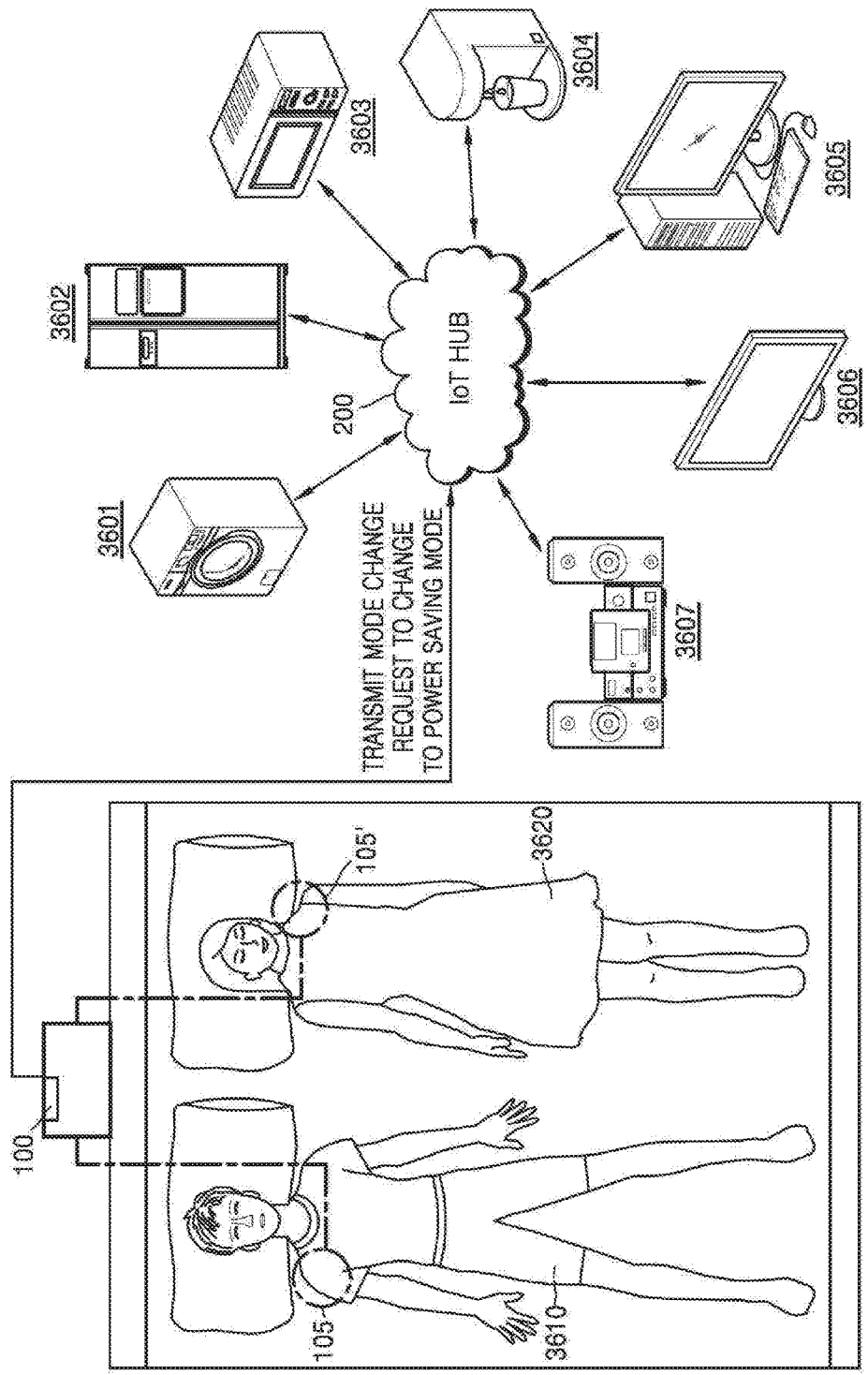
FIG. 36 is a view illustrating an example where, when a plurality of objects are sleeping, an operation mode of a peripheral device is changed to a power saving mode, according to an exemplary embodiment.

FIG. 36 is a view illustrating an example where, when a plurality of objects are sleeping, an operation mode of a peripheral device is changed to a power saving mode, according to an exemplary embodiment. FIG. 36 will be explained on the assumption that a first object 3610 and a second object 3620 sleep in one bed.

Referring to FIG. 36, the first object 3610 may go to sleep at 11 PM and the second object 3620 may go to sleep at 12 AM. The apparatus 100 may detect that the first object 3610 and the second object 3620 go to sleep by monitoring states of the first object 3610 and the second object 3620 through the sensors 105 and 105'.

The apparatus 100 may transmit a mode change request to the IoT hub 200 based on a sleep time of the second object 3620 who goes to sleep later than the first object 3610. For example, the apparatus 100 may transmit the mode change request to the IoT hub 200 at 12 AM, the time at which the second object 3620 goes to sleep. In this case, the IoT hub 200 may transmit a command to set a power saving mode to a washing machine 3601, a refrigerator 3602, a microwave oven 3603, a computer 3605, a smart TV 3606, and an audio output device 3607 that are connected to the IoT hub 200.

According to an exemplary embodiment, the apparatus 100 may transmit the mode change request to the IoT hub 200 at 11 PM at which the first object 3610 goes to sleep for a device that is not used by the second object 3620 and is used by only the first object 3610. For example, the apparatus 100 may transmit the mode change request to a laptop computer of the first object 3610 that is used only by the first object 3610 at 11 PM.

Figure 37:
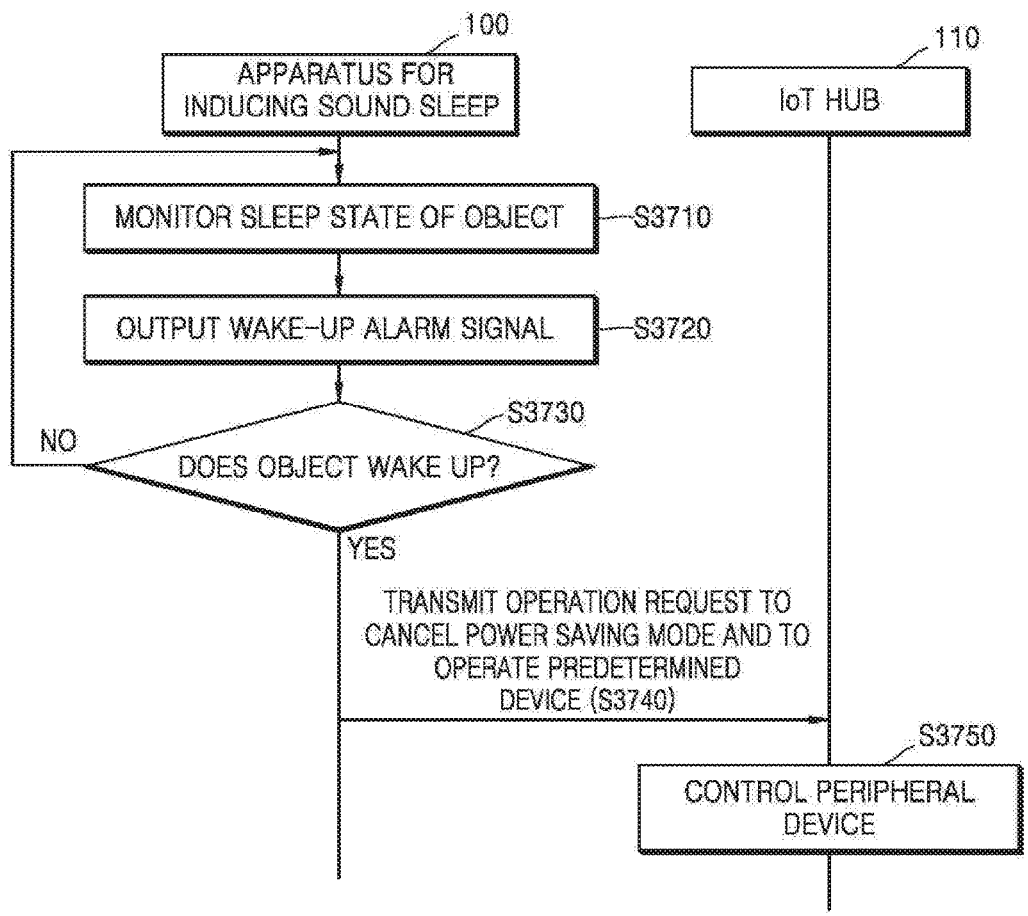
FIG. 37 is a timing diagram illustrating a method of cancelling a power saving mode of a peripheral device (or requesting for an operation of a predetermined device) when the object wakes up, according to an exemplary embodiment.

FIG. 37 is a timing diagram illustrating a method of cancelling a power saving mode of a peripheral device (or requesting an operation of a predetermined device) when the object 10 wakes up, according to an exemplary embodiment.

In operation S3710, the apparatus 100 may monitor a sleep state of the object 10.

For example, the apparatus 100 may obtain sleep state information of the object 10 who is sleeping.

Operation S3710 corresponds to operation S3310 of FIG. 33.

In operation S3720, the apparatus 100 may output a wake-up alarm signal.

According to an exemplary embodiment, the apparatus 100 may output the wake-up alarm signal at a target wake-up time that is adjusted according to the sleep state of the object 10.

In operation S3730, the apparatus 100 may determine whether the object 10 wakes up.

According to an exemplary embodiment, if it is determined in operation S3730 that the object 10 does not wake up, the method returns to operation S3710 in which the apparatus 100 may continuously monitor the sleep state of the object 10.

If it is determined in operation S3730 that the object 10 wakes up, the method proceeds to operation S3740. In operation S3740, the apparatus 100 may transmit to the IoT hub 200 an operation request to cancel a power saving mode and to operate a predetermined device. For example, the apparatus 100 may transmit to the IoT hub 200 a request to change the operation modes of IoT devices, which were changed to power saving modes when the object 10 went to sleep, to active modes. Also, the apparatus 100 may transmit a request to operate specific devices to the IoT hub 200 based on routine behavior pattern information after the object 10 wakes up. For example, the apparatus 100 may transmit to the IoT hub 200 a request to start up a car or to turn on a boiler.

In operation S3750, the IoT hub 200 may control a peripheral device in response to the request to cancel the power saving mode or to operate the specific device. An operation performed by the IoT hub 200 to control the peripheral device will now be explained in detail with reference to FIG. 38.

Figure 38:
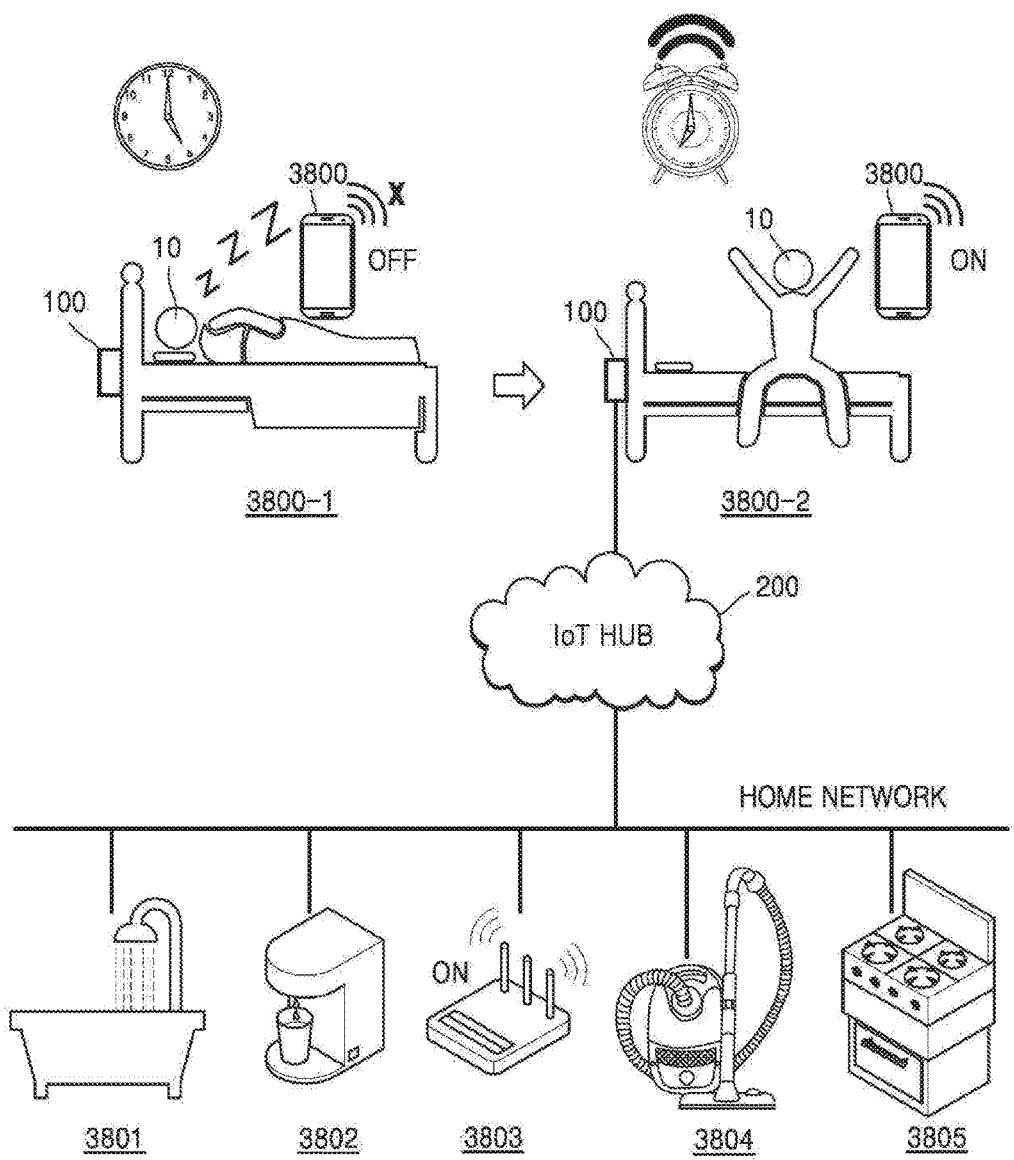
FIG. 38 is a view illustrating an example where, when the object wakes up, a predetermined device automatically operates, according to an exemplary embodiment.

FIG. 38 is a view illustrating an example where, when the object 10 wakes up, a predetermined device automatically operates, according to an exemplary embodiment.

Referring to 3800-1 of FIG. 38, since it is 5 AM, the object 10 may be sleeping. The apparatus 100 may analyze a sleep pattern of the object 10 and may adjust a target wake-up time according to the sleep pattern of the object 10. For example, the apparatus 100 may determine the target wake-up time of the object 10 to be 7 AM Also, in order to reduce power consumption while the object 10 is sleeping, the apparatus 100 may request the IoT hub 200 cut off power supply to a coffee machine 3802, a Wi-Fi AP 3803, a cleaner 3804, or an oven 3805 or to change an operation mode to a power saving mode. Accordingly, a Wi-Fi communication function of a mobile phone 3800 of the object 10 may be inactivated while the object 10 is sleeping.

Referring to 3800-2 of FIG. 38, the apparatus 100 may output a wake-up alarm signal at 7 AM that is the target wake-up time. For example, the apparatus 100 may output a wake-up alarm sound through an alarm clock.

The object 10 may wake up in response to the wake-up alarm signal. The apparatus 100 may detect that the object 10 wakes up. In this case, the apparatus 100 may control peripheral devices through the IoT hub 200 to cause the peripheral devices, which were changed to power saving modes while the object 10 was sleeping, to cancel the power saving modes. For example, the Wi-Fi AP 3803 may normally operate. Accordingly, when the object 10 wakes up, the Wi-Fi communication function of the mobile phone 3800 of the object 10 may be automatically activated.

Also, the apparatus 100 may predict a behavior after the object 10 wakes up based on routine behavior pattern information of the object 10, and may operate some devices in advance. For example, the apparatus 100 may control a shower 3801 to fill water for a half-body bath, may control the coffee machine 3802 to brew coffee, may control the cleaner 3804 to start a cleaning operation, or may control the oven 3805 to start a preheating operation through the IoT hub 200.

According to an exemplary embodiment, when a plurality of objects (people) live together, the apparatus 100 may transmit a power saving mode cancel request to the IoT hub 200 based on a wake-up time of a first object who wakes up the earliest from among the plurality of objects.

Also, when only a second object from among the plurality of objects drinks coffee in the morning, the apparatus 100 may control the coffee machine 3802 to brew coffee at a wake-up time of the second object. In this case, information about devices that are commonly used by the plurality of objects and devices that are individually used may be stored in the apparatus 100.

The apparatus 100 according to an exemplary embodiment may monitor a sleep state of the object 10 and may adaptively provide an alarm according to the sleep state of the object 10. Also, the apparatus 100 may improve the sleep quality of the object 10 by controlling peripheral devices according to the sleep state of the object 10.

The above-described exemplary embodiments may be implemented as an executable program, and may be executed by a general-purpose digital computer that runs the program by using a computer-readable recording medium. Also, a structure of data used in the method may be recorded by using various units on a non-transitory computer-readable medium. Non-limiting examples of the computer-readable medium include storage media such as magnetic storage media (e.g., read only memories (ROMs), floppy discs, or hard discs) and optically readable media (e.g., compact disk-read only memories (CD-ROMs), or digital versatile disks (DVDs)).

While certain exemplary embodiments have been shown and described, it will be understood by those of ordinary skill in the art that various changes in form and details may be made therein without departing from the spirit and scope of the inventive concept as defined by the appended claims and their equivalents. The described one or more exemplary embodiments should be considered in descriptive sense only and not for purposes of limitation. Therefore, the scope of the inventive concept is defined not by the detailed description, but by the appended claims and their equivalents, and all differences within the scope should be construed as being included in the inventive concept.

What is claimed is:

1. A method performed by an apparatus configured to improve a sleep of an object who is sleeping, the method comprising:
   determining a first wake-up time of the object based on schedule information corresponding to a schedule of the object;
   receiving bio-information of the object;
   determining a sleep state of the object from the bio-information;
   changing the first wake-up time to a second wake-up time based on the sleep state of the object;
   outputting a wake-up alarm signal at the second wake-up time;
   measuring an actual wake-up time of the object;
   determining a remaining time from the actual wake-up time of the object to a preset critical time;
   selecting at least one activity that is to be performed by the object during the remaining time; and
   providing information about the selected at least one activity to the object.

2. A non-transitory computer-readable recording medium having embodied thereon a program for executing the method of claim 1.

3. A method performed by an apparatus configured to improve a sleep of an object who is sleeping, the method comprising:
- determining a first wake-up time of the object based on schedule information corresponding to a schedule of the object;
- receiving bio-information of the object;
- determining a sleep state of the object from the bio-information;
- changing the first wake-up time to a second wake-up time based on the sleep state of the object;
- outputting a wake-up alarm signal at the second wake-up time;
- detecting that the object wakes up; and
- providing information about an event that occurs within a preset time after the object wakes up.

4. A non-transitory computer-readable recording medium having embodied thereon a program for executing the method of claim 3.

5. An apparatus configured to improve a sleep of an object who is sleeping, the apparatus comprising:
- a communicator configured to receive bio-information of the object that is measured by a sensor;
- a controller configured to determine a sleep state of the object based on the bio-information, determine a first wake-up time of the object based on schedule information corresponding to a schedule of the object, and change the first wake-up time to a second wake-up time based on the sleep state of the object; and
- an output device configured to output a wake-up alarm signal at the second wake-up time, wherein the controller is further configured to detect that the object is sleeping within a preset time after the second wake-up time, and the communicator is further configured to transmit information indicating that the object is sleeping to a device of a designated third party.

6. An apparatus configured to improve a sleep of an object who is sleeping, the apparatus comprising:
- a communicator configured to receive bio-information of the object that is measured by a sensor;
- a controller configured to determine a sleep state of the object based on the bio-information, determine a first wake-up time of the object based on schedule information corresponding to a schedule of the object, and change the first wake-up time to a second wake-up time based on the sleep state of the object; and
- an output device configured to output a wake-up alarm signal at the second wake-up time, wherein the output device comprises a first device and a second device, the second device being different from the first device, and the controller is further configured to output a first wake-up alarm signal through the first device at the second wake-up time, and, in response to it being detected that the object is sleeping within a preset time after the second wake-up time, output a second wake-up alarm signal through the second device.

* * * * *